US008106170B2

(12) United States Patent
Ter Meulen et al.

(10) Patent No.: US 8,106,170 B2
(45) **Date of Patent: *Jan. 31, 2012**

(54) COMPOSITIONS AGAINST SARS-CORONAVIRUS AND USES THEREOF

(75) Inventors: Jan Henrik Ter Meulen, Amsterdam (NL); Edward Norbert Van Den Brink, Halfweg (NL); Cornelis Adriaan De Kruif, De Bilt (NL); Jaap Goudsmit, Amsterdam (NL)

(73) Assignee: Crucell Holland B.V., Leiden (NL)

( * ) Notice: Subject to any disclaimer, the term of this patent is extended or adjusted under 35 U.S.C. 154(b) by 700 days.

This patent is subject to a terminal disclaimer.

(21) Appl. No.: 11/667,640

(22) PCT Filed: Nov. 10, 2005

(86) PCT No.: PCT/EP2005/055876

§ 371 (c)(1), (2), (4) Date: May 11, 2007

(87) PCT Pub. No.: WO2006/051091

PCT Pub. Date: May 18, 2006

(65) Prior Publication Data

US 2008/0014204 A1 Jan. 17, 2008

Related U.S. Application Data

(60) Provisional application No. 60/627,773, filed on Nov. 11, 2004.

(30) Foreign Application Priority Data

Nov. 11, 2004 (EP) .................................... 04105684
Nov. 30, 2004 (EP) .................................... 04106192
Mar. 17, 2005 (EP) .................................... 05102117
Aug. 8, 2005 (EP) .................................... 05107288

(51) Int. Cl.
*C07K 16/00* (2006.01)
*C12Q 1/00* (2006.01)
*G01N 33/563* (2006.01)

(52) U.S. Cl. ............... 530/388.8; 530/387.3; 530/388.1; 435/5; 435/7.1

(58) Field of Classification Search ........................ None
See application file for complete search history.

(56) References Cited

U.S. PATENT DOCUMENTS

| | | | | |
|---|---|---|---|---|
| 5,696,108 | A | 12/1997 | Heath, Jr. et al. | |
| 6,265,150 | B1 | 7/2001 | Terstappen et al. | |
| 7,696,330 | B2 * | 4/2010 | Meulen et al. | 530/388.8 |
| 2005/0069869 | A1 | 3/2005 | Ambrosino et al. | |
| 2005/0249739 | A1 * | 11/2005 | Marasco et al. | 424/159.1 |
| 2006/0110803 | A1 | 5/2006 | ter Meulen et al. | |
| 2006/0154243 | A1 | 7/2006 | ter Meulen et al. | |
| 2007/0128217 | A1 | 6/2007 | ter Meulen et al. | |

FOREIGN PATENT DOCUMENTS

| | | | |
|---|---|---|---|
| WO | WO 93/09872 | | 5/1993 |
| WO | WO 98/15833 | | 4/1998 |
| WO | WO 00/63403 | | 10/2000 |
| WO | WO 02/103012 | A1 | 12/2002 |
| WO | WO 03/013599 | A2 | 2/2003 |
| WO | WO 2004/111081 | A3 | 12/2004 |
| WO | WO 2005/012337 | A | 2/2005 |
| WO | WO 2005/012337 | A2 | 2/2005 |
| WO | WO 2005/012338 | A1 | 2/2005 |
| WO | WO 2005/012360 | A | 2/2005 |
| WO | WO 2005/012360 | A2 | 2/2005 |

OTHER PUBLICATIONS

Huamg LR eta l. "Evaluation of antibody responses against SARS coronaviral nucleocapsid or spike proteins by immunoblotting or ELISA" J. Med. Virol. 73:338-346, 2004. Published online May 24, 2004.*

Kashmiri SV et al. "SDR grafting—a new approach to antibody humanization." Methods, 36:25-34, 2005.*

Bost K. et al. Antibodies against peptides sequence within the HIV envelope protein crossreact with human interleukin-2 Immunological Investigations, 17(6&7):577-586, 1988.*

PCT International Preliminary Report on Patentability, PCT/EP2005/055876, dated Feb. 16, 2007.

PCT International Search Report, PCT/EP2005/055876, dated Mar. 3, 2006.

Bisht et al., Severe acute respiratory syndrome coronavirus spike protein expressed by attenuated vaccinia virus protectively immunizes mice, PNAS, Apr. 27, 2004, pp. 6641-6646, vol. 101, No. 17.

Bukreyev et al., Mucosal immunisation of African green monkeys (*Cercopithecus aethiops* ) with an attenuated parainfluenza virus expressing the SARS coronavirus spike protein for the prevention of SARS, The Lancet, Jun. 26, 2004, pp. 2122-2127, vol. 363.

Sui et al., Potent neutralization of severe acute respiratory syndrome (SARS) coronavirus by a human mAb to S1 protein that blocks receptor association, PNAS, Feb. 24, 2004, pp. 2536-2541, vol. 101, No. 8.

Berry et al., Development and characterisation of neutralising monoclonal antibody to the SARS-coronavirus, Journal of Virological Methods, 2004, pp. 87-96, vol. 120.

Tirado et al., Antibody-Dependent Enhancement of Virus Infection and Disease, Viral Immunology, 2003, pp. 69-86, vol. 16, No. 1.

Wong et al., A 193-Amino Acid Fragment of the SARS Coronavirus S Protein Efficiently Binds Angiotensin-converting Enzyme 2, The Journal of Biological Chemistry, 2004, pp. 3197-3201, vol. 279, No. 5.

Van Den Brink et al., Molecular and Biological Characterization of Human Monoclonal Antibodies Binding to the Spike and Nucleocapsid Proteins of Severe Acute Respiratory Syndrome Coronavirus, Journal of Virology, Feb. 2005, pp. 1635-1644, vol. 79, No. 3.

(Continued)

*Primary Examiner* — Bo Peng
(74) *Attorney, Agent, or Firm* — TraskBritt

(57) ABSTRACT

The present invention provides compositions of binding molecules specifically binding to a coronavirus such as SARS-CoV and capable of neutralizing an infection caused by the virus. The compositions are suitable for diagnosing, preventing and/or treating a condition resulting from a coronavirus such as SARS-CoV.

11 Claims, 11 Drawing Sheets

OTHER PUBLICATIONS

Dionyssopoulou et al., Synthetic peptides as putative therapeutic agents in transplantation medicine: application of PEPSCAN to the identification of functional sequences in the extracellular domain of the interleukin-2 receptor beta chain (IL-2Rbeta), Journal of Immunological Methods, 2000, pp. 83-95, vol. 241.

Buchholz et al., Contributions of the structural proteins of severe acute respiratory syndrome coronavirus to protective immunity, PNAS, Jun. 29, 2004, pp. 9804-9809, vol. 101, No. 26.

Cabezas et al., A structure-based approach to a synthetic vaccine for HIV-1, Biochemistry, Nov. 28, 2000, pp. 14377-14391, vol. 39, No. 47. Abstract.

Corapi et al., Localization of antigenic sites of the S glycoprotein of Feline Infectious Peritonitis Virus involved in neutralization and antibody-dependent enhancement, Journal of Virology, The American Society of Microbiology, May 1995, pp. 2858-2862, vol. 69, No. 5.

He et al., Antigenic and immunogenic characterization and recombinant baculovirus-expressed severe acute respiratory syndrome coronavirus spike protein: implication for vaccine design, J. Virol., Jun. 2006, pp. 5757-5767, vol. 80, No. 12.

Keller et al., Passive immunity in prevention and treatment of infectious diseases, Clin Microbiol. Rev., Oct. 2000, pp. 602-614, vol. 13, No. 4.

Ksiazek et al., A Novel Coronavirus Associated with Severe Acute Respiratory Syndrome, The New England Journal of Medicine, May 15, 2003, pp. 1953-1966, vol. 348, No. 20.

Li et al., The Structural Characterization and Antigenicity of the S Protein of SARS-CoV, Geno., Prot. & Bioinfo, May 2003, pp. 108-117, vol. 1, No. 2.

Lin et al., Identification of an epitope of SARS-coronavirus nucleocapsid protein, Cell Research, 2003, pp. 141-145, vol. 13, No. 3.

Marra et al., The genome sequence of the SARS-associated coronavirus, Science, May 30, 2003, pp. 1399-1404, vol. 300, No. 5624.

Mitsuki et al., A single amino acid substitution in the S1 and S2 Spike protein domains determines the neutralization escape phenotype of SARS-CoV, Microbes Infect., Jul. 2008, pp. 908-915, vol. 10, No. 8, Epub Jun. 19, 2008.

Posthumus et al., Analysis and Simulation of a Neutralizing Epitope of Transmissible Gastroenteritis Virus, Journal of Virology, Jul. 1, 1990, pp. 3304-3309, vol. 64, No. 7.

Rota et al., Characterization of a novel coronavirus associated with severe acute respiratory syndrome, Sciencexpress, May 2003, pp. 1-10, (visited Nov. 30, 2005), www.sciencexpress.org.

Thiel et al., Mechanisms and enzymes involved in SARS coronavirus genome expression, Journal of General Virology, 2003, pp. 2305-2315, vol. 84.

Ter Meulen et al., Human monoclonal antibody as prophylaxis for SARS coronavirus infection in ferrets, The Lancet, Jun. 26, 2004, pp. 2139-2141, vol. 363.

Vicenzi et al., Coronaviridae and SARS-associated Coronavirus Strain HSR1, Emerging Infectious Diseases, Mar. 2004, pp. 413-418, vol. 10, No. 3.

Weiss et al., Coronavirus pathogenesis and the emerging pathogen severe acute respiratory syndrome coronavirus, Microbiol Mol Biol Rev., pp. 635-664, vol. 69, No. 4.

Database Entrez Nucleotides, online, NCBI, Apr. 21, 2003, Monroe et al., SARS coronavirus Urbani Strain, Database accession No. AY278741.

Database EMBL, Apr. 15, 2003, He et al., SARS coronavirus TOR2 complete genome, Database accession No. AY274119.

Database EMBL, Jun. 25, 2003, Vicenzi et al., SARS coronavirus HSR 1 complete genome, Database accession No. AY323977.

Database EMBL, online, Apr. 23, 2003, SARS coronavirus Urbani, complete genome, Database accession No. AY278741.

Database WPI, Section Ch, Week 200442, AN 2004-441790, Apr. 14, 2004.

Database WPI, Section Ch, Week 200432, AN 2004-341229, Feb. 4, 2004.

Database WPI, Section Ch, Week 200478, AN 2004-083758, Nov. 25, 2004.

PCT International Search Report, PCT/EP2004\051568, dated Aug. 22, 2005.

U.S. Appl. No. 12/589,181, filed Oct. 19, 2009, Logtenberg et al., Antibody Producing Non-Human Mammals.

U.S. Appl. No. 11/977,954, filed Oct. 26, 2007, Houtzager et al., Chimaeric Phages.

U.S. Appl. No. 12/220,971, filed Jul. 29, 2008, UytdeHaag et al., Vaccines Against West Nile Virus.

U.S. Appl. No. 11/988,146, filed Dec. 27, 2007, van den Brink et al., Cell Line for Producing Coronaviruses.

U.S. Appl. No. 11/990,974, filed Feb. 21, 2008, Throsby et al., Method for Preparing Immunoglobulin Libraries.

U.S. Appl. No. 11/337,300, filed Jan. 20, 2006, ter Meulen et al., Binding Molecules Against SARS-Coronavirus and Uses Thereof.

U.S. Appl. No. 12/227,116, filed Nov. 7, 2008, Throsby et al., Human Binding Molecules Having Killing Activity Against Enterococci and Uses Thereof.

U.S. Appl. No. 12/227,029, filed Nov. 5, 2008, Throsby et al., Human Binding Molecules Having Killing Activity Against Staphylococci and Uses Thereof.

U.S. Appl. No. 12/310,812, filed Mar. 6, 2009, van den Brink et al., Human Binding Molecules Capable of Neutralizing Influenza Virus H5N1 and Uses Thereof.

U.S. Appl. No. 11/978,742, filed Oct. 29, 2007, Bakker et al., Binding Molecules Capable of Neutralizing Rabies Virus and Uses Thereof.

U.S. Appl. No. 11/980,237, filed Oct. 29, 2007, Bakker et al., Binding Molecules Capable of Neutralizing Rabies Virus and Uses Thereof.

U.S. Appl. No. 12/459,661, filed Jul. 6, 2009, Bakker et al., Binding Molecules Capable of Neutralizing Rabies Virus and Uses Thereof.

U.S. Appl. No. 12/590,973, filed Nov. 16, 2009, ter Meulen et al., Binding Molecules Against SARS-Coronavirus and Uses Thereof.

U.S. Appl. No. 12/317,508, filed Dec. 23, 2008, Pau et al., Malaria Prime/Boost Vaccines.

U.S. Appl. No. 11/919,265, filed Oct. 24, 2007, Throsby et al., Host Cell Specific Binding Molecules Capable of Neutralizing Viruses and Uses Thereof.

U.S. Appl. No. 11/922,405, filed Dec. 13, 2007, Throsby et al., Optimization of West Nile Virus Antibodies.

* cited by examiner

| | | | | | | | | |
|---|---|---|---|---|---|---|---|---|
| | | | | | **462** | | | |
| | | P | F | S | **P** | D | G | K |
| **SARS wt** | 1375- | CCT | TTC | TCC | CCT | GAT | GGC | AAA |
| | | | | | | | | |
| | | P | F | S | **L** | D | G | K |
| **E014-C06** | 1375- | CCT | TTC | TCC | C**T**T | GAT | GGC | AAA |
| **E014-C07** | 1375- | CCT | TTC | TCC | C**T**T | GAT | GGC | AAA |
| **E014-C08** | 1375- | CCT | TTC | TCC | C**T**T | GAT | GGC | AAA |
| **E014-C09** | 1375- | CCT | TTC | TCC | C**T**T | GAT | GGC | AAA |
| **E014-C10** | 1375- | CCT | TTC | TCC | C**T**T | GAT | GGC | AAA |

FIGURE 9

SEQUENCE LISTING

```
<160> NUMBER OF SEQ ID NOS: 138

<210> SEQ ID NO 1
<211> LENGTH: 9
<212> TYPE: PRT
<213> ORGANISM: Artificial sequence
<220> FEATURE:
<223> OTHER INFORMATION: HCDR3 of SC03-014

<400> SEQUENCE: 1

Gly Ile Ser Pro Phe Tyr Phe Asp Tyr
1               5


<210> SEQ ID NO 2
<211> LENGTH: 10
<212> TYPE: PRT
<213> ORGANISM: Artificial sequence
<220> FEATURE:
<223> OTHER INFORMATION: HCDR3 of SC03-022

<400> SEQUENCE: 2

Gly Ser Gly Ile Ser Thr Pro Met Asp Val
1               5                   10


<210> SEQ ID NO 3
<211> LENGTH: 366
<212> TYPE: DNA
<213> ORGANISM: Artificial sequence
<220> FEATURE:
<223> OTHER INFORMATION: Variable heavy chain of SC03-014
<220> FEATURE:
<221> NAME/KEY: CDS
<222> LOCATION: (1)..(366)
<223> OTHER INFORMATION: Variable heavy chain of SC03-014

<400> SEQUENCE: 3

atg gcc gag gtg cag ctg gtg gag tct ggg gga ggc ttg gtc cag cct       48
Met Ala Glu Val Gln Leu Val Glu Ser Gly Gly Gly Leu Val Gln Pro
1               5                   10                  15

gga ggg tcc ctg aga ctc tcc tgt gca gcc tct gga ttc acc ttc agt       96
Gly Gly Ser Leu Arg Leu Ser Cys Ala Ala Ser Gly Phe Thr Phe Ser
            20                  25                  30

gac cac tac atg gac tgg gtc cgc cag gct cca ggg aag ggg ctg gag      144
Asp His Tyr Met Asp Trp Val Arg Gln Ala Pro Gly Lys Gly Leu Glu
        35                  40                  45
```

```
tgg gtt ggc cgt act aga aac aaa gct aac agt tac acc aca gaa tac      192
Trp Val Gly Arg Thr Arg Asn Lys Ala Asn Ser Tyr Thr Thr Glu Tyr
    50                  55                  60

gcc gcg tct gtg aaa ggc aga ttc acc atc tca aga gat gat tca aag      240
Ala Ala Ser Val Lys Gly Arg Phe Thr Ile Ser Arg Asp Asp Ser Lys
65                  70                  75                  80

aac tca ctg tat ctg caa atg aac agc ctg aaa acc gag gac acg gcc      288
Asn Ser Leu Tyr Leu Gln Met Asn Ser Leu Lys Thr Glu Asp Thr Ala
                85                  90                  95

gtg tat tac tgt gca agg ggg att tcg ccg ttt tac ttt gac tac tgg      336
Val Tyr Tyr Cys Ala Arg Gly Ile Ser Pro Phe Tyr Phe Asp Tyr Trp
            100                 105                 110

ggc caa ggt acc ctg gtc acc gtc tcg agt                              366
Gly Gln Gly Thr Leu Val Thr Val Ser Ser
        115                 120


<210> SEQ ID NO 4
<211> LENGTH: 122
<212> TYPE: PRT
<213> ORGANISM: Artificial sequence
<220> FEATURE:
<223> OTHER INFORMATION: Variable heavy chain of SC03-014

<400> SEQUENCE: 4

Met Ala Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Asp His Tyr Met Asp Trp Val Arg Gln Ala Pro Gly Lys Gly Leu Glu
        35                  40                  45

Trp Val Gly Arg Thr Arg Asn Lys Ala Asn Ser Tyr Thr Thr Glu Tyr
    50                  55                  60

Ala Ala Ser Val Lys Gly Arg Phe Thr Ile Ser Arg Asp Asp Ser Lys
65                  70                  75                  80

Asn Ser Leu Tyr Leu Gln Met Asn Ser Leu Lys Thr Glu Asp Thr Ala
                85                  90                  95

Val Tyr Tyr Cys Ala Arg Gly Ile Ser Pro Phe Tyr Phe Asp Tyr Trp
            100                 105                 110

Gly Gln Gly Thr Leu Val Thr Val Ser Ser
        115                 120


<210> SEQ ID NO 5
<211> LENGTH: 363
<212> TYPE: DNA
<213> ORGANISM: Artificial sequence
<220> FEATURE:
<223> OTHER INFORMATION: Variable heavy chain of SC03-022
<220> FEATURE:
<221> NAME/KEY: CDS
<222> LOCATION: (1)..(363)
<223> OTHER INFORMATION: Variable heavy chain of SC03-022

<400> SEQUENCE: 5

atg gcc cag atg cag ctg gtg caa tct gga aca gag gtg aaa aag ccg       48
Met Ala Gln Met Gln Leu Val Gln Ser Gly Thr Glu Val Lys Lys Pro
1               5                   10                  15

ggg gag tct ctg aag atc tcc tgt aag ggt tct gga tac ggc ttt atc       96
Gly Glu Ser Leu Lys Ile Ser Cys Lys Gly Ser Gly Tyr Gly Phe Ile
            20                  25                  30

acc tac tgg atc ggc tgg gtg cgc cag atg ccc ggg aaa ggc ctg gag      144
Thr Tyr Trp Ile Gly Trp Val Arg Gln Met Pro Gly Lys Gly Leu Glu
        35                  40                  45
```

-continued

```
tgg atg ggg atc atc tat cct ggt gac tct gaa acc aga tac agc ccg      192
Trp Met Gly Ile Ile Tyr Pro Gly Asp Ser Glu Thr Arg Tyr Ser Pro
    50                  55                  60

tcc ttc caa ggc cag gtc acc atc tca gcc gac aag tcc atc aac acc      240
Ser Phe Gln Gly Gln Val Thr Ile Ser Ala Asp Lys Ser Ile Asn Thr
65                  70                  75                  80

gcc tac ctg cag tgg agc agc ctg aag gcc tcg gac acc gcc ata tat      288
Ala Tyr Leu Gln Trp Ser Ser Leu Lys Ala Ser Asp Thr Ala Ile Tyr
                85                  90                  95

tac tgt gcg ggg ggt tcg ggg att tct acc cct atg gac gtc tgg ggc      336
Tyr Cys Ala Gly Gly Ser Gly Ile Ser Thr Pro Met Asp Val Trp Gly
            100                 105                 110

caa ggg acc acg gtc acc gtc tcg agc                                  363
Gln Gly Thr Thr Val Thr Val Ser Ser
        115                 120


<210> SEQ ID NO 6
<211> LENGTH: 121
<212> TYPE: PRT
<213> ORGANISM: Artificial sequence
<220> FEATURE:
<223> OTHER INFORMATION: Variable heavy chain of SC03-022

<400> SEQUENCE: 6

Met Ala Gln Met Gln Leu Val Gln Ser Gly Thr Glu Val Lys Lys Pro
1               5                   10                  15

Gly Glu Ser Leu Lys Ile Ser Cys Lys Gly Ser Gly Tyr Gly Phe Ile
            20                  25                  30

Thr Tyr Trp Ile Gly Trp Val Arg Gln Met Pro Gly Lys Gly Leu Glu
        35                  40                  45

Trp Met Gly Ile Ile Tyr Pro Gly Asp Ser Glu Thr Arg Tyr Ser Pro
    50                  55                  60

Ser Phe Gln Gly Gln Val Thr Ile Ser Ala Asp Lys Ser Ile Asn Thr
65                  70                  75                  80

Ala Tyr Leu Gln Trp Ser Ser Leu Lys Ala Ser Asp Thr Ala Ile Tyr
                85                  90                  95

Tyr Cys Ala Gly Gly Ser Gly Ile Ser Thr Pro Met Asp Val Trp Gly
            100                 105                 110

Gln Gly Thr Thr Val Thr Val Ser Ser
        115                 120


<210> SEQ ID NO 7
<211> LENGTH: 318
<212> TYPE: DNA
<213> ORGANISM: Artificial sequence
<220> FEATURE:
<223> OTHER INFORMATION: Variable light chain of SC03-014
<220> FEATURE:
<221> NAME/KEY: CDS
<222> LOCATION: (1)..(318)
<223> OTHER INFORMATION: Variable light chain of SC03-014

<400> SEQUENCE: 7

gag ctc acc cag tct cca tcc tcc ctg tct gca tct gta gga gac aga       48
Glu Leu Thr Gln Ser Pro Ser Ser Leu Ser Ala Ser Val Gly Asp Arg
1               5                   10                  15

gtc acc atc act tgc cgg gca agt cag agc att agc agc tac tta aat       96
Val Thr Ile Thr Cys Arg Ala Ser Gln Ser Ile Ser Ser Tyr Leu Asn
            20                  25                  30

tgg tat cag cag aaa cca ggg aaa gcc cct aag ctc ctg atc tat gct      144
Trp Tyr Gln Gln Lys Pro Gly Lys Ala Pro Lys Leu Leu Ile Tyr Ala
        35                  40                  45
```

-continued

```
gca tcc agt ttg caa agt ggg gtc cca tca agg ttc agt ggc agt gga      192
Ala Ser Ser Leu Gln Ser Gly Val Pro Ser Arg Phe Ser Gly Ser Gly
    50                  55                  60

tct ggg aca gat ttc act ctc acc atc agc agt ctg caa cct gaa gat      240
Ser Gly Thr Asp Phe Thr Leu Thr Ile Ser Ser Leu Gln Pro Glu Asp
65                  70                  75                  80

ttt gca act tac tac tgt caa cag agt tac agt acc cct cca acg ttc      288
Phe Ala Thr Tyr Tyr Cys Gln Gln Ser Tyr Ser Thr Pro Pro Thr Phe
                85                  90                  95

ggc caa ggg acc aag gtg gag atc aaa cgt                              318
Gly Gln Gly Thr Lys Val Glu Ile Lys Arg
            100                 105


<210> SEQ ID NO 8
<211> LENGTH: 106
<212> TYPE: PRT
<213> ORGANISM: Artificial sequence
<220> FEATURE:
<223> OTHER INFORMATION: Variable light chain of SC03-014

<400> SEQUENCE: 8

Glu Leu Thr Gln Ser Pro Ser Ser Leu Ser Ala Ser Val Gly Asp Arg
1               5                   10                  15

Val Thr Ile Thr Cys Arg Ala Ser Gln Ser Ile Ser Ser Tyr Leu Asn
            20                  25                  30

Trp Tyr Gln Gln Lys Pro Gly Lys Ala Pro Lys Leu Leu Ile Tyr Ala
        35                  40                  45

Ala Ser Ser Leu Gln Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Thr Tyr Tyr Cys Gln Gln Ser Tyr Ser Thr Pro Pro Thr Phe
                85                  90                  95

Gly Gln Gly Thr Lys Val Glu Ile Lys Arg
            100                 105


<210> SEQ ID NO 9
<211> LENGTH: 348
<212> TYPE: DNA
<213> ORGANISM: Artificial sequence
<220> FEATURE:
<223> OTHER INFORMATION: Variable light chain of SC03-022
<220> FEATURE:
<221> NAME/KEY: CDS
<222> LOCATION: (1)..(348)
<223> OTHER INFORMATION: Variable light chain of SC03-022

<400> SEQUENCE: 9

gac atc cag ttg acc cag tct cca gac tcc ctg gct gtg tct ctg ggc       48
Asp Ile Gln Leu Thr Gln Ser Pro Asp Ser Leu Ala Val Ser Leu Gly
1               5                   10                  15

gag agg gcc acc atc aac tgc aag tcc agc cag agt gtt tta tac agc       96
Glu Arg Ala Thr Ile Asn Cys Lys Ser Ser Gln Ser Val Leu Tyr Ser
            20                  25                  30

tcc atc aat aag aac tac tta gct tgg tac cag cag aaa cca gga cag      144
Ser Ile Asn Lys Asn Tyr Leu Ala Trp Tyr Gln Gln Lys Pro Gly Gln
        35                  40                  45

cct cct aag ctg ctc att tac tgg gca tct acc cgg gaa tcc ggg gtc      192
Pro Pro Lys Leu Leu Ile Tyr Trp Ala Ser Thr Arg Glu Ser Gly Val
    50                  55                  60

cct gac cga ttc agt ggc agc ggg tct ggg aca gat ttc act ctc acc      240
Pro Asp Arg Phe Ser Gly Ser Gly Ser Gly Thr Asp Phe Thr Leu Thr
```

```
65                  70                  75                  80

atc agc agc ctg cag gct gaa gat gtg gca gtt tat tac tgt cag caa      288
Ile Ser Ser Leu Gln Ala Glu Asp Val Ala Val Tyr Tyr Cys Gln Gln
                85                  90                  95

tat tat agt act ccg tac act ttt ggc cag ggg acc aag gtg gaa atc      336
Tyr Tyr Ser Thr Pro Tyr Thr Phe Gly Gln Gly Thr Lys Val Glu Ile
            100                 105                 110

aaa cgt gcg gcc                                                      348
Lys Arg Ala Ala
        115


<210> SEQ ID NO 10
<211> LENGTH: 116
<212> TYPE: PRT
<213> ORGANISM: Artificial sequence
<220> FEATURE:
<223> OTHER INFORMATION: Variable light chain of SC03-022

<400> SEQUENCE: 10

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ile Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys Arg Ala Ala
        115


<210> SEQ ID NO 11
<211> LENGTH: 23
<212> TYPE: DNA
<213> ORGANISM: Artificial sequence
<220> FEATURE:
<223> OTHER INFORMATION: Primer HuVH1B/7A

<400> SEQUENCE: 11

cagrtgcagc tggtgcartc tgg                                             23


<210> SEQ ID NO 12
<211> LENGTH: 23
<212> TYPE: DNA
<213> ORGANISM: Artificial sequence
<220> FEATURE:
<223> OTHER INFORMATION: Primer HuVH1C

<400> SEQUENCE: 12

saggtccagc tggtrcagtc tgg                                             23


<210> SEQ ID NO 13
<211> LENGTH: 23
<212> TYPE: DNA
<213> ORGANISM: Artificial sequence
<220> FEATURE:
<223> OTHER INFORMATION: Primer HuVH2B
```

-continued

<400> SEQUENCE: 13
saggtgcagc tggtggagtc tgg 23

<210> SEQ ID NO 14
<211> LENGTH: 23
<212> TYPE: DNA
<213> ORGANISM: Artificial sequence
<220> FEATURE:
<223> OTHER INFORMATION: Primer HuVH3B

<400> SEQUENCE: 14
saggtgcagc tggtggagtc tgg 23

<210> SEQ ID NO 15
<211> LENGTH: 23
<212> TYPE: DNA
<213> ORGANISM: Artificial sequence
<220> FEATURE:
<223> OTHER INFORMATION: Primer HuVH3C

<400> SEQUENCE: 15
gaggtgcagc tggtggagwc ygg 23

<210> SEQ ID NO 16
<211> LENGTH: 23
<212> TYPE: DNA
<213> ORGANISM: Artificial sequence
<220> FEATURE:
<223> OTHER INFORMATION: Primer HuVH4B

<400> SEQUENCE: 16
caggtgcagc tacagcagtg ggg 23

<210> SEQ ID NO 17
<211> LENGTH: 23
<212> TYPE: DNA
<213> ORGANISM: Artificial sequence
<220> FEATURE:
<223> OTHER INFORMATION: Primer HuVH4C

<400> SEQUENCE: 17
cagstgcagc tgcaggagtc sgg 23

<210> SEQ ID NO 18
<211> LENGTH: 23
<212> TYPE: DNA
<213> ORGANISM: Artificial sequence
<220> FEATURE:
<223> OTHER INFORMATION: Primer HuVH5B

<400> SEQUENCE: 18
gargtgcagc tggtgcagtc tgg 23

<210> SEQ ID NO 19
<211> LENGTH: 23
<212> TYPE: DNA
<213> ORGANISM: Artificial sequence
<220> FEATURE:
<223> OTHER INFORMATION: Primer HuVH6A

<400> SEQUENCE: 19
caggtacagc tgcagcagtc agg 23

<210> SEQ ID NO 20
<211> LENGTH: 24
<212> TYPE: DNA

<213> ORGANISM: Artificial sequence
<220> FEATURE:
<223> OTHER INFORMATION: Primer HuJH1/2

<400> SEQUENCE: 20
tgaggagacg gtgaccaggg tgcc 24

<210> SEQ ID NO 21
<211> LENGTH: 24
<212> TYPE: DNA
<213> ORGANISM: Artificial sequence
<220> FEATURE:
<223> OTHER INFORMATION: Primer HuJH3

<400> SEQUENCE: 21
tgaagagacg gtgaccattg tccc 24

<210> SEQ ID NO 22
<211> LENGTH: 24
<212> TYPE: DNA
<213> ORGANISM: Artificial sequence
<220> FEATURE:
<223> OTHER INFORMATION: Primer HuJH4/5

<400> SEQUENCE: 22
tgaggagacg gtgaccaggg ttcc 24

<210> SEQ ID NO 23
<211> LENGTH: 24
<212> TYPE: DNA
<213> ORGANISM: Artificial sequence
<220> FEATURE:
<223> OTHER INFORMATION: Primer HuJH6

<400> SEQUENCE: 23
tgaggagacg gtgaccgtgg tccc 24

<210> SEQ ID NO 24
<211> LENGTH: 56
<212> TYPE: DNA
<213> ORGANISM: Artificial sequence
<220> FEATURE:
<223> OTHER INFORMATION: Primer HuVH1B/7A-NcoI

<400> SEQUENCE: 24
gtcctcgcaa ctgcggccca gccggccatg gcccagrtgc agctggtgca rtctgg 56

<210> SEQ ID NO 25
<211> LENGTH: 56
<212> TYPE: DNA
<213> ORGANISM: Artificial sequence
<220> FEATURE:
<223> OTHER INFORMATION: Primer HuVH1C-NcoI

<400> SEQUENCE: 25
gtcctcgcaa ctgcggccca gccggccatg gccsaggtcc agctggtrca gtctgg 56

<210> SEQ ID NO 26
<211> LENGTH: 56
<212> TYPE: DNA
<213> ORGANISM: Artificial sequence
<220> FEATURE:
<223> OTHER INFORMATION: Primer HuVH2B-NcoI

<400> SEQUENCE: 26
gtcctcgcaa ctgcggccca gccggccatg gcccagrtca ccttgaagga gtctgg 56

<210> SEQ ID NO 27
<211> LENGTH: 56
<212> TYPE: DNA
<213> ORGANISM: Artificial sequence
<220> FEATURE:
<223> OTHER INFORMATION: Primer HuVH3B-NcoI

<400> SEQUENCE: 27
gtcctcgcaa ctgcggccca gccggccatg gccsaggtgc agctggtgga gtctgg 56

<210> SEQ ID NO 28
<211> LENGTH: 56
<212> TYPE: DNA
<213> ORGANISM: Artificial sequence
<220> FEATURE:
<223> OTHER INFORMATION: Primer HuVH3C-NcoI

<400> SEQUENCE: 28
gtcctcgcaa ctgcggccca gccggccatg gccgaggtgc agctggtgga gwcygg 56

<210> SEQ ID NO 29
<211> LENGTH: 56
<212> TYPE: DNA
<213> ORGANISM: Artificial sequence
<220> FEATURE:
<223> OTHER INFORMATION: Primer HuVH4B-NcoI

<400> SEQUENCE: 29
gtcctcgcaa ctgcggccca gccggccatg gcccaggtgc agctacagca gtgggg 56

<210> SEQ ID NO 30
<211> LENGTH: 56
<212> TYPE: DNA
<213> ORGANISM: Artificial sequence
<220> FEATURE:
<223> OTHER INFORMATION: Primer HuVH4C-NcoI

<400> SEQUENCE: 30
gtcctcgcaa ctgcggccca gccggccatg gcccagstgc agctgcagga gtcsgg 56

<210> SEQ ID NO 31
<211> LENGTH: 56
<212> TYPE: DNA
<213> ORGANISM: Artificial sequence
<220> FEATURE:
<223> OTHER INFORMATION: Primer HuVH5B-NcoI

<400> SEQUENCE: 31
gtcctcgcaa ctgcggccca gccggccatg gccgargtgc agctggtgca gtctgg 56

<210> SEQ ID NO 32
<211> LENGTH: 56
<212> TYPE: DNA
<213> ORGANISM: Artificial sequence
<220> FEATURE:
<223> OTHER INFORMATION: Primer HuVH6A-NcoI

<400> SEQUENCE: 32
gtcctcgcaa ctgcggccca gccggccatg gcccaggtac agctgcagca gtcagg 56

<210> SEQ ID NO 33
<211> LENGTH: 36
<212> TYPE: DNA
<213> ORGANISM: Artificial sequence
<220> FEATURE:
<223> OTHER INFORMATION: Primer HuJH1/2-XhoI

<400> SEQUENCE: 33
gagtcattct cgactcgaga cggtgaccag ggtgcc 36

<210> SEQ ID NO 34
<211> LENGTH: 36
<212> TYPE: DNA
<213> ORGANISM: Artificial sequence
<220> FEATURE:
<223> OTHER INFORMATION: Primer HuJH3-XhoI

<400> SEQUENCE: 34
gagtcattct cgactcgaga cggtgaccat tgtccc 36

<210> SEQ ID NO 35
<211> LENGTH: 36
<212> TYPE: DNA
<213> ORGANISM: Artificial sequence
<220> FEATURE:
<223> OTHER INFORMATION: Primer HuJH4/5-XhoI

<400> SEQUENCE: 35
gagtcattct cgactcgaga cggtgaccag ggttcc 36

<210> SEQ ID NO 36
<211> LENGTH: 36
<212> TYPE: DNA
<213> ORGANISM: Artificial sequence
<220> FEATURE:
<223> OTHER INFORMATION: Primer HuJH6-XhoI

<400> SEQUENCE: 36
gagtcattct cgactcgaga cggtgaccgt ggtccc 36

<210> SEQ ID NO 37
<211> LENGTH: 23
<212> TYPE: DNA
<213> ORGANISM: Artificial sequence
<220> FEATURE:
<223> OTHER INFORMATION: Primer HuVlambda1A

<400> SEQUENCE: 37
cagtctgtgc tgactcagcc acc 23

<210> SEQ ID NO 38
<211> LENGTH: 23
<212> TYPE: DNA
<213> ORGANISM: Artificial sequence
<220> FEATURE:
<223> OTHER INFORMATION: Primer HuVlambda1B

<400> SEQUENCE: 38
cagtctgtgy tgacgcagcc gcc 23

<210> SEQ ID NO 39
<211> LENGTH: 23
<212> TYPE: DNA
<213> ORGANISM: Artificial sequence
<220> FEATURE:
<223> OTHER INFORMATION: Primer HuVlambda1C

<400> SEQUENCE: 39
cagtctgtcg tgacgcagcc gcc 23

<210> SEQ ID NO 40
<211> LENGTH: 21
<212> TYPE: DNA

<213> ORGANISM: Artificial sequence
<220> FEATURE:
<223> OTHER INFORMATION: Primer HuVlambda2

<400> SEQUENCE: 40
cartctgccc tgactcagcc t 21

<210> SEQ ID NO 41
<211> LENGTH: 23
<212> TYPE: DNA
<213> ORGANISM: Artificial sequence
<220> FEATURE:
<223> OTHER INFORMATION: Primer HuVlambda3A

<400> SEQUENCE: 41
tcctatgwgc tgactcagcc acc 23

<210> SEQ ID NO 42
<211> LENGTH: 23
<212> TYPE: DNA
<213> ORGANISM: Artificial sequence
<220> FEATURE:
<223> OTHER INFORMATION: Primer HuVlambda3B

<400> SEQUENCE: 42
tcttctgagc tgactcagga ccc 23

<210> SEQ ID NO 43
<211> LENGTH: 23
<212> TYPE: DNA
<213> ORGANISM: Artificial sequence
<220> FEATURE:
<223> OTHER INFORMATION: Primer HuVlambda4

<400> SEQUENCE: 43
cacgttatac tgactcaacc gcc 23

<210> SEQ ID NO 44
<211> LENGTH: 23
<212> TYPE: DNA
<213> ORGANISM: Artificial sequence
<220> FEATURE:
<223> OTHER INFORMATION: Primer HuVlambda5

<400> SEQUENCE: 44
caggctgtgc tgactcagcc gtc 23

<210> SEQ ID NO 45
<211> LENGTH: 23
<212> TYPE: DNA
<213> ORGANISM: Artificial sequence
<220> FEATURE:
<223> OTHER INFORMATION: Primer HuVlambda6

<400> SEQUENCE: 45
aattttatgc tgactcagcc cca 23

<210> SEQ ID NO 46
<211> LENGTH: 23
<212> TYPE: DNA
<213> ORGANISM: Artificial sequence
<220> FEATURE:
<223> OTHER INFORMATION: Primer HuVlambda7/8

<400> SEQUENCE: 46
cagrctgtgg tgacycagga gcc 23

<210> SEQ ID NO 47
<211> LENGTH: 23
<212> TYPE: DNA
<213> ORGANISM: Artificial sequence
<220> FEATURE:
<223> OTHER INFORMATION: Primer HuVlambda9

<400> SEQUENCE: 47
cwgcctgtgc tgactcagcc mcc 23

<210> SEQ ID NO 48
<211> LENGTH: 23
<212> TYPE: DNA
<213> ORGANISM: Artificial sequence
<220> FEATURE:
<223> OTHER INFORMATION: Primer HuVkappa1B

<400> SEQUENCE: 48
gacatccagw tgacccagtc tcc 23

<210> SEQ ID NO 49
<211> LENGTH: 23
<212> TYPE: DNA
<213> ORGANISM: Artificial sequence
<220> FEATURE:
<223> OTHER INFORMATION: Primer HuVkappa2

<400> SEQUENCE: 49
gatgttgtga tgactcagtc tcc 23

<210> SEQ ID NO 50
<211> LENGTH: 23
<212> TYPE: DNA
<213> ORGANISM: Artificial sequence
<220> FEATURE:
<223> OTHER INFORMATION: Primer HuVkappa3

<400> SEQUENCE: 50
gaaattgtgw tgacrcagtc tcc 23

<210> SEQ ID NO 51
<211> LENGTH: 23
<212> TYPE: DNA
<213> ORGANISM: Artificial sequence
<220> FEATURE:
<223> OTHER INFORMATION: Primer HuVkappa4

<400> SEQUENCE: 51
gatattgtga tgacccacac tcc 23

<210> SEQ ID NO 52
<211> LENGTH: 23
<212> TYPE: DNA
<213> ORGANISM: Artificial sequence
<220> FEATURE:
<223> OTHER INFORMATION: Primer HuVkappa5

<400> SEQUENCE: 52
gaaacgacac tcacgcagtc tcc 23

<210> SEQ ID NO 53
<211> LENGTH: 23
<212> TYPE: DNA
<213> ORGANISM: Artificial sequence
<220> FEATURE:
<223> OTHER INFORMATION: Primer HuVkappa6

<400> SEQUENCE: 53
gaaattgtgc tgactcagtc tcc 23

<210> SEQ ID NO 54
<211> LENGTH: 24
<212> TYPE: DNA
<213> ORGANISM: Artificial sequence
<220> FEATURE:
<223> OTHER INFORMATION: Primer HuJlambda1

<400> SEQUENCE: 54
acctaggacg gtgaccttgg tccc 24

<210> SEQ ID NO 55
<211> LENGTH: 24
<212> TYPE: DNA
<213> ORGANISM: Artificial sequence
<220> FEATURE:
<223> OTHER INFORMATION: Primer HuJlambda2/3

<400> SEQUENCE: 55
acctaggacg gtcagcttgg tccc 24

<210> SEQ ID NO 56
<211> LENGTH: 24
<212> TYPE: DNA
<213> ORGANISM: Artificial sequence
<220> FEATURE:
<223> OTHER INFORMATION: Primer HuJlambda4/5

<400> SEQUENCE: 56
acytaaaacg gtgagctggg tccc 24

<210> SEQ ID NO 57
<211> LENGTH: 24
<212> TYPE: DNA
<213> ORGANISM: Artificial sequence
<220> FEATURE:
<223> OTHER INFORMATION: Primer HuJkappa1

<400> SEQUENCE: 57
acgtttgatt tccaccttgg tccc 24

<210> SEQ ID NO 58
<211> LENGTH: 24
<212> TYPE: DNA
<213> ORGANISM: Artificial sequence
<220> FEATURE:
<223> OTHER INFORMATION: Primer HuJkappa2

<400> SEQUENCE: 58
acgtttgatc tccagcttgg tccc 24

<210> SEQ ID NO 59
<211> LENGTH: 24
<212> TYPE: DNA
<213> ORGANISM: Artificial sequence
<220> FEATURE:
<223> OTHER INFORMATION: Primer HuJkappa3

<400> SEQUENCE: 59
acgtttgata tccactttgg tccc 24

<210> SEQ ID NO 60
<211> LENGTH: 24
<212> TYPE: DNA

<213> ORGANISM: Artificial sequence
<220> FEATURE:
<223> OTHER INFORMATION: Primer HuJkappa4

<400> SEQUENCE: 60
acgtttgatc tccaccttgg tccc 24

<210> SEQ ID NO 61
<211> LENGTH: 24
<212> TYPE: DNA
<213> ORGANISM: Artificial sequence
<220> FEATURE:
<223> OTHER INFORMATION: Primer HuJkappa5

<400> SEQUENCE: 61
acgtttaatc tccagtcgtg tccc 24

<210> SEQ ID NO 62
<211> LENGTH: 41
<212> TYPE: DNA
<213> ORGANISM: Artificial sequence
<220> FEATURE:
<223> OTHER INFORMATION: Primer HuVkappa1B-SalI

<400> SEQUENCE: 62
tgagcacaca ggtcgacgga catccagwtg acccagtctc c 41

<210> SEQ ID NO 63
<211> LENGTH: 41
<212> TYPE: DNA
<213> ORGANISM: Artificial sequence
<220> FEATURE:
<223> OTHER INFORMATION: Primer HuVkappa2-SalI

<400> SEQUENCE: 63
tgagcacaca ggtcgacgga tgttgtgatg actcagtctc c 41

<210> SEQ ID NO 64
<211> LENGTH: 41
<212> TYPE: DNA
<213> ORGANISM: Artificial sequence
<220> FEATURE:
<223> OTHER INFORMATION: Primer HuVkappa3B-SalI

<400> SEQUENCE: 64
tgagcacaca ggtcgacgga aattgtgwtg acrcagtctc c 41

<210> SEQ ID NO 65
<211> LENGTH: 41
<212> TYPE: DNA
<213> ORGANISM: Artificial sequence
<220> FEATURE:
<223> OTHER INFORMATION: Primer HuVkappa4B-SalI

<400> SEQUENCE: 65
tgagcacaca ggtcgacgga tattgtgatg acccacactc c 41

<210> SEQ ID NO 66
<211> LENGTH: 41
<212> TYPE: DNA
<213> ORGANISM: Artificial sequence
<220> FEATURE:
<223> OTHER INFORMATION: Primer HuVkappa5-SalI

<400> SEQUENCE: 66
tgagcacaca ggtcgacgga aacgacactc acgcagtctc c 41

<210> SEQ ID NO 67
<211> LENGTH: 41
<212> TYPE: DNA
<213> ORGANISM: Artificial sequence
<220> FEATURE:
<223> OTHER INFORMATION: Primer HuVkappa6-SalI

<400> SEQUENCE: 67
tgagcacaca ggtcgacgga aattgtgctg actcagtctc c 41

<210> SEQ ID NO 68
<211> LENGTH: 48
<212> TYPE: DNA
<213> ORGANISM: Artificial sequence
<220> FEATURE:
<223> OTHER INFORMATION: Primer HuJkappa1-NotI

<400> SEQUENCE: 68
gagtcattct cgacttgcgg ccgcacgttt gatttccacc ttggtccc 48

<210> SEQ ID NO 69
<211> LENGTH: 48
<212> TYPE: DNA
<213> ORGANISM: Artificial sequence
<220> FEATURE:
<223> OTHER INFORMATION: Primer HuJkappa2-NotI

<400> SEQUENCE: 69
gagtcattct cgacttgcgg ccgcacgttt gatctccagc ttggtccc 48

<210> SEQ ID NO 70
<211> LENGTH: 48
<212> TYPE: DNA
<213> ORGANISM: Artificial sequence
<220> FEATURE:
<223> OTHER INFORMATION: Primer HuJkappa3-NotI

<400> SEQUENCE: 70
gagtcattct cgacttgcgg ccgcacgttt gatatccact ttggtccc 48

<210> SEQ ID NO 71
<211> LENGTH: 48
<212> TYPE: DNA
<213> ORGANISM: Artificial sequence
<220> FEATURE:
<223> OTHER INFORMATION: Primer HuJkappa4-NotI

<400> SEQUENCE: 71
gagtcattct cgacttgcgg ccgcacgttt gatctccacc ttggtccc 48

<210> SEQ ID NO 72
<211> LENGTH: 48
<212> TYPE: DNA
<213> ORGANISM: Artificial sequence
<220> FEATURE:
<223> OTHER INFORMATION: Primer HuJ?kappa5-NotI

<400> SEQUENCE: 72
gagtcattct cgacttgcgg ccgcacgttt aatctccagt cgtgtccc 48

<210> SEQ ID NO 73
<211> LENGTH: 41
<212> TYPE: DNA
<213> ORGANISM: Artificial sequence
<220> FEATURE:
<223> OTHER INFORMATION: Primer HuVlambda1A-SalI

<400> SEQUENCE: 73
tgagcacaca ggtcgacgca gtctgtgctg actcagccac c 41

<210> SEQ ID NO 74
<211> LENGTH: 41
<212> TYPE: DNA
<213> ORGANISM: Artificial sequence
<220> FEATURE:
<223> OTHER INFORMATION: Primer HuVlambda1B-SalI

<400> SEQUENCE: 74
tgagcacaca ggtcgacgca gtctgtgytg acgcagccgc c 41

<210> SEQ ID NO 75
<211> LENGTH: 41
<212> TYPE: DNA
<213> ORGANISM: Artificial sequence
<220> FEATURE:
<223> OTHER INFORMATION: Primer HuVlambda1C-SalI

<400> SEQUENCE: 75
tgagcacaca ggtcgacgca gtctgtcgtg acgcagccgc c 41

<210> SEQ ID NO 76
<211> LENGTH: 39
<212> TYPE: DNA
<213> ORGANISM: Artificial sequence
<220> FEATURE:
<223> OTHER INFORMATION: Primer HuVlambda2-SalI

<400> SEQUENCE: 76
tgagcacaca ggtcgacgca rtctgccctg actcagcct 39

<210> SEQ ID NO 77
<211> LENGTH: 41
<212> TYPE: DNA
<213> ORGANISM: Artificial sequence
<220> FEATURE:
<223> OTHER INFORMATION: Primer HuVlambda3A-SalI

<400> SEQUENCE: 77
tgagcacaca ggtcgacgtc ctatgwgctg actcagccac c 41

<210> SEQ ID NO 78
<211> LENGTH: 41
<212> TYPE: DNA
<213> ORGANISM: Artificial sequence
<220> FEATURE:
<223> OTHER INFORMATION: Primer HuVlambda3B-SalI

<400> SEQUENCE: 78
tgagcacaca ggtcgacgtc ttctgagctg actcaggacc c 41

<210> SEQ ID NO 79
<211> LENGTH: 41
<212> TYPE: DNA
<213> ORGANISM: Artificial sequence
<220> FEATURE:
<223> OTHER INFORMATION: Primer HuVlambda4-SalI

<400> SEQUENCE: 79
tgagcacaca ggtcgacgca cgttatactg actcaaccgc c 41

<210> SEQ ID NO 80
<211> LENGTH: 41
<212> TYPE: DNA

<213> ORGANISM: Artificial sequence
<220> FEATURE:
<223> OTHER INFORMATION: Primer HuVlambda5-SalI

<400> SEQUENCE: 80
tgagcacaca ggtcgacgca ggctgtgctg actcagccgt c 41

<210> SEQ ID NO 81
<211> LENGTH: 41
<212> TYPE: DNA
<213> ORGANISM: Artificial sequence
<220> FEATURE:
<223> OTHER INFORMATION: Primer HuVlambda6-SalI

<400> SEQUENCE: 81
tgagcacaca ggtcgacgaa ttttatgctg actcagcccc a 41

<210> SEQ ID NO 82
<211> LENGTH: 41
<212> TYPE: DNA
<213> ORGANISM: Artificial sequence
<220> FEATURE:
<223> OTHER INFORMATION: Primer HuVlambda7/8-SalI

<400> SEQUENCE: 82
tgagcacaca ggtcgacgca grctgtggtg acycaggagc c 41

<210> SEQ ID NO 83
<211> LENGTH: 41
<212> TYPE: DNA
<213> ORGANISM: Artificial sequence
<220> FEATURE:
<223> OTHER INFORMATION: Primer HuVlambda9-SalI

<400> SEQUENCE: 83
tgagcacaca ggtcgacgcw gcctgtgctg actcagccmc c 41

<210> SEQ ID NO 84
<211> LENGTH: 48
<212> TYPE: DNA
<213> ORGANISM: Artificial sequence
<220> FEATURE:
<223> OTHER INFORMATION: Primer HuJlambda1-NotI

<400> SEQUENCE: 84
gagtcattct cgacttgcgg ccgcacctag gacggtgacc ttggtccc 48

<210> SEQ ID NO 85
<211> LENGTH: 48
<212> TYPE: DNA
<213> ORGANISM: Artificial sequence
<220> FEATURE:
<223> OTHER INFORMATION: Primer HuJlambda2/3-NotI

<400> SEQUENCE: 85
gagtcattct cgacttgcgg ccgcacctag gacggtcagc ttggtccc 48

<210> SEQ ID NO 86
<211> LENGTH: 48
<212> TYPE: DNA
<213> ORGANISM: Artificial sequence
<220> FEATURE:
<223> OTHER INFORMATION: Primer HuJlambda4/5-NotI

<400> SEQUENCE: 86
gagtcattct cgacttgcgg ccgcacytaa aacggtgagc tgggtccc 48

<210> SEQ ID NO 87
<211> LENGTH: 24
<212> TYPE: DNA
<213> ORGANISM: Artificial sequence
<220> FEATURE:
<223> OTHER INFORMATION: Primer HuCIgG

<400> SEQUENCE: 87
gtccaccttg gtgttgctgg gctt 24

<210> SEQ ID NO 88
<211> LENGTH: 4914
<212> TYPE: DNA
<213> ORGANISM: Artificial sequence
<220> FEATURE:
<223> OTHER INFORMATION: Vector pDV-C05

<400> SEQUENCE: 88
aagcttgcat gcaaattcta tttcaaggag acagtcataa tgaaatacct attgcctacg 60
gcagccgctg gattgttatt actcgcggcc cagccggcca tggccgaggt gtttgactaa 120
tggggcgcgc ctcagggaac cctggtcacc gtctcgagcg gtacgggcgg ttcaggcgga 180
accggcagcg gcactggcgg gtcgacggaa attgtgctca cacagtctcc agccaccctg 240
tctttgtctc caggggaaag agccaccctc tcctgcaggg ccagtcagag tgttagcagc 300
tacttagcct ggtaccaaca gaaacctggc caggctccca ggctcctcat ctatgatgca 360
tccaacaggg ccactggcat cccagccagg ttcagtggca gtgggtctgg gacagacttc 420
actctcacca tcagcagcct agagcctgaa gattttgcag tttattactg tcagcagcgt 480
agcaactggc ctccggcttt cggcggaggg accaaggtgg agatcaaacg tgcggccgca 540
tataccgata ttgaaatgaa ccgcctgggc aaaggggccg catagactgt tgaaagttgt 600
ttagcaaaac ctcatacaga aaattcattt actaacgtct ggaaagacga caaaacttta 660
gatcgttacg ctaactatga gggctgtctg tggaatgcta caggcgttgt ggtttgtact 720
ggtgacgaaa ctcagtgtta cggtacatgg gttcctattg ggcttgctat ccctgaaaat 780
gagggtggtg gctctgaggg tggcggttct gagggtggcg gttctgaggg tggcggtact 840
aaacctcctg agtacggtga tacacctatt ccgggctata cttatatcaa ccctctcgac 900
ggcacttatc cgcctggtac tgagcaaaac cccgctaatc ctaatccttc tcttgaggag 960
tctcagcctc ttaatacttt catgtttcag aataataggt tccgaaatag gcagggtgca 1020
ttaactgttt atacgggcac tgttactcaa ggcactgacc ccgttaaaac ttattaccag 1080
tacactcctg tatcatcaaa agccatgtat gacgcttact ggaacggtaa attcagagac 1140
tgcgctttcc attctggctt taatgaggat ccattcgttt gtgaatatca aggccaatcg 1200
tctgacctgc ctcaacctcc tgtcaatgct ggcggcggct ctggtggtgg ttctggtggc 1260
ggctctgagg gtggcggctc tgagggtggc ggttctgagg gtggcggctc tgagggtggc 1320
ggttccggtg gcggctccgg ttccggtgat tttgattatg aaaaaatggc aaacgctaat 1380
aagggggcta tgaccgaaaa tgccgatgaa aacgcgctac agtctgacgc taaaggcaaa 1440
cttgattctg tcgctactga ttacggtgct gctatcgatg gtttcattgg tgacgtttcc 1500
ggccttgcta atggtaatgg tgctactggt gattttgctg gctctaattc ccaaatggct 1560
caagtcggtg acggtgataa ttcaccttta atgaataatt tccgtcaata tttaccttct 1620
ttgcctcagt cggttgaatg tcgcccttat gtctttggcg ctggtaaacc atatgaattt 1680
tctattgatt gtgacaaaat aaacttattc cgtggtgtct ttgcgtttct tttatatgtt 1740

-continued gccaccttta tgtatgtatt ttcgacgttt gctaacatac tgcgtaataa ggagtcttaa 1800
taagaattca ctggccgtcg ttttacaacg tcgtgactgg gaaaaccctg gcgttaccca 1860
acttaatcgc cttgcagcac atccccctt cgccagctgg cgtaatagcg aagaggcccg 1920
caccgatcgc ccttcccaac agttgcgcag cctgaatggc gaatggcgcc tgatgcggta 1980
ttttctcctt acgcatctgt gcggtatttc acaccgcata cgtcaaagca accatagtac 2040
gcgccctgta gcggcgcatt aagcgcggcg ggtgtggtgg ttacgcgcag cgtgaccgct 2100
acacttgcca gcgccctagc gcccgctcct ttcgctttct tcccttcctt tctcgccacg 2160
ttcgccggct ttccccgtca agctctaaat cgggggctcc ctttagggtt ccgatttagt 2220
gctttacggc acctcgaccc caaaaaactt gatttgggtg atggttcacg tagtgggcca 2280
tcgccctgat agacggtttt tcgccctttg acgttggagt ccacgttctt taatagtgga 2340
ctcttgttcc aaactggaac aacactcaac cctatctcgg gctattcttt tgatttataa 2400
gggattttgc cgatttcggc ctattggtta aaaaatgagc tgatttaaca aaaatttaac 2460
gcgaatttta acaaaatatt aacgtttaca attttatggt gcactctcag tacaatctgc 2520
tctgatgccg catagttaag ccagccccga cacccgccaa cacccgctga cgcgccctga 2580
cgggcttgtc tgctcccggc atccgcttac agacaagctg tgaccgtctc cgggagctgc 2640
atgtgtcaga ggttttcacc gtcatcaccg aaacgcgcga gacgaaaggg cctcgtgata 2700
cgcctatttt tataggttaa tgtcatgata ataatggttt cttagacgtc aggtggcact 2760
tttcggggaa atgtgcgcgg aacccctatt tgtttatttt tctaaataca ttcaaatatg 2820
tatccgctca tgagacaata accctgataa atgcttcaat aatattgaaa aaggaagagt 2880
atgagtattc aacatttccg tgtcgccctt attccctttt ttgcggcatt ttgccttcct 2940
gtttttgctc acccagaaac gctggtgaaa gtaaaagatg ctgaagatca gttgggtgca 3000
cgagtgggtt acatcgaact ggatctcaac agcggtaaga tccttgagag ttttcgcccc 3060
gaagaacgtt ttccaatgat gagcactttt aaagttctgc tatgtggcgc ggtattatcc 3120
cgtattgacg ccgggcaaga gcaactcggt cgccgcatac actattctca gaatgacttg 3180
gttgagtact caccagtcac agaaaagcat cttacggatg gcatgacagt aagagaatta 3240
tgcagtgctg ccataaccat gagtgataac actgcggcca acttacttct gacaacgatc 3300
ggaggaccga aggagctaac cgcttttttg cacaacatgg gggatcatgt aactcgcctt 3360
gatcgttggg aaccggagct gaatgaagcc ataccaaacg acgagcgtga caccacgatg 3420
cctgtagcaa tggcaacaac gttgcgcaaa ctattaactg gcgaactact tactctagct 3480
tcccggcaac aattaataga ctggatggag gcggataaag ttgcaggacc acttctgcgc 3540
tcggcccttc cggctggctg gtttattgct gataaatctg gagccggtga gcgtgggtct 3600
cgcggtatca ttgcagcact ggggccagat ggtaagccct cccgtatcgt agttatctac 3660
acgacgggga gtcaggcaac tatggatgaa cgaaatagac agatcgctga gataggtgcc 3720
tcactgatta agcattggta actgtcagac caagtttact catatatact ttagattgat 3780
ttaaaacttc atttttaatt taaaaggatc taggtgaaga tcctttttga taatctcatg 3840
accaaaatcc cttaacgtga gttttcgttc cactgagcgt cagaccccgt agaaaagatc 3900
aaaggatctt cttgagatcc tttttttctg cgcgtaatct gctgcttgca aacaaaaaaa 3960
ccaccgctac cagcggtggt ttgtttgccg gatcaagagc taccaactct ttttccgaag 4020
gtaactggct tcagcagagc gcagatacca aatactgtcc ttctagtgta gccgtagtta 4080
ggccaccact tcaagaactc tgtagcaccg cctacatacc tcgctctgct aatcctgtta 4140
ccagtggctg ctgccagtgg cgataagtcg tgtcttaccg ggttggactc aagacgatag 4200
ttaccggata aggcgcagcg gtcgggctga acggggggtt cgtgcacaca gcccagcttg 4260
gagcgaacga cctacaccga actgagatac ctacagcgtg agctatgaga aagcgccacg 4320
cttcccgaag ggagaaaggc ggacaggtat ccggtaagcg gcagggtcgg aacaggagag 4380
cgcacgaggg agcttccagg gggaaacgcc tggtatcttt atagtcctgt cgggtttcgc 4440
cacctctgac ttgagcgtcg atttttgtga tgctcgtcag gggggcggag cctatggaaa 4500
aacgccagca acgcggcctt tttacggttc ctggcctttt gctggccttt tgctcacatg 4560
ttctttcctg cgttatcccc tgattctgtg gataaccgta ttaccgcctt tgagtgagct 4620
gataccgctc gccgcagccg aacgaccgag cgcagcgagt cagtgagcga ggaagcggaa 4680
gagcgcccaa tacgcaaacc gcctctcccc gcgcgttggc cgattcatta atgcagctgg 4740
cacgacaggt ttcccgactg gaaagcgggc agtgagcgca acgcaattaa tgtgagttag 4800
ctcactcatt aggcacccca ggctttacac tttatgcttc cggctcgtat gttgtgtgga 4860
attgtgagcg gataacaatt tcacacagga aacagctatg accatgatta cgcc 4914

<210> SEQ ID NO 89
<211> LENGTH: 24
<212> TYPE: DNA
<213> ORGANISM: Artificial sequence
<220> FEATURE:
<223> OTHER INFORMATION: Primer HuCkappa

<400> SEQUENCE: 89
acactctccc ctgttgaagc tctt 24

<210> SEQ ID NO 90
<211> LENGTH: 23
<212> TYPE: DNA
<213> ORGANISM: Artificial sequence
<220> FEATURE:
<223> OTHER INFORMATION: Primer HuClambda2

<400> SEQUENCE: 90
tgaacattct gtaggggcca ctg 23

<210> SEQ ID NO 91
<211> LENGTH: 23
<212> TYPE: DNA
<213> ORGANISM: Artificial sequence
<220> FEATURE:
<223> OTHER INFORMATION: Primer HuClambda7

<400> SEQUENCE: 91
agagcattct gcaggggcca ctg 23

<210> SEQ ID NO 92
<211> LENGTH: 747
<212> TYPE: DNA
<213> ORGANISM: Artificial sequence
<220> FEATURE:
<223> OTHER INFORMATION: SC03-014
<220> FEATURE:
<221> NAME/KEY: CDS
<222> LOCATION: (1)..(747)
<223> OTHER INFORMATION: SC03-014

<400> SEQUENCE: 92 tcc atg gct gag gtg cag ctg gtg gag tct ggg gga ggc ttg gta cag 48
Ser Met Ala Glu Val Gln Leu Val Glu Ser Gly Gly Gly Leu Val Gln
1 5 10 15

```
cct ggg ggg tcc ctg aga ctc tcc tgt gca gcc tct gga ttc acc ttt        96
Pro Gly Gly Ser Leu Arg Leu Ser Cys Ala Ala Ser Gly Phe Thr Phe
            20                  25                  30

agc gac tac ttg atg aac tgg gtc cgc cag gcg ccc ggg aag ggg ctg       144
Ser Asp Tyr Leu Met Asn Trp Val Arg Gln Ala Pro Gly Lys Gly Leu
        35                  40                  45

gag tgg gtt ggc cgt att aga agc aaa gct aac agt tac gcg aca gca       192
Glu Trp Val Gly Arg Ile Arg Ser Lys Ala Asn Ser Tyr Ala Thr Ala
    50                  55                  60

tat gct gcg tcg gtg aaa ggc agg ttc acc atc tcc aga gat gat tca       240
Tyr Ala Ala Ser Val Lys Gly Arg Phe Thr Ile Ser Arg Asp Asp Ser
65                  70                  75                  80

aag aac acg gcg tat ctg caa atg aac agc ctg aaa acc gag gac acg       288
Lys Asn Thr Ala Tyr Leu Gln Met Asn Ser Leu Lys Thr Glu Asp Thr
                85                  90                  95

gcc gtg tat tac tgt gct aaa gac ggc agc cgg ttc ccc gcc cgc ttc       336
Ala Val Tyr Tyr Cys Ala Lys Asp Gly Ser Arg Phe Pro Ala Arg Phe
            100                 105                 110

gat tac tgg ggc cag ggc acc ctg gtg acc gtg ctc gag ggt acc gga       384
Asp Tyr Trp Gly Gln Gly Thr Leu Val Thr Val Leu Glu Gly Thr Gly
        115                 120                 125

ggt tcc ggc gga acc ggg tct ggg act ggt acg agc gag ctc acc cag       432
Gly Ser Gly Gly Thr Gly Ser Gly Thr Gly Thr Ser Glu Leu Thr Gln
    130                 135                 140

tct cca tcc tcc ctg tct gca tct gta gga gac aga gtc acc atc act       480
Ser Pro Ser Ser Leu Ser Ala Ser Val Gly Asp Arg Val Thr Ile Thr
145                 150                 155                 160

tgc cgg gca agt cag agc att agc agc tac tta aat tgg tat cag cag       528
Cys Arg Ala Ser Gln Ser Ile Ser Ser Tyr Leu Asn Trp Tyr Gln Gln
                165                 170                 175

aaa cca ggg aaa gcc cct aag ctc ctg atc tat gct gca tcc agt ttg       576
Lys Pro Gly Lys Ala Pro Lys Leu Leu Ile Tyr Ala Ala Ser Ser Leu
            180                 185                 190

caa agt ggg gtc cca tca agg ttc agt ggc agt gga tct ggg aca gat       624
Gln Ser Gly Val Pro Ser Arg Phe Ser Gly Ser Gly Ser Gly Thr Asp
        195                 200                 205

ttc act ctc acc atc agc agt ctg caa cct gaa gat ttt gca act tac       672
Phe Thr Leu Thr Ile Ser Ser Leu Gln Pro Glu Asp Phe Ala Thr Tyr
    210                 215                 220

tac tgt caa cag agt tac agt acc cct cca acg ttc ggc caa ggg acc       720
Tyr Cys Gln Gln Ser Tyr Ser Thr Pro Pro Thr Phe Gly Gln Gly Thr
225                 230                 235                 240

aag gtg gag atc aaa cgt gcg gcc gca                                   747
Lys Val Glu Ile Lys Arg Ala Ala Ala
                245
```

<210> SEQ ID NO 93
<211> LENGTH: 249
<212> TYPE: PRT
<213> ORGANISM: Artificial sequence
<220> FEATURE:
<223> OTHER INFORMATION: SC03-014

<400> SEQUENCE: 93

```
Ser Met Ala Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Asp Tyr Leu Met Asn Trp Val Arg Gln Ala Pro Gly Lys Gly Leu
        35                  40                  45

Glu Trp Val Gly Arg Ile Arg Ser Lys Ala Asn Ser Tyr Ala Thr Ala
```

```
    50                  55                  60

Tyr Ala Ala Ser Val Lys Gly Arg Phe Thr Ile Ser Arg Asp Asp Ser
65                  70                  75                  80

Lys Asn Thr Ala Tyr Leu Gln Met Asn Ser Leu Lys Thr Glu Asp Thr
                85                  90                  95

Ala Val Tyr Tyr Cys Ala Lys Asp Gly Ser Arg Phe Pro Ala Arg Phe
            100                 105                 110

Asp Tyr Trp Gly Gln Gly Thr Leu Val Thr Val Leu Glu Gly Thr Gly
        115                 120                 125

Gly Ser Gly Gly Thr Gly Ser Gly Thr Gly Thr Ser Glu Leu Thr Gln
    130                 135                 140

Ser Pro Ser Ser Leu Ser Ala Ser Val Gly Asp Arg Val Thr Ile Thr
145                 150                 155                 160

Cys Arg Ala Ser Gln Ser Ile Ser Ser Tyr Leu Asn Trp Tyr Gln Gln
                165                 170                 175

Lys Pro Gly Lys Ala Pro Lys Leu Leu Ile Tyr Ala Ala Ser Ser Leu
            180                 185                 190

Gln Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Ser Tyr Ser Thr Pro Pro Thr Phe Gly Gln Gly Thr
225                 230                 235                 240

Lys Val Glu Ile Lys Arg Ala Ala Ala
                245
```

```
<210> SEQ ID NO 94
<211> LENGTH: 762
<212> TYPE: DNA
<213> ORGANISM: Artificial sequence
<220> FEATURE:
<223> OTHER INFORMATION: SC03-022
<220> FEATURE:
<221> NAME/KEY: CDS
<222> LOCATION: (1)..(762)
<223> OTHER INFORMATION: SC03-022

<400> SEQUENCE: 94

gcc atg gcc cag atg cag ctg gtg caa tct gga aca gag gtg aaa aag       48
Ala Met Ala Gln Met Gln Leu Val Gln Ser Gly Thr Glu Val Lys Lys
1               5                   10                  15

ccg ggg gag tct ctg aag atc tcc tgt aag ggt tct gga tac ggc ttt       96
Pro Gly Glu Ser Leu Lys Ile Ser Cys Lys Gly Ser Gly Tyr Gly Phe
            20                  25                  30

atc acc tac tgg atc ggc tgg gtg cgc cag atg ccc ggg aaa ggc ctg      144
Ile Thr Tyr Trp Ile Gly Trp Val Arg Gln Met Pro Gly Lys Gly Leu
        35                  40                  45

gag tgg atg ggg atc atc tat cct ggt gac tct gaa acc aga tac agc      192
Glu Trp Met Gly Ile Ile Tyr Pro Gly Asp Ser Glu Thr Arg Tyr Ser
    50                  55                  60

ccg tcc ttc caa ggc cag gtc acc atc tca gcc gac aag tcc atc aac      240
Pro Ser Phe Gln Gly Gln Val Thr Ile Ser Ala Asp Lys Ser Ile Asn
65                  70                  75                  80

acc gcc tac ctg cag tgg agc agc ctg aag gcc tcg gac acc gcc ata      288
Thr Ala Tyr Leu Gln Trp Ser Ser Leu Lys Ala Ser Asp Thr Ala Ile
                85                  90                  95

tat tac tgt gcg ggg ggt tcg ggg att tct acc cct atg gac gtc tgg      336
Tyr Tyr Cys Ala Gly Gly Ser Gly Ile Ser Thr Pro Met Asp Val Trp
            100                 105                 110
```

```
ggc caa ggg acc acg gtc acc gtc tcg agc ggt acg ggc ggt tca ggc      384
Gly Gln Gly Thr Thr Val Thr Val Ser Ser Gly Thr Gly Gly Ser Gly
        115                 120                 125

gga acc ggc agc ggc act ggc ggg tcg acg gac atc cag ttg acc cag      432
Gly Thr Gly Ser Gly Thr Gly Gly Ser Thr Asp Ile Gln Leu Thr Gln
    130                 135                 140

tct cca gac tcc ctg gct gtg tct ctg ggc gag agg gcc acc atc aac      480
Ser Pro Asp Ser Leu Ala Val Ser Leu Gly Glu Arg Ala Thr Ile Asn
145                 150                 155                 160

tgc aag tcc agc cag agt gtt tta tac agc tcc atc aat aag aac tac      528
Cys Lys Ser Ser Gln Ser Val Leu Tyr Ser Ser Ile Asn Lys Asn Tyr
                165                 170                 175

tta gct tgg tac cag cag aaa cca gga cag cct cct aag ctg ctc att      576
Leu Ala Trp Tyr Gln Gln Lys Pro Gly Gln Pro Pro Lys Leu Leu Ile
            180                 185                 190

tac tgg gca tct acc cgg gaa tcc ggg gtc cct gac cga ttc agt ggc      624
Tyr Trp Ala Ser Thr Arg Glu Ser Gly Val Pro Asp Arg Phe Ser Gly
        195                 200                 205

agc ggg tct ggg aca gat ttc act ctc acc atc agc agc ctg cag gct      672
Ser Gly Ser Gly Thr Asp Phe Thr Leu Thr Ile Ser Ser Leu Gln Ala
    210                 215                 220

gaa gat gtg gca gtt tat tac tgt cag caa tat tat agt act ccg tac      720
Glu Asp Val Ala Val Tyr Tyr Cys Gln Gln Tyr Tyr Ser Thr Pro Tyr
225                 230                 235                 240

act ttt ggc cag ggg acc aag gtg gaa atc aaa cgt gcg gcc              762
Thr Phe Gly Gln Gly Thr Lys Val Glu Ile Lys Arg Ala Ala
                245                 250


<210> SEQ ID NO 95
<211> LENGTH: 254
<212> TYPE: PRT
<213> ORGANISM: Artificial sequence
<220> FEATURE:
<223> OTHER INFORMATION: SC03-022

<400> SEQUENCE: 95

Ala Met Ala Gln Met Gln Leu Val Gln Ser Gly Thr Glu Val Lys Lys
1               5                   10                  15

Pro Gly Glu Ser Leu Lys Ile Ser Cys Lys Gly Ser Gly Tyr Gly Phe
            20                  25                  30

Ile Thr Tyr Trp Ile Gly Trp Val Arg Gln Met Pro Gly Lys Gly Leu
        35                  40                  45

Glu Trp Met Gly Ile Ile Tyr Pro Gly Asp Ser Glu Thr Arg Tyr Ser
    50                  55                  60

Pro Ser Phe Gln Gly Gln Val Thr Ile Ser Ala Asp Lys Ser Ile Asn
65                  70                  75                  80

Thr Ala Tyr Leu Gln Trp Ser Ser Leu Lys Ala Ser Asp Thr Ala Ile
                85                  90                  95

Tyr Tyr Cys Ala Gly Gly Ser Gly Ile Ser Thr Pro Met Asp Val Trp
            100                 105                 110

Gly Gln Gly Thr Thr Val Thr Val Ser Ser Gly Thr Gly Gly Ser Gly
        115                 120                 125

Gly Thr Gly Ser Gly Thr Gly Gly Ser Thr Asp Ile Gln Leu Thr Gln
    130                 135                 140

Ser Pro Asp Ser Leu Ala Val Ser Leu Gly Glu Arg Ala Thr Ile Asn
145                 150                 155                 160

Cys Lys Ser Ser Gln Ser Val Leu Tyr Ser Ser Ile Asn Lys Asn Tyr
                165                 170                 175

Leu Ala Trp Tyr Gln Gln Lys Pro Gly Gln Pro Pro Lys Leu Leu Ile
```

```
            180                 185                 190

Tyr Trp Ala Ser Thr Arg Glu Ser Gly Val Pro Asp Arg Phe Ser Gly
        195                 200                 205

Ser Gly Ser Gly Thr Asp Phe Thr Leu Thr Ile Ser Ser Leu Gln Ala
    210                 215                 220

Glu Asp Val Ala Val Tyr Tyr Cys Gln Gln Tyr Tyr Ser Thr Pro Tyr
225                 230                 235                 240

Thr Phe Gly Gln Gly Thr Lys Val Glu Ile Lys Arg Ala Ala
                245                 250


<210> SEQ ID NO 96
<211> LENGTH: 6778
<212> TYPE: DNA
<213> ORGANISM: Artificial sequence
<220> FEATURE:
<223> OTHER INFORMATION: Vector pSyn-C03-HCgamma1

<400> SEQUENCE: 96

gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgct aggtggtcaa tattggccat tagccatatt    240

attcattggt tatatagcat aaatcaatat tggctattgg ccattgcata cgttgtatcc    300

atatcataat atgtacattt atattggctc atgtccaaca ttaccgccat gttgacattg    360

attattgact agttattaat agtaatcaat tacggggtca ttagttcata gcccatatat    420

ggagttccgc gttacataac ttacggtaaa tggcccgcct ggctgaccgc ccaacgaccc    480

ccgcccattg acgtcaataa tgacgtatgt tcccatagta acgccaatag ggactttcca    540

ttgacgtcaa tgggtggagt atttacggta aactgcccac ttggcagtac atcaagtgta    600

tcatatgcca agtacgcccc ctattgacgt caatgacggt aaatggcccg cctggcatta    660

tgcccagtac atgaccttat gggactttcc tacttggcag tacatctacg tattagtcat    720

cgctattacc atggtgatgc ggttttggca gtacatcaat gggcgtggat agcggtttga    780

ctcacgggga tttccaagtc tccaccccat tgacgtcaat gggagtttgt tttggcacca    840

aaatcaacgg gactttccaa aatgtcgtaa caactccgcc ccattgacgc aaatgggcgg    900

taggcgtgta cggtgggagg tctatataag cagagctcgt ttagtgaacc gtcagatcgc    960

ctggagacgc catccacgct gttttgacct ccatagaaga caccgggacc gatccagcct   1020

ccgcggccgg gaacggtgca ttggaagctg gcctggatgg cctgactctc ttaggtagcc   1080

ttgcagaagt tggtcgtgag gcactgggca ggtaagtatc aaggttacaa gacaggttta   1140

aggagatcaa tagaaactgg gcttgtcgag acagagaaga ctcttgcgtt tctgataggc   1200

acctattggt cttactgaca tccactttgc ctttctctcc acaggtgtcc actcccagtt   1260

caattacagc tcgccaccat ggcctgcccc ggcttcctgt gggccctggt gatcagcacc   1320

tgcctggaat tcagcatgag cagcgctagc accaagggcc ccagcgtgtt cccccctggcc  1380

cccagcagca agagcaccag cggcggcaca gccgccctgg gctgcctggt gaaggactac   1440

ttccccgagc ccgtgaccgt gagctggaac agcggcgcct tgaccagcgg cgtgcacacc   1500

ttccccgccg tgctgcagag cagcggcctg tacagcctga gcagcgtggt gaccgtgccc   1560

agcagcagcc tgggcaccca gacctacatc tgcaacgtga accacaagcc cagcaacacc   1620

aaggtggaca aacgcgtgga gcccaagagc tgcgacaaga cccacacctg ccccccctgc   1680
```

-continued

```
cctgcccccg agctgctggg cggaccctcc gtgttcctgt tcccccccaa gcccaaggac   1740
accctcatga tcagccggac ccccgaggtg acctgcgtgg tggtggacgt gagccacgag   1800
gaccccgagg tgaagttcaa ctggtacgtg gacggcgtgg aggtgcacaa cgccaagacc   1860
aagccccggg aggagcagta caacagcacc taccgggtgg tgagcgtgct caccgtgctg   1920
caccaggact ggctgaacgg caaggagtac aagtgcaagg tgagcaacaa ggccctgcct   1980
gcccccatcg agaagaccat cagcaaggcc aagggccagc cccgggagcc ccaggtgtac   2040
accctgcccc ccagccggga ggagatgacc aagaaccagg tgtccctcac ctgtctggtg   2100
aagggcttct accccagcga catcgccgtg gagtgggaga gcaacggcca gcccgagaac   2160
aactacaaga ccaccccccc tgtgctggac agcgacggca gcttcttcct gtacagcaag   2220
ctcaccgtgg acaagagccg gtggcagcag ggcaacgtgt tcagctgcag cgtgatgcac   2280
gaggccctgc acaaccacta cacccagaag agcctgagcc tgagccccgg caagtgataa   2340
tctagagggc ccgtttaaac ccgctgatca gcctcgactg tgccttctag ttgccagcca   2400
tctgttgttt gcccctcccc cgtgccttcc ttgaccctgg aaggtgccac tcccactgtc   2460
ctttcctaat aaaatgagga aattgcatcg cattgtctga gtaggtgtca ttctattctg   2520
gggggtgggg tggggcagga cagcaagggg gaggattggg aagacaatag caggcatgct   2580
ggggatgcgg tgggctctat ggcttctgag gcggaaagaa ccagctgggg ctctaggggg   2640
tatccccacg cgccctgtag cggcgcatta agcgcggcgg gtgtggtggt tacgcgcagc   2700
gtgaccgcta cacttgccag cgccctagcg cccgctcctt tcgctttctt cccttccttt   2760
ctcgccacgt tcgccggctt tccccgtcaa gctctaaatc gggggctccc tttagggttc   2820
cgatttagtg ctttacggca cctcgacccc aaaaaacttg attagggtga tggttcacgt   2880
agtgggccat cgccctgata gacggttttt cgccctttga cgttggagtc cacgttcttt   2940
aatagtggac tcttgttcca aactggaaca acactcaacc ctatctcggt ctattctttt   3000
gatttataag ggattttgcc gatttcggcc tattggttaa aaaatgagct gatttaacaa   3060
aaatttaacg cgaattaatt ctgtggaatg tgtgtcagtt agggtgtgga aagtccccag   3120
gctccccagc aggcagaagt atgcaaagca tgcatctcaa ttagtcagca accaggtgtg   3180
gaaagtcccc aggctcccca gcaggcagaa gtatgcaaag catgcatctc aattagtcag   3240
caaccatagt cccgccccta actccgccca tcccgcccct aactccgccc agttccgccc   3300
attctccgcc ccatggctga ctaatttttt ttatttatgc agaggccgag gccgcctctg   3360
cctctgagct attccagaag tagtgaggag gcttttttgg aggcctaggc ttttgcaaaa   3420
agctcccggg agcttgtata tccattttcg gatctgatca agagacagga tgaggatcgt   3480
ttcgcatgat tgaacaagat ggattgcacg caggttctcc ggccgcttgg gtggagaggc   3540
tattcggcta tgactgggca caacagacaa tcggctgctc tgatgccgcc gtgttccggc   3600
tgtcagcgca ggggcgcccg gttctttttg tcaagaccga cctgtccggt gccctgaatg   3660
aactgcagga cgaggcagcg cggctatcgt ggctggccac gacgggcgtt ccttgcgcag   3720
ctgtgctcga cgttgtcact gaagcgggaa gggactggct gctattgggc gaagtgccgg   3780
ggcaggatct cctgtcatct caccttgctc ctgccgagaa agtatccatc atggctgatg   3840
caatgcggcg gctgcatacg cttgatccgg ctacctgccc attcgaccac caagcgaaac   3900
atcgcatcga gcgagcacgt actcggatgg aagccggtct tgtcgatcag gatgatctgg   3960
acgaagagca tcaggggctc gcgccagccg aactgttcgc caggctcaag gcgcgcatgc   4020
ccgacggcga ggatctcgtc gtgacccatg gcgatgcctg cttgccgaat atcatggtgg   4080
```

-continued aaaatggccg cttttctgga ttcatcgact gtggccggct gggtgtggcg gatcgctatc 4140
aggacatagc gttggctacc cgtgatattg ctgaagagct tggcggcgaa tgggctgacc 4200
gcttcctcgt gctttacggt atcgccgctc ccgattcgca gcgcatcgcc ttctatcgcc 4260
ttcttgacga gttcttctga gcgggactct ggggttcgaa atgaccgacc aagcgacgcc 4320
caacctgcca tcacgagatt tcgattccac cgccgccttc tatgaaaggt tgggcttcgg 4380
aatcgttttc cgggacgccg gctggatgat cctccagcgc ggggatctca tgctggagtt 4440
cttcgcccac cccaacttgt ttattgcagc ttataatggt tacaaataaa gcaatagcat 4500
cacaaatttc acaaataaag catttttttc actgcattct agttgtggtt tgtccaaact 4560
catcaatgta tcttatcatg tctgtatacc gtcgacctct agctagagct tggcgtaatc 4620
atggtcatag ctgtttcctg tgtgaaattg ttatccgctc acaattccac acaacatacg 4680
agccggaagc ataaagtgta aagcctgggg tgcctaatga gtgagctaac tcacattaat 4740
tgcgttgcgc tcactgcccg ctttccagtc gggaaacctg tcgtgccagc tgcattaatg 4800
aatcggccaa cgcgcgggga gaggcggttt gcgtattggg cgctcttccg cttcctcgct 4860
cactgactcg ctgcgctcgg tcgttcggct gcggcgagcg gtatcagctc actcaaaggc 4920
ggtaatacgg ttatccacag aatcagggga taacgcagga aagaacatgt gagcaaaagg 4980
ccagcaaaag gccaggaacc gtaaaaaggc cgcgttgctg gcgtttttcc ataggctccg 5040
cccccctgac gagcatcaca aaaatcgacg ctcaagtcag aggtggcgaa acccgacagg 5100
actataaaga taccaggcgt ttccccctgg aagctccctc gtgcgctctc ctgttccgac 5160
cctgccgctt accggatacc tgtccgcctt tctcccttcg ggaagcgtgg cgctttctca 5220
tagctcacgc tgtaggtatc tcagttcggt gtaggtcgtt cgctccaagc tgggctgtgt 5280
gcacgaaccc cccgttcagc ccgaccgctg cgccttatcc ggtaactatc gtcttgagtc 5340
caacccggta agacacgact tatcgccact ggcagcagcc actggtaaca ggattagcag 5400
agcgaggtat gtaggcggtg ctacagagtt cttgaagtgg tggcctaact acggctacac 5460
tagaagaaca gtatttggta tctgcgctct gctgaagcca gttaccttcg gaaaaagagt 5520
tggtagctct tgatccggca aacaaaccac cgctggtagc ggtttttttg tttgcaagca 5580
gcagattacg cgcagaaaaa aaggatctca agaagatcct ttgatctttt ctacggggtc 5640
tgacgctcag tggaacgaaa actcacgtta agggattttg gtcatgagat tatcaaaaag 5700
gatcttcacc tagatccttt taaattaaaa atgaagtttt aaatcaatct aaagtatata 5760
tgagtaaact tggtctgaca gttaccaatg cttaatcagt gaggcaccta tctcagcgat 5820
ctgtctattt cgttcatcca tagttgcctg actccccgtc gtgtagataa ctacgatacg 5880
ggagggctta ccatctggcc ccagtgctgc aatgataccg cgagacccac gctcaccggc 5940
tccagattta tcagcaataa accagccagc cggaagggcc gagcgcagaa gtggtcctgc 6000
aactttatcc gcctccatcc agtctattaa ttgttgccgg gaagctagag taagtagttc 6060
gccagttaat agtttgcgca acgttgttgc cattgctaca ggcatcgtgg tgtcacgctc 6120
gtcgtttggt atggcttcat tcagctccgg ttcccaacga tcaaggcgag ttacatgatc 6180
ccccatgttg tgcaaaaaag cggttagctc cttcggtcct ccgatcgttg tcagaagtaa 6240
gttggccgca gtgttatcac tcatggttat ggcagcactg cataattctc ttactgtcat 6300
gccatccgta agatgctttt ctgtgactgg tgagtactca accaagtcat tctgagaata 6360
gtgtatgcgg cgaccgagtt gctcttgccc ggcgtcaata cgggataata ccgcgccaca 6420
tagcagaact ttaaaagtgc tcatcattgg aaaacgttct tcggggcgaa aactctcaag 6480

-continued gatcttaccg ctgttgagat ccagttcgat gtaacccact cgtgcaccca actgatcttc 6540
agcatctttt actttcacca gcgtttctgg gtgagcaaaa acaggaaggc aaaatgccgc 6600
aaaaaaggga ataagggcga cacggaaatg ttgaatactc atactcttcc tttttcaata 6660
ttattgaagc atttatcagg gttattgtct catgagcgga tacatatttg aatgtattta 6720
gaaaaataaa caaatagggg ttccgcgcac atttccccga aaagtgccac ctgacgtc 6778

<210> SEQ ID NO 97
<211> LENGTH: 6267
<212> TYPE: DNA
<213> ORGANISM: Artificial sequence
<220> FEATURE:
<223> OTHER INFORMATION: Vector pSyn-C05-Ckappa

<400> SEQUENCE: 97
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgttaa ttaacatgaa 180
gaatctgctt agggttaggc gttttgcgct gcttcgctag gtggtcaata ttggccatta 240
gccatattat tcattggtta tatagcataa atcaatattg gctattggcc attgcatacg 300
ttgtatccat atcataatat gtacatttat attggctcat gtccaacatt accgccatgt 360
tgacattgat tattgactag ttattaatag taatcaatta cggggtcatt agttcatagc 420
ccatatatgg agttccgcgt tacataactt acggtaaatg gcccgcctgg ctgaccgccc 480
aacgaccccc gcccattgac gtcaataatg acgtatgttc ccatagtaac gccaataggg 540
actttccatt gacgtcaatg ggtggagtat ttacggtaaa ctgcccactt ggcagtacat 600
caagtgtatc atatgccaag tacgccccct attgacgtca atgacggtaa atggcccgcc 660
tggcattatg cccagtacat gaccttatgg gactttccta cttggcagta catctacgta 720
ttagtcatcg ctattaccat ggtgatgcgg ttttggcagt acatcaatgg gcgtggatag 780
cggtttgact cacggggatt tccaagtctc caccccattg acgtcaatgg gagtttgttt 840
tggcaccaaa atcaacggga ctttccaaaa tgtcgtaaca actccgcccc attgacgcaa 900
atgggcggta ggcgtgtacg gtgggaggtc tatataagca gagctcgttt agtgaaccgt 960
cagatcgcct ggagacgcca tccacgctgt tttgacctcc atagaagaca ccgggaccga 1020
tccagcctcc gcggccggga acggtgcatt ggaatcgatg actctcttag gtagccttgc 1080
agaagttggt cgtgaggcac tgggcaggta agtatcaagg ttacaagaca ggtttaagga 1140
gatcaataga aactgggctt gtcgagacag agaagactct tgcgtttctg ataggcacct 1200
attggtctta ctgacatcca ctttgccttt ctctccacag gtgtccactc ccagttcaat 1260
tacagctcgc caccatggcc tgccccggct tcctgtgggc cctggtgatc agcacctgcc 1320
tcgagttcag cggccctaag cggaccgtgg ccgctcccag cgtgttcatc ttcccccccct 1380 ccgacgagca gctgaagagc ggcaccgcca gcgtggtgtg cctgctgaac aacttctacc 1440
cccgggaggc caaggtgcag tggaaggtgg acaacgccct gcagagcggc aacagccagg 1500
agagcgtgac cgagcaggac agcaaggact ccacctacag cctgagcagc accctcaccc 1560
tgagcaaggc cgactacgag aagcacaagg tgtacgcctg cgaggtgacc caccagggcc 1620
tgagcagccc cgtgaccaag agcttcaacc ggggcgagtg ttaatagact taagtttaaa 1680
ccgctgatca gcctcgactg tgccttctag ttgccagcca tctgttgttt gcccctcccc 1740
cgtgccttcc ttgaccctgg aaggtgccac tcccactgtc ctttcctaat aaaatgagga 1800

-continued aattgcatcg cattgtctga gtaggtgtca ttctattctg gggggtgggg tggggcagga 1860
cagcaagggg gaggattggg aagacaatag caggcatgct ggggatgcgg tgggctctat 1920
ggcttctgag gcggaaagaa ccagctgggg ctctaggggg tatccccacg cgccctgtag 1980
cggcgcatta agcgcggcgg gtgtggtggt tacgcgcagc gtgaccgcta cacttgccag 2040
cgccctagcg cccgctcctt tcgctttctt cccttccttt ctcgccacgt tcgccggctt 2100
tccccgtcaa gctctaaatc gggggctccc tttagggttc cgatttagtg ctttacggca 2160
cctcgacccc aaaaaacttg attagggtga tggttcacgt agtgggccat cgccctgata 2220
gacggttttt cgccctttga cgttggagtc cacgttcttt aatagtggac tcttgttcca 2280
aactggaaca acactcaacc ctatctcggt ctattctttt gatttataag ggattttggc 2340
catttcggcc tattggttaa aaaatgagct gatttaacaa aaatttaacg cgaattaatt 2400
ctgtggaatg tgtgtcagtt agggtgtgga aagtccccag gctccccagc aggcagaagt 2460
atgcaaagca tgcatctcaa ttagtcagca accaggtgtg gaaagtcccc aggctcccca 2520
gcaggcagaa gtatgcaaag catgcatctc aattagtcag caaccatagt cccgccccta 2580
actccgccca tcccgcccct aactccgccc agttccgccc attctccgcc ccatggctga 2640
ctaatttttt ttatttatgc agaggccgag gccgcctctg cctctgagct attccagaag 2700
tagtgaggag gcttttttgg aggcctaggc ttttgcaaaa agctcccggg agcttgtata 2760
tccattttcg gatctgatca gcacgtgatg aaaaagcctg aactcaccgc gacgtctgtc 2820
gagaagtttc tgatcgaaaa gttcgacagc gtctccgacc tgatgcagct ctcggagggc 2880
gaagaatctc gtgctttcag cttcgatgta ggagggcgtg gatatgtcct gcgggtaaat 2940
agctgcgccg atggtttcta caaagatcgt tatgtttatc ggcactttgc atcggccgcg 3000
ctcccgattc cggaagtgct tgacattggg gaattcagcg agagcctgac ctattgcatc 3060
tcccgccgtg cacagggtgt cacgttgcaa gacctgcctg aaaccgaact gcccgctgtt 3120
ctgcagccgg tcgcggaggc catggatgcg atcgctgcgg ccgatcttag ccagacgagc 3180
gggttcggcc cattcggacc acaaggaatc ggtcaataca ctacatggcg tgatttcata 3240
tgcgcgattg ctgatcccca tgtgtatcac tggcaaactg tgatggacga caccgtcagt 3300
gcgtccgtcg cgcaggctct cgatgagctg atgctttggg ccgaggactg ccccgaagtc 3360
cggcacctcg tgcacgcgga tttcggctcc aacaatgtcc tgacggacaa tggccgcata 3420
acagcggtca ttgactggag cgaggcgatg ttcggggatt cccaatacga ggtcgccaac 3480
atcttcttct ggaggccgtg gttggcttgt atggagcagc agacgcgcta cttcgagcgg 3540
aggcatccgg agcttgcagg atcgccgcgg ctccgggcgt atatgctccg cattggtctt 3600
gaccaactct atcagagctt ggttgacggc aatttcgatg atgcagcttg ggcgcagggt 3660
cgatgcgacg caatcgtccg atccggagcc gggactgtcg ggcgtacaca aatcgcccgc 3720
agaagcgcgg ccgtctggac cgatggctgt gtagaagtac tcgccgatag tggaaaccga 3780
cgccccagca ctcgtccgag ggcaaaggaa tagcacgtgc tacgagattt cgattccacc 3840
gccgccttct atgaaaggtt gggcttcgga atcgttttcc gggacgccgg ctggatgatc 3900
ctccagcgcg gggatctcat gctggagttc ttcgcccacc ccaacttgtt tattgcagct 3960
tataatggtt acaaataaag caatagcatc acaaatttca caaataaagc atttttttca 4020
ctgcattcta gttgtggttt gtccaaactc atcaatgtat cttatcatgt ctgtataccg 4080
tcgacctcta gctagagctt ggcgtaatca tggtcatagc tgtttcctgt gtgaaattgt 4140
tatccgctca caattccaca caacatacga gccggaagca taaagtgtaa agcctggggt 4200

-continued

```
gcctaatgag tgagctaact cacattaatt gcgttgcgct cactgcccgc tttccagtcg   4260

ggaaacctgt cgtgccagct gcattaatga atcggccaac gcgcggggag aggcggtttg   4320

cgtattgggc gctcttccgc ttcctcgctc actgactcgc tgcgctcggt cgttcggctg   4380

cggcgagcgg tatcagctca ctcaaaggcg gtaatacggt tatccacaga atcaggggat   4440

aacgcaggaa agaacatgtg agcaaaaggc cagcaaaagg ccaggaaccg taaaaaggcc   4500

gcgttgctgg cgtttttcca taggctccgc ccccctgacg agcatcacaa aaatcgacgc   4560

tcaagtcaga ggtggcgaaa cccgacagga ctataaagat accaggcgtt tccccctgga   4620

agctccctcg tgcgctctcc tgttccgacc ctgccgctta ccggatacct gtccgccttt   4680

ctcccttcgg gaagcgtggc gctttctcat agctcacgct gtaggtatct cagttcggtg   4740

taggtcgttc gctccaagct gggctgtgtg cacgaacccc ccgttcagcc cgaccgctgc   4800

gccttatccg gtaactatcg tcttgagtcc aacccggtaa gacacgactt atcgccactg   4860

gcagcagcca ctggtaacag gattagcaga gcgaggtatg taggcggtgc tacagagttc   4920

ttgaagtggt ggcctaacta cggctacact agaagaacag tatttggtat ctgcgctctg   4980

ctgaagccag ttaccttcgg aaaaagagtt ggtagctctt gatccggcaa acaaaccacc   5040

gctggtagcg gtttttttgt ttgcaagcag cagattacgc gcagaaaaaa aggatctcaa   5100

gaagatcctt tgatcttttc tacggggtct gacgctcagt ggaacgaaaa ctcacgttaa   5160

gggattttgg tcatgagatt atcaaaaagg atcttcacct agatcctttt aaattaaaaa   5220

tgaagtttta aatcaatcta aagtatatat gagtaaactt ggtctgacag ttaccaatgc   5280

ttaatcagtg aggcacctat ctcagcgatc tgtctatttc gttcatccat agttgcctga   5340

ctccccgtcg tgtagataac tacgatacgg gagggcttac catctggccc cagtgctgca   5400

atgataccgc gagacccacg ctcaccggct ccagatttat cagcaataaa ccagccagcc   5460

ggaagggccg agcgcagaag tggtcctgca actttatccg cctccatcca gtctattaat   5520

tgttgccggg aagctagagt aagtagttcg ccagttaata gtttgcgcaa cgttgttgcc   5580

attgctacag gcatcgtggt gtcacgctcg tcgtttggta tggcttcatt cagctccggt   5640

tcccaacgat caaggcgagt tacatgatcc cccatgttgt gcaaaaaagc ggttagctcc   5700

ttcggtcctc cgatcgttgt cagaagtaag ttggccgcag tgttatcact catggttatg   5760

gcagcactgc ataattctct tactgtcatg ccatccgtaa gatgcttttc tgtgactggt   5820

gagtactcaa ccaagtcatt ctgagaatag tgtatgcggc gaccgagttg ctcttgcccg   5880

gcgtcaatac gggataatac cgcgccacat agcagaactt taaaagtgct catcattgga   5940

aaacgttctt cggggcgaaa actctcaagg atcttaccgc tgttgagatc cagttcgatg   6000

taacccactc gtgcacccaa ctgatcttca gcatctttta ctttcaccag cgtttctggg   6060

tgagcaaaaa caggaaggca aaatgccgca aaaaagggaa taagggcgac acggaaatgt   6120

tgaatactca tactcttcct ttttcaatat tattgaagca tttatcaggg ttattgtctc   6180

atgagcggat acatatttga atgtatttag aaaaataaac aaataggggt tccgcgcaca   6240

tttccccgaa aagtgccacc tgacgtc                                        6267
```

<210> SEQ ID NO 98
<211> LENGTH: 54
<212> TYPE: DNA
<213> ORGANISM: Artificial sequence
<220> FEATURE:
<223> OTHER INFORMATION: Oligonucleotide 5K-I

<400> SEQUENCE: 98
acctgtctcg agttttccat ggctgacatc cagatgaccc agtctccatc ctcc 54

<210> SEQ ID NO 99
<211> LENGTH: 42
<212> TYPE: DNA
<213> ORGANISM: Artificial sequence
<220> FEATURE:
<223> OTHER INFORMATION: Oligonucleotide sy3K-C

<400> SEQUENCE: 99
gctgggggcg gccacggtcc gtttgatctc caccttggtc cc 42

<210> SEQ ID NO 100
<211> LENGTH: 49
<212> TYPE: DNA
<213> ORGANISM: Artificial sequence
<220> FEATURE:
<223> OTHER INFORMATION: Oligonucleotide 5K-J

<400> SEQUENCE: 100
acctgtctcg agttttccat ggctgacatc gtgatgaccc agtctccag 49

<210> SEQ ID NO 101
<211> LENGTH: 42
<212> TYPE: DNA
<213> ORGANISM: Artificial sequence
<220> FEATURE:
<223> OTHER INFORMATION: Oligonucleotide sy3K-F

<400> SEQUENCE: 101
gctgggggcg gccacggtcc gcttgatctc caccttggtc cc 42

<210> SEQ ID NO 102
<211> LENGTH: 46
<212> TYPE: DNA
<213> ORGANISM: Artificial sequence
<220> FEATURE:
<223> OTHER INFORMATION: Oligonucleotide 5H-B

<400> SEQUENCE: 102
acctgtcttg aattctccat ggccgaggtg cagctggtgg agtctg 46

<210> SEQ ID NO 103
<211> LENGTH: 47
<212> TYPE: DNA
<213> ORGANISM: Artificial sequence
<220> FEATURE:
<223> OTHER INFORMATION: Oligonucleotide sy3H-A

<400> SEQUENCE: 103
gcccttggtg ctagcgctgg agacggtcac cagggtgccc tggcccc 47

<210> SEQ ID NO 104
<211> LENGTH: 47
<212> TYPE: DNA
<213> ORGANISM: Artificial sequence
<220> FEATURE:
<223> OTHER INFORMATION: Oligonucleotide 5H-H

<400> SEQUENCE: 104
acctgtcttg aattctccat ggccgaggtg cagctggtgc agtctgg 47

<210> SEQ ID NO 105
<211> LENGTH: 47
<212> TYPE: DNA
<213> ORGANISM: Artificial sequence
<220> FEATURE:

```
<223> OTHER INFORMATION: Oligonucleotide sy3H-C

<400> SEQUENCE: 105

gcccttggtg ctagcgctgg agacggtcac ggtggtgccc tggcccc                47


<210> SEQ ID NO 106
<211> LENGTH: 1350
<212> TYPE: DNA
<213> ORGANISM: Artificial sequence
<220> FEATURE:
<223> OTHER INFORMATION: IgG heavy chain of CR03-014
<220> FEATURE:
<221> NAME/KEY: CDS
<222> LOCATION: (1)..(1350)
<223> OTHER INFORMATION: IgG heavy chain of CR03-014

<400> SEQUENCE: 106

gag gtg cag ctg gtg gag tct ggg gga ggc ttg gtc cag cct gga ggg       48
Glu Val Gln Leu Val Glu Ser Gly Gly Gly Leu Val Gln Pro Gly Gly
1               5                   10                  15

tcc ctg aga ctc tcc tgt gca gcc tct gga ttc acc ttc agt gac cac       96
Ser Leu Arg Leu Ser Cys Ala Ala Ser Gly Phe Thr Phe Ser Asp His
            20                  25                  30

tac atg gac tgg gtc cgc cag gct cca ggg aag ggg ctg gag tgg gtt      144
Tyr Met Asp Trp Val Arg Gln Ala Pro Gly Lys Gly Leu Glu Trp Val
        35                  40                  45

ggc cgt act aga aac aaa gct aac agt tac acc aca gaa tac gcc gcg      192
Gly Arg Thr Arg Asn Lys Ala Asn Ser Tyr Thr Thr Glu Tyr Ala Ala
    50                  55                  60

tct gtg aaa ggc aga ttc acc atc tca aga gat gat tca aag aac tca      240
Ser Val Lys Gly Arg Phe Thr Ile Ser Arg Asp Asp Ser Lys Asn Ser
65                  70                  75                  80

ctg tat ctg caa atg aac agc ctg aaa acc gag gac acg gcc gtg tat      288
Leu Tyr Leu Gln Met Asn Ser Leu Lys Thr Glu Asp Thr Ala Val Tyr
                85                  90                  95

tac tgt gca agg ggg att tcg ccg ttt tac ttt gac tac tgg ggc cag      336
Tyr Cys Ala Arg Gly Ile Ser Pro Phe Tyr Phe Asp Tyr Trp Gly Gln
            100                 105                 110

ggc acc ctg gtg acc gtc tcc agc gct agc acc aag ggc ccc agc gtg      384
Gly Thr Leu Val Thr Val Ser Ser Ala Ser Thr Lys Gly Pro Ser Val
        115                 120                 125

ttc ccc ctg gcc ccc agc agc aag agc acc agc ggc ggc aca gcc gcc      432
Phe Pro Leu Ala Pro Ser Ser Lys Ser Thr Ser Gly Gly Thr Ala Ala
    130                 135                 140

ctg ggc tgc ctg gtg aag gac tac ttc ccc gag ccc gtg acc gtg agc      480
Leu Gly Cys Leu Val Lys Asp Tyr Phe Pro Glu Pro Val Thr Val Ser
145                 150                 155                 160

tgg aac agc ggc gcc ttg acc agc ggc gtg cac acc ttc ccc gcc gtg      528
Trp Asn Ser Gly Ala Leu Thr Ser Gly Val His Thr Phe Pro Ala Val
                165                 170                 175

ctg cag agc agc ggc ctg tac agc ctg agc agc gtg gtg acc gtg ccc      576
Leu Gln Ser Ser Gly Leu Tyr Ser Leu Ser Ser Val Val Thr Val Pro
            180                 185                 190

agc agc agc ctg ggc acc cag acc tac atc tgc aac gtg aac cac aag      624
Ser Ser Ser Leu Gly Thr Gln Thr Tyr Ile Cys Asn Val Asn His Lys
        195                 200                 205

ccc agc aac acc aag gtg gac aaa cgc gtg gag ccc aag agc tgc gac      672
Pro Ser Asn Thr Lys Val Asp Lys Arg Val Glu Pro Lys Ser Cys Asp
    210                 215                 220

aag acc cac acc tgc ccc ccc tgc cct gcc ccc gag ctg ctg ggc gga      720
Lys Thr His Thr Cys Pro Pro Cys Pro Ala Pro Glu Leu Leu Gly Gly
225                 230                 235                 240
```

```
ccc tcc gtg ttc ctg ttc ccc ccc aag ccc aag gac acc ctc atg atc      768
Pro Ser Val Phe Leu Phe Pro Pro Lys Pro Lys Asp Thr Leu Met Ile
                245                 250                 255

agc cgg acc ccc gag gtg acc tgc gtg gtg gtg gac gtg agc cac gag      816
Ser Arg Thr Pro Glu Val Thr Cys Val Val Val Asp Val Ser His Glu
            260                 265                 270

gac ccc gag gtg aag ttc aac tgg tac gtg gac ggc gtg gag gtg cac      864
Asp Pro Glu Val Lys Phe Asn Trp Tyr Val Asp Gly Val Glu Val His
        275                 280                 285

aac gcc aag acc aag ccc cgg gag gag cag tac aac agc acc tac cgg      912
Asn Ala Lys Thr Lys Pro Arg Glu Glu Gln Tyr Asn Ser Thr Tyr Arg
    290                 295                 300

gtg gtg agc gtg ctc acc gtg ctg cac cag gac tgg ctg aac ggc aag      960
Val Val Ser Val Leu Thr Val Leu His Gln Asp Trp Leu Asn Gly Lys
305                 310                 315                 320

gag tac aag tgc aag gtg agc aac aag gcc ctg cct gcc ccc atc gag     1008
Glu Tyr Lys Cys Lys Val Ser Asn Lys Ala Leu Pro Ala Pro Ile Glu
                325                 330                 335

aag acc atc agc aag gcc aag ggc cag ccc cgg gag ccc cag gtg tac     1056
Lys Thr Ile Ser Lys Ala Lys Gly Gln Pro Arg Glu Pro Gln Val Tyr
            340                 345                 350

acc ctg ccc ccc agc cgg gag gag atg acc aag aac cag gtg tcc ctc     1104
Thr Leu Pro Pro Ser Arg Glu Glu Met Thr Lys Asn Gln Val Ser Leu
        355                 360                 365

acc tgt ctg gtg aag ggc ttc tac ccc agc gac atc gcc gtg gag tgg     1152
Thr Cys Leu Val Lys Gly Phe Tyr Pro Ser Asp Ile Ala Val Glu Trp
    370                 375                 380

gag agc aac ggc cag ccc gag aac aac tac aag acc acc ccc cct gtg     1200
Glu Ser Asn Gly Gln Pro Glu Asn Asn Tyr Lys Thr Thr Pro Pro Val
385                 390                 395                 400

ctg gac agc gac ggc agc ttc ttc ctg tac agc aag ctc acc gtg gac     1248
Leu Asp Ser Asp Gly Ser Phe Phe Leu Tyr Ser Lys Leu Thr Val Asp
                405                 410                 415

aag agc cgg tgg cag cag ggc aac gtg ttc agc tgc agc gtg atg cac     1296
Lys Ser Arg Trp Gln Gln Gly Asn Val Phe Ser Cys Ser Val Met His
            420                 425                 430

gag gcc ctg cac aac cac tac acc cag aag agc ctg agc ctg agc ccc     1344
Glu Ala Leu His Asn His Tyr Thr Gln Lys Ser Leu Ser Leu Ser Pro
        435                 440                 445

ggc aag                                                             1350
Gly Lys
    450


<210> SEQ ID NO 107
<211> LENGTH: 450
<212> TYPE: PRT
<213> ORGANISM: Artificial sequence
<220> FEATURE:
<223> OTHER INFORMATION: IgG heavy chain of CR03-014

<400> SEQUENCE: 107

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80
```

```
Leu Tyr Leu Gln Met Asn Ser Leu Lys Thr Glu Asp Thr Ala Val Tyr
                85                  90                  95

Tyr Cys Ala Arg Gly Ile Ser Pro Phe Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 108
<211> LENGTH: 1347
<212> TYPE: DNA
<213> ORGANISM: Artificial sequence
<220> FEATURE:
<223> OTHER INFORMATION: IgG heavy chain of CR03-022

```
<220> FEATURE:
<221> NAME/KEY: CDS
<222> LOCATION: (1)..(1347)
<223> OTHER INFORMATION: IgG heavy chain of CR03-022

<400> SEQUENCE: 108

gag gtg cag ctg gtg cag tct gga aca gag gtg aaa aag ccg ggg gag       48
Glu Val Gln Leu Val Gln Ser Gly Thr Glu Val Lys Lys Pro Gly Glu
1               5                   10                  15

tct ctg aag atc tcc tgt aag ggt tct gga tac ggc ttt atc acc tac       96
Ser Leu Lys Ile Ser Cys Lys Gly Ser Gly Tyr Gly Phe Ile Thr Tyr
            20                  25                  30

tgg atc ggc tgg gtg cgc cag atg ccc ggg aaa ggc ctg gag tgg atg      144
Trp Ile Gly Trp Val Arg Gln Met Pro Gly Lys Gly Leu Glu Trp Met
        35                  40                  45

ggg atc atc tat cct ggt gac tct gaa acc aga tac agc ccg tcc ttc      192
Gly Ile Ile Tyr Pro Gly Asp Ser Glu Thr Arg Tyr Ser Pro Ser Phe
    50                  55                  60

caa ggc cag gtc acc atc tca gcc gac aag tcc atc aac acc gcc tac      240
Gln Gly Gln Val Thr Ile Ser Ala Asp Lys Ser Ile Asn Thr Ala Tyr
65                  70                  75                  80

ctg cag tgg agc agc ctg aag gcc tcg gac acc gcc ata tat tac tgt      288
Leu Gln Trp Ser Ser Leu Lys Ala Ser Asp Thr Ala Ile Tyr Tyr Cys
                85                  90                  95

gcg ggg ggt tcg ggg att tct acc cct atg gac gtc tgg ggc cag ggc      336
Ala Gly Gly Ser Gly Ile Ser Thr Pro Met Asp Val Trp Gly Gln Gly
            100                 105                 110

acc acc gtg acc gtc tcc agc gct agc acc aag ggc ccc agc gtg ttc      384
Thr Thr Val Thr Val Ser Ser Ala Ser Thr Lys Gly Pro Ser Val Phe
        115                 120                 125

ccc ctg gcc ccc agc agc aag agc acc agc ggc ggc aca gcc gcc ctg      432
Pro Leu Ala Pro Ser Ser Lys Ser Thr Ser Gly Gly Thr Ala Ala Leu
    130                 135                 140

ggc tgc ctg gtg aag gac tac ttc ccc gag ccc gtg acc gtg agc tgg      480
Gly Cys Leu Val Lys Asp Tyr Phe Pro Glu Pro Val Thr Val Ser Trp
145                 150                 155                 160

aac agc ggc gcc ttg acc agc ggc gtg cac acc ttc ccc gcc gtg ctg      528
Asn Ser Gly Ala Leu Thr Ser Gly Val His Thr Phe Pro Ala Val Leu
                165                 170                 175

cag agc agc ggc ctg tac agc ctg agc agc gtg gtg acc gtg ccc agc      576
Gln Ser Ser Gly Leu Tyr Ser Leu Ser Ser Val Val Thr Val Pro Ser
            180                 185                 190

agc agc ctg ggc acc cag acc tac atc tgc aac gtg aac cac aag ccc      624
Ser Ser Leu Gly Thr Gln Thr Tyr Ile Cys Asn Val Asn His Lys Pro
        195                 200                 205

agc aac acc aag gtg gac aaa cgc gtg gag ccc aag agc tgc gac aag      672
Ser Asn Thr Lys Val Asp Lys Arg Val Glu Pro Lys Ser Cys Asp Lys
    210                 215                 220

acc cac acc tgc ccc ccc tgc cct gcc ccc gag ctg ctg ggc gga ccc      720
Thr His Thr Cys Pro Pro Cys Pro Ala Pro Glu Leu Leu Gly Gly Pro
225                 230                 235                 240

tcc gtg ttc ctg ttc ccc ccc aag ccc aag gac acc ctc atg atc agc      768
Ser Val Phe Leu Phe Pro Pro Lys Pro Lys Asp Thr Leu Met Ile Ser
                245                 250                 255

cgg acc ccc gag gtg acc tgc gtg gtg gtg gac gtg agc cac gag gac      816
Arg Thr Pro Glu Val Thr Cys Val Val Val Asp Val Ser His Glu Asp
            260                 265                 270

ccc gag gtg aag ttc aac tgg tac gtg gac ggc gtg gag gtg cac aac      864
Pro Glu Val Lys Phe Asn Trp Tyr Val Asp Gly Val Glu Val His Asn
        275                 280                 285

gcc aag acc aag ccc cgg gag gag cag tac aac agc acc tac cgg gtg      912
```

```
Ala Lys Thr Lys Pro Arg Glu Glu Gln Tyr Asn Ser Thr Tyr Arg Val
    290                 295                 300

gtg agc gtg ctc acc gtg ctg cac cag gac tgg ctg aac ggc aag gag      960
Val Ser Val Leu Thr Val Leu His Gln Asp Trp Leu Asn Gly Lys Glu
305                 310                 315                 320

tac aag tgc aag gtg agc aac aag gcc ctg cct gcc ccc atc gag aag     1008
Tyr Lys Cys Lys Val Ser Asn Lys Ala Leu Pro Ala Pro Ile Glu Lys
                325                 330                 335

acc atc agc aag gcc aag ggc cag ccc cgg gag ccc cag gtg tac acc     1056
Thr Ile Ser Lys Ala Lys Gly Gln Pro Arg Glu Pro Gln Val Tyr Thr
            340                 345                 350

ctg ccc ccc agc cgg gag gag atg acc aag aac cag gtg tcc ctc acc     1104
Leu Pro Pro Ser Arg Glu Glu Met Thr Lys Asn Gln Val Ser Leu Thr
        355                 360                 365

tgt ctg gtg aag ggc ttc tac ccc agc gac atc gcc gtg gag tgg gag     1152
Cys Leu Val Lys Gly Phe Tyr Pro Ser Asp Ile Ala Val Glu Trp Glu
    370                 375                 380

agc aac ggc cag ccc gag aac aac tac aag acc acc ccc cct gtg ctg     1200
Ser Asn Gly Gln Pro Glu Asn Asn Tyr Lys Thr Thr Pro Pro Val Leu
385                 390                 395                 400

gac agc gac ggc agc ttc ttc ctg tac agc aag ctc acc gtg gac aag     1248
Asp Ser Asp Gly Ser Phe Phe Leu Tyr Ser Lys Leu Thr Val Asp Lys
                405                 410                 415

agc cgg tgg cag cag ggc aac gtg ttc agc tgc agc gtg atg cac gag     1296
Ser Arg Trp Gln Gln Gly Asn Val Phe Ser Cys Ser Val Met His Glu
            420                 425                 430

gcc ctg cac aac cac tac acc cag aag agc ctg agc ctg agc ccc ggc     1344
Ala Leu His Asn His Tyr Thr Gln Lys Ser Leu Ser Leu Ser Pro Gly
        435                 440                 445

aag                                                                 1347
Lys


<210> SEQ ID NO 109
<211> LENGTH: 449
<212> TYPE: PRT
<213> ORGANISM: Artificial sequence
<220> FEATURE:
<223> OTHER INFORMATION: IgG heavy chain of CR03-022

<400> SEQUENCE: 109

Glu Val Gln Leu Val Gln Ser Gly Thr Glu Val Lys Lys Pro Gly Glu
1               5                   10                  15

Ser Leu Lys Ile Ser Cys Lys Gly Ser Gly Tyr Gly Phe Ile Thr Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Glu Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Ala Gly Gly Ser Gly Ile Ser Thr Pro Met Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
```

```
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 110
<211> LENGTH: 642
<212> TYPE: DNA
<213> ORGANISM: Artificial sequence
<220> FEATURE:
<223> OTHER INFORMATION: IgG light chain of CR03-014
<220> FEATURE:
<221> NAME/KEY: CDS
<222> LOCATION: (1)..(642)
<223> OTHER INFORMATION: IgG light chain of CR03-014

<400> SEQUENCE: 110

gac atc cag atg acc cag tct cca tcc tcc ctg tct gca tct gta gga       48
Asp Ile Gln Met Thr Gln Ser Pro Ser Ser Leu Ser Ala Ser Val Gly
1               5                   10                  15

gac aga gtc acc atc act tgc cgg gca agt cag agc att agc agc tac       96
Asp Arg Val Thr Ile Thr Cys Arg Ala Ser Gln Ser Ile Ser Ser Tyr
            20                  25                  30
```

-continued

```
tta aat tgg tat cag cag aaa cca ggg aaa gcc cct aag ctc ctg atc      144
Leu Asn Trp Tyr Gln Gln Lys Pro Gly Lys Ala Pro Lys Leu Leu Ile
        35                  40                  45

tat gct gca tcc agt ttg caa agt ggg gtc cca tca agg ttc agt ggc      192
Tyr Ala Ala Ser Ser Leu Gln Ser Gly Val Pro Ser Arg Phe Ser Gly
    50                  55                  60

agt gga tct ggg aca gat ttc act ctc acc atc agc agt ctg caa cct      240
Ser Gly Ser Gly Thr Asp Phe Thr Leu Thr Ile Ser Ser Leu Gln Pro
65                  70                  75                  80

gaa gat ttt gca act tac tac tgt caa cag agt tac agt acc cct cca      288
Glu Asp Phe Ala Thr Tyr Tyr Cys Gln Gln Ser Tyr Ser Thr Pro Pro
                85                  90                  95

acg ttc ggc caa ggg acc aag gtg gag atc aaa cgg acc gtg gcc gct      336
Thr Phe Gly Gln Gly Thr Lys Val Glu Ile Lys Arg Thr Val Ala Ala
            100                 105                 110

ccc agc gtg ttc atc ttc ccc ccc tcc gac gag cag ctg aag agc ggc      384
Pro Ser Val Phe Ile Phe Pro Pro Ser Asp Glu Gln Leu Lys Ser Gly
        115                 120                 125

acc gcc agc gtg gtg tgc ctg ctg aac aac ttc tac ccc cgg gag gcc      432
Thr Ala Ser Val Val Cys Leu Leu Asn Asn Phe Tyr Pro Arg Glu Ala
    130                 135                 140

aag gtg cag tgg aag gtg gac aac gcc ctg cag agc ggc aac agc cag      480
Lys Val Gln Trp Lys Val Asp Asn Ala Leu Gln Ser Gly Asn Ser Gln
145                 150                 155                 160

gag agc gtg acc gag cag gac agc aag gac tcc acc tac agc ctg agc      528
Glu Ser Val Thr Glu Gln Asp Ser Lys Asp Ser Thr Tyr Ser Leu Ser
                165                 170                 175

agc acc ctc acc ctg agc aag gcc gac tac gag aag cac aag gtg tac      576
Ser Thr Leu Thr Leu Ser Lys Ala Asp Tyr Glu Lys His Lys Val Tyr
            180                 185                 190

gcc tgc gag gtg acc cac cag ggc ctg agc agc ccc gtg acc aag agc      624
Ala Cys Glu Val Thr His Gln Gly Leu Ser Ser Pro Val Thr Lys Ser
        195                 200                 205

ttc aac cgg ggc gag tgt                                              642
Phe Asn Arg Gly Glu Cys
    210


<210> SEQ ID NO 111
<211> LENGTH: 214
<212> TYPE: PRT
<213> ORGANISM: Artificial sequence
<220> FEATURE:
<223> OTHER INFORMATION: IgG light chain of CR03-014

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
```

```
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 112
<211> LENGTH: 660
<212> TYPE: DNA
<213> ORGANISM: Artificial sequence
<220> FEATURE:
<223> OTHER INFORMATION: IgG light chain of CR03-022
<220> FEATURE:
<221> NAME/KEY: CDS
<222> LOCATION: (1)..(660)
<223> OTHER INFORMATION: IgG light chain of CR03-022

<400> SEQUENCE: 112

gac atc gtg atg acc cag tct cca gac tcc ctg gct gtg tct ctg ggc       48
Asp Ile Val Met Thr Gln Ser Pro Asp Ser Leu Ala Val Ser Leu Gly
1               5                   10                  15

gag agg gcc acc atc aac tgc aag tcc agc cag agt gtt tta tac agc       96
Glu Arg Ala Thr Ile Asn Cys Lys Ser Ser Gln Ser Val Leu Tyr Ser
            20                  25                  30

tcc atc aat aag aac tac tta gct tgg tac cag cag aaa cca gga cag      144
Ser Ile Asn Lys Asn Tyr Leu Ala Trp Tyr Gln Gln Lys Pro Gly Gln
        35                  40                  45

cct cct aag ctg ctc att tac tgg gca tct acc cgg gaa tcc ggg gtc      192
Pro Pro Lys Leu Leu Ile Tyr Trp Ala Ser Thr Arg Glu Ser Gly Val
    50                  55                  60

cct gac cga ttc agt ggc agc ggg tct ggg aca gat ttc act ctc acc      240
Pro Asp Arg Phe Ser Gly Ser Gly Ser Gly Thr Asp Phe Thr Leu Thr
65                  70                  75                  80

atc agc agc ctg cag gct gaa gat gtg gca gtt tat tac tgt cag caa      288
Ile Ser Ser Leu Gln Ala Glu Asp Val Ala Val Tyr Tyr Cys Gln Gln
                85                  90                  95

tat tat agt act ccg tac act ttt ggc cag ggg acc aag gtg gag atc      336
Tyr Tyr Ser Thr Pro Tyr Thr Phe Gly Gln Gly Thr Lys Val Glu Ile
            100                 105                 110

aag cgg acc gtg gcc gct ccc agc gtg ttc atc ttc ccc ccc tcc gac      384
Lys Arg Thr Val Ala Ala Pro Ser Val Phe Ile Phe Pro Pro Ser Asp
        115                 120                 125

gag cag ctg aag agc ggc acc gcc agc gtg gtg tgc ctg ctg aac aac      432
Glu Gln Leu Lys Ser Gly Thr Ala Ser Val Val Cys Leu Leu Asn Asn
    130                 135                 140

ttc tac ccc cgg gag gcc aag gtg cag tgg aag gtg gac aac gcc ctg      480
Phe Tyr Pro Arg Glu Ala Lys Val Gln Trp Lys Val Asp Asn Ala Leu
145                 150                 155                 160

cag agc ggc aac agc cag gag agc gtg acc gag cag gac agc aag gac      528
Gln Ser Gly Asn Ser Gln Glu Ser Val Thr Glu Gln Asp Ser Lys Asp
                165                 170                 175

tcc acc tac agc ctg agc agc acc ctc acc ctg agc aag gcc gac tac      576
Ser Thr Tyr Ser Leu Ser Ser Thr Leu Thr Leu Ser Lys Ala Asp Tyr
```

```
            180                 185                 190

gag aag cac aag gtg tac gcc tgc gag gtg acc cac cag ggc ctg agc      624
Glu Lys His Lys Val Tyr Ala Cys Glu Val Thr His Gln Gly Leu Ser
        195                 200                 205

agc ccc gtg acc aag agc ttc aac cgg ggc gag tgt                      660
Ser Pro Val Thr Lys Ser Phe Asn Arg Gly Glu Cys
    210                 215                 220


<210> SEQ ID NO 113
<211> LENGTH: 220
<212> TYPE: PRT
<213> ORGANISM: Artificial sequence
<220> FEATURE:
<223> OTHER INFORMATION: IgG light chain of CR03-022

<400> SEQUENCE: 113

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Ile Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Tyr Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 114
<211> LENGTH: 3789
<212> TYPE: DNA
<213> ORGANISM: Artificial sequence
<220> FEATURE:
<223> OTHER INFORMATION: S protein of SARS-CoV strain Frankfurt 1
<220> FEATURE:
<221> NAME/KEY: CDS
<222> LOCATION: (10)..(3777)
<223> OTHER INFORMATION: S protein of SARS-CoV strain Frankfurt 1

<400> SEQUENCE: 114

ggtaccgcc atg ttc atc ttc ctg ctg ttc ctg acc ctg acc agc ggc agc      51
          Met Phe Ile Phe Leu Leu Phe Leu Thr Leu Thr Ser Gly Ser
          1               5                   10
```

-continued

```
gat ctg gat agg tgc acc acc ttc gac gac gtg cag gcc cct aat tac        99
Asp Leu Asp Arg Cys Thr Thr Phe Asp Asp Val Gln Ala Pro Asn Tyr
15                  20                  25                  30

acc cag cac acc agc tct atg cgg ggc gtg tac tac ccc gac gag atc       147
Thr Gln His Thr Ser Ser Met Arg Gly Val Tyr Tyr Pro Asp Glu Ile
                35                  40                  45

ttc aga agc gac acc ctg tac ctg aca cag gac ctg ttc ctg ccc ttc       195
Phe Arg Ser Asp Thr Leu Tyr Leu Thr Gln Asp Leu Phe Leu Pro Phe
            50                  55                  60

tac agc aac gtg acc ggc ttc cac acc atc aac cac acc ttc ggc aac       243
Tyr Ser Asn Val Thr Gly Phe His Thr Ile Asn His Thr Phe Gly Asn
        65                  70                  75

ccc gtg atc cct ttc aag gac ggc atc tac ttc gcc gcc acc gag aag       291
Pro Val Ile Pro Phe Lys Asp Gly Ile Tyr Phe Ala Ala Thr Glu Lys
    80                  85                  90

agc aat gtg gtg cgg ggc tgg gtg ttc ggc agc acc atg aac aac aag       339
Ser Asn Val Val Arg Gly Trp Val Phe Gly Ser Thr Met Asn Asn Lys
95                  100                 105                 110

agc cag agc gtg atc atc atc aac aat agc acc aac gtg gtg atc agg       387
Ser Gln Ser Val Ile Ile Ile Asn Asn Ser Thr Asn Val Val Ile Arg
                115                 120                 125

gcc tgc aac ttc gag ctg tgc gac aac cct ttc ttc gcc gtg tcc aaa       435
Ala Cys Asn Phe Glu Leu Cys Asp Asn Pro Phe Phe Ala Val Ser Lys
            130                 135                 140

cct atg ggc acc cag acc cac acc atg atc ttc gac aac gcc ttc aac       483
Pro Met Gly Thr Gln Thr His Thr Met Ile Phe Asp Asn Ala Phe Asn
        145                 150                 155

tgc acc ttc gag tac atc agc gac gcc ttc agc ctg gat gtg agc gag       531
Cys Thr Phe Glu Tyr Ile Ser Asp Ala Phe Ser Leu Asp Val Ser Glu
    160                 165                 170

aag agc ggg aac ttc aag cac ctg cgg gag ttc gtg ttc aag aac aag       579
Lys Ser Gly Asn Phe Lys His Leu Arg Glu Phe Val Phe Lys Asn Lys
175                 180                 185                 190

gac ggc ttc ctg tac gtg tac aag ggc tac cag ccc atc gac gtg gtg       627
Asp Gly Phe Leu Tyr Val Tyr Lys Gly Tyr Gln Pro Ile Asp Val Val
                195                 200                 205

aga gat ctg ccc agc ggc ttc aac acc ctg aag ccc atc ttc aag ctg       675
Arg Asp Leu Pro Ser Gly Phe Asn Thr Leu Lys Pro Ile Phe Lys Leu
            210                 215                 220

ccc ctg ggc atc aac atc acc aac ttc cgg gcc atc ctg acc gcc ttc       723
Pro Leu Gly Ile Asn Ile Thr Asn Phe Arg Ala Ile Leu Thr Ala Phe
        225                 230                 235

agc cct gcc cag gac atc tgg ggc acc agc gcc gct gcc tac ttc gtg       771
Ser Pro Ala Gln Asp Ile Trp Gly Thr Ser Ala Ala Ala Tyr Phe Val
    240                 245                 250

ggc tac ctg aag ccc acc acc ttc atg ctg aag tac gac gag aac ggc       819
Gly Tyr Leu Lys Pro Thr Thr Phe Met Leu Lys Tyr Asp Glu Asn Gly
255                 260                 265                 270

acc atc acc gat gcc gtg gac tgc agc cag aac ccc ctg gcc gag ctg       867
Thr Ile Thr Asp Ala Val Asp Cys Ser Gln Asn Pro Leu Ala Glu Leu
                275                 280                 285

aag tgc agc gtg aag agc ttc gag atc gac aag ggc atc tac cag acc       915
Lys Cys Ser Val Lys Ser Phe Glu Ile Asp Lys Gly Ile Tyr Gln Thr
            290                 295                 300

agc aac ttc aga gtg gtg ccc agc ggc gat gtg gtg agg ttc ccc aac       963
Ser Asn Phe Arg Val Val Pro Ser Gly Asp Val Val Arg Phe Pro Asn
        305                 310                 315

atc acc aac ctg tgc cct ttc ggc gag gtg ttc aac gcc acc aag ttc      1011
Ile Thr Asn Leu Cys Pro Phe Gly Glu Val Phe Asn Ala Thr Lys Phe
    320                 325                 330
```

```
cct agc gtg tac gcc tgg gag cgg aag aag atc agc aac tgc gtg gcc      1059
Pro Ser Val Tyr Ala Trp Glu Arg Lys Lys Ile Ser Asn Cys Val Ala
335                 340                 345                 350

gat tac agc gtg ctg tac aac agc acc ttc ttc agc acc ttc aag tgc      1107
Asp Tyr Ser Val Leu Tyr Asn Ser Thr Phe Phe Ser Thr Phe Lys Cys
                355                 360                 365

tac ggc gtg agc gcc acc aag ctg aac gac ctg tgc ttc agc aac gtg      1155
Tyr Gly Val Ser Ala Thr Lys Leu Asn Asp Leu Cys Phe Ser Asn Val
            370                 375                 380

tac gcc gac agc ttc gtg gtg aag ggc gac gac gtg aga cag atc gcc      1203
Tyr Ala Asp Ser Phe Val Val Lys Gly Asp Asp Val Arg Gln Ile Ala
        385                 390                 395

cct ggc cag acc ggc gtg atc gcc gac tac aat tac aag ctg ccc gac      1251
Pro Gly Gln Thr Gly Val Ile Ala Asp Tyr Asn Tyr Lys Leu Pro Asp
    400                 405                 410

gac ttc atg ggc tgc gtg ctg gcc tgg aac acc aga aac atc gac gcc      1299
Asp Phe Met Gly Cys Val Leu Ala Trp Asn Thr Arg Asn Ile Asp Ala
415                 420                 425                 430

acc tcc acc ggc aac tac aac tac aag tac cgc tac ctg agg cac ggc      1347
Thr Ser Thr Gly Asn Tyr Asn Tyr Lys Tyr Arg Tyr Leu Arg His Gly
                435                 440                 445

aag ctg aga ccc ttc gag cgg gac atc agc aac gtg ccc ttc agc cct      1395
Lys Leu Arg Pro Phe Glu Arg Asp Ile Ser Asn Val Pro Phe Ser Pro
            450                 455                 460

gac ggc aag ccc tgc acc ccc cct gcc ctg aac tgc tac tgg ccc ctg      1443
Asp Gly Lys Pro Cys Thr Pro Pro Ala Leu Asn Cys Tyr Trp Pro Leu
        465                 470                 475

aac gac tac ggc ttc tac acc acc acc ggc atc ggc tac cag cct tac      1491
Asn Asp Tyr Gly Phe Tyr Thr Thr Thr Gly Ile Gly Tyr Gln Pro Tyr
    480                 485                 490

aga gtg gtg gtg ctg agc ttc gag ctg ctg aac gcc cct gcc acc gtg      1539
Arg Val Val Val Leu Ser Phe Glu Leu Leu Asn Ala Pro Ala Thr Val
495                 500                 505                 510

tgc ggc ccc aag ctg agc acc gac ctg atc aag aac cag tgc gtg aac      1587
Cys Gly Pro Lys Leu Ser Thr Asp Leu Ile Lys Asn Gln Cys Val Asn
                515                 520                 525

ttc aac ttc aac ggc ctg acc ggc acc ggc gtg ctg acc cct agc agc      1635
Phe Asn Phe Asn Gly Leu Thr Gly Thr Gly Val Leu Thr Pro Ser Ser
            530                 535                 540

aag agg ttc cag ccc ttc cag cag ttc ggc agg gac gtg agc gat ttc      1683
Lys Arg Phe Gln Pro Phe Gln Gln Phe Gly Arg Asp Val Ser Asp Phe
        545                 550                 555

acc gac agc gtg agg gat cct aag acc agc gag atc ctg gac atc agc      1731
Thr Asp Ser Val Arg Asp Pro Lys Thr Ser Glu Ile Leu Asp Ile Ser
    560                 565                 570

cct tgc agc ttc ggc ggc gtg agc gtg atc acc ccc ggc acc aac gcc      1779
Pro Cys Ser Phe Gly Gly Val Ser Val Ile Thr Pro Gly Thr Asn Ala
575                 580                 585                 590

agc tcc gag gtg gcc gtg ctg tac cag gac gtg aac tgc acc gac gtg      1827
Ser Ser Glu Val Ala Val Leu Tyr Gln Asp Val Asn Cys Thr Asp Val
                595                 600                 605

agc acc gcc atc cac gcc gac cag ctg acc ccc gcc tgg aga atc tac      1875
Ser Thr Ala Ile His Ala Asp Gln Leu Thr Pro Ala Trp Arg Ile Tyr
            610                 615                 620

agc acc ggc aac aac gtg ttc cag acc cag gcc ggc tgc ctg atc ggc      1923
Ser Thr Gly Asn Asn Val Phe Gln Thr Gln Ala Gly Cys Leu Ile Gly
        625                 630                 635

gcc gag cac gtg gac acc agc tac gag tgc gac atc ccc atc gga gcc      1971
Ala Glu His Val Asp Thr Ser Tyr Glu Cys Asp Ile Pro Ile Gly Ala
    640                 645                 650
```

-continued

```
ggc atc tgc gcc agc tac cac acc gtg agc ctg ctg aga agc acc agc      2019
Gly Ile Cys Ala Ser Tyr His Thr Val Ser Leu Leu Arg Ser Thr Ser
655                 660                 665                 670

cag aag agc atc gtg gcc tac acc atg agc ctg ggc gcc gac agc agc      2067
Gln Lys Ser Ile Val Ala Tyr Thr Met Ser Leu Gly Ala Asp Ser Ser
                675                 680                 685

atc gcc tac agc aac aac acc atc gcc atc ccc acc aac ttc agc atc      2115
Ile Ala Tyr Ser Asn Asn Thr Ile Ala Ile Pro Thr Asn Phe Ser Ile
            690                 695                 700

agc atc acc acc gag gtg atg ccc gtg agc atg gcc aag acc agc gtg      2163
Ser Ile Thr Thr Glu Val Met Pro Val Ser Met Ala Lys Thr Ser Val
        705                 710                 715

gac tgc aac atg tac atc tgc ggc gac agc acc gag tgc gcc aac ctg      2211
Asp Cys Asn Met Tyr Ile Cys Gly Asp Ser Thr Glu Cys Ala Asn Leu
    720                 725                 730

ctg ctg cag tac ggc agc ttc tgc acc cag ctg aac aga gcc ctg agc      2259
Leu Leu Gln Tyr Gly Ser Phe Cys Thr Gln Leu Asn Arg Ala Leu Ser
735                 740                 745                 750

ggc atc gcc gcc gag cag gac aga aac acc agg gag gtg ttc gcc cag      2307
Gly Ile Ala Ala Glu Gln Asp Arg Asn Thr Arg Glu Val Phe Ala Gln
                755                 760                 765

gtg aag cag atg tat aag acc ccc acc ctg aag tac ttc ggc ggc ttc      2355
Val Lys Gln Met Tyr Lys Thr Pro Thr Leu Lys Tyr Phe Gly Gly Phe
            770                 775                 780

aac ttc agc cag atc ctg ccc gat cct ctg aag ccc acc aag cgg agc      2403
Asn Phe Ser Gln Ile Leu Pro Asp Pro Leu Lys Pro Thr Lys Arg Ser
        785                 790                 795

ttc atc gag gac ctg ctg ttc aac aag gtg acc ctg gcc gac gcc ggc      2451
Phe Ile Glu Asp Leu Leu Phe Asn Lys Val Thr Leu Ala Asp Ala Gly
    800                 805                 810

ttt atg aag cag tac ggc gag tgc ctg ggc gat atc aac gcc agg gac      2499
Phe Met Lys Gln Tyr Gly Glu Cys Leu Gly Asp Ile Asn Ala Arg Asp
815                 820                 825                 830

ctg atc tgc gcc cag aag ttc aat ggc ctg acc gtg ctg ccc ccc ctg      2547
Leu Ile Cys Ala Gln Lys Phe Asn Gly Leu Thr Val Leu Pro Pro Leu
                835                 840                 845

ctg acc gac gac atg atc gcc gcc tac aca gcc gcc ctg gtg agc ggc      2595
Leu Thr Asp Asp Met Ile Ala Ala Tyr Thr Ala Ala Leu Val Ser Gly
            850                 855                 860

acc gcc acc gcc ggc tgg acc ttt ggc gcc gga gcc gcc ctg cag atc      2643
Thr Ala Thr Ala Gly Trp Thr Phe Gly Ala Gly Ala Ala Leu Gln Ile
        865                 870                 875

ccc ttc gcc atg cag atg gcc tac cgg ttc aat ggc atc ggc gtg acc      2691
Pro Phe Ala Met Gln Met Ala Tyr Arg Phe Asn Gly Ile Gly Val Thr
    880                 885                 890

cag aac gtg ctg tac gag aac cag aag cag atc gcc aac cag ttc aac      2739
Gln Asn Val Leu Tyr Glu Asn Gln Lys Gln Ile Ala Asn Gln Phe Asn
895                 900                 905                 910

aag gcc atc agc cag atc cag gag agc ctg acc acc aca agc acc gcc      2787
Lys Ala Ile Ser Gln Ile Gln Glu Ser Leu Thr Thr Thr Ser Thr Ala
                915                 920                 925

ctg ggc aag ctg cag gac gtg gtg aac cag aac gcc cag gcc ctg aat      2835
Leu Gly Lys Leu Gln Asp Val Val Asn Gln Asn Ala Gln Ala Leu Asn
            930                 935                 940

acc ctg gtg aag cag ctg agc agc aac ttc ggc gcc atc agc tcc gtg      2883
Thr Leu Val Lys Gln Leu Ser Ser Asn Phe Gly Ala Ile Ser Ser Val
        945                 950                 955

ctg aac gac atc ctg agc cgg ctg gac aag gtg gag gcc gag gtg cag      2931
Leu Asn Asp Ile Leu Ser Arg Leu Asp Lys Val Glu Ala Glu Val Gln
    960                 965                 970
```

```
atc gac aga ctg atc acc ggc aga ctg cag agc ctg cag acc tac gtg     2979
Ile Asp Arg Leu Ile Thr Gly Arg Leu Gln Ser Leu Gln Thr Tyr Val
975                 980                 985                 990

acc cag cag ctg atc aga gcc gcc gag atc  aga gcc agc gcc aac  ctg   3027
Thr Gln Gln Leu Ile Arg Ala Ala Glu Ile  Arg Ala Ser Ala Asn  Leu
                995                 1000                1005

gcc gcc acc aag  atg agc gag tgc gtg  ctg ggc cag agc aag  aga      3072
Ala Ala Thr Lys  Met Ser Glu Cys Val  Leu Gly Gln Ser Lys  Arg
            1010                 1015                 1020

gtg gac ttc tgc  ggc aag ggc tac cac  ctg atg agc ttc ccc  cag      3117
Val Asp Phe Cys  Gly Lys Gly Tyr His  Leu Met Ser Phe Pro  Gln
            1025                 1030                 1035

gcc gct ccc cac  ggc gtg gtg ttc ctg  cac gtg acc tac gtg  cct      3162
Ala Ala Pro His  Gly Val Val Phe Leu  His Val Thr Tyr Val  Pro
            1040                 1045                 1050

agc cag gag agg  aat ttc acc acc gcc  cct gcc atc tgc cac  gag      3207
Ser Gln Glu Arg  Asn Phe Thr Thr Ala  Pro Ala Ile Cys His  Glu
            1055                 1060                 1065

ggc aag gcc tac  ttc ccc aga gag ggc  gtg ttc gtg ttc aat  ggc      3252
Gly Lys Ala Tyr  Phe Pro Arg Glu Gly  Val Phe Val Phe Asn  Gly
            1070                 1075                 1080

acc agc tgg ttc  atc acc cag cgg aac  ttc ttc agc ccc cag  atc      3297
Thr Ser Trp Phe  Ile Thr Gln Arg Asn  Phe Phe Ser Pro Gln  Ile
            1085                 1090                 1095

atc aca acc gac  aac acc ttc gtg agc  ggc aac tgc gac gtg  gtg      3342
Ile Thr Thr Asp  Asn Thr Phe Val Ser  Gly Asn Cys Asp Val  Val
            1100                 1105                 1110

atc ggc atc att  aac aat acc gtg tac  gac ccc ctg cag ccc  gag      3387
Ile Gly Ile Ile  Asn Asn Thr Val Tyr  Asp Pro Leu Gln Pro  Glu
            1115                 1120                 1125

ctg gat agc ttc  aag gag gag ctg gac  aag tac ttc aag aac  cac      3432
Leu Asp Ser Phe  Lys Glu Glu Leu Asp  Lys Tyr Phe Lys Asn  His
            1130                 1135                 1140

acc agc ccc gat  gtg gac ttc ggc gac  atc agc ggc atc aat  gcc      3477
Thr Ser Pro Asp  Val Asp Phe Gly Asp  Ile Ser Gly Ile Asn  Ala
            1145                 1150                 1155

agc gtg gtg aac  atc cag aag gag atc  gac cgg ctg aac gag  gtg      3522
Ser Val Val Asn  Ile Gln Lys Glu Ile  Asp Arg Leu Asn Glu  Val
            1160                 1165                 1170

gcc aag aac ctg  aac gag agc ctg atc  gac ctg cag gag ctg  ggc      3567
Ala Lys Asn Leu  Asn Glu Ser Leu Ile  Asp Leu Gln Glu Leu  Gly
            1175                 1180                 1185

aag tac gag cag  tac atc aag tgg ccc  tgg tac gtg tgg ctg  ggc      3612
Lys Tyr Glu Gln  Tyr Ile Lys Trp Pro  Trp Tyr Val Trp Leu  Gly
            1190                 1195                 1200

ttc atc gcc ggc  ctg atc gcc atc gtg  atg gtg acc atc ctg  ctg      3657
Phe Ile Ala Gly  Leu Ile Ala Ile Val  Met Val Thr Ile Leu  Leu
            1205                 1210                 1215

tgc tgc atg acc  agc tgc tgc tcc tgc  ctg aag ggc gcc tgc  agc      3702
Cys Cys Met Thr  Ser Cys Cys Ser Cys  Leu Lys Gly Ala Cys  Ser
            1220                 1225                 1230

tgt ggc agc tgc  tgc aag ttc gac gag  gac gat agc gag ccc  gtg      3747
Cys Gly Ser Cys  Cys Lys Phe Asp Glu  Asp Asp Ser Glu Pro  Val
            1235                 1240                 1245

ctg aag ggc gtg  aag ctg cac tac acc  tga tgaattctcg ag             3789
Leu Lys Gly Val  Lys Leu His Tyr Thr
            1250                 1255
```

<210> SEQ ID NO 115
<211> LENGTH: 1255
<212> TYPE: PRT

<213> ORGANISM: Artificial sequence
<220> FEATURE:
<223> OTHER INFORMATION: S protein of SARS-CoV strain Frankfurt 1

<400> SEQUENCE: 115

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400
```

```
Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655

Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
```

```
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065

Ala Tyr  Phe Pro Arg Glu Gly  Val Phe Val Phe Asn  Gly Thr Ser
    1070                1075                1080

Trp Phe  Ile Thr Gln Arg Asn  Phe Phe Ser Pro Gln  Ile Ile Thr
    1085                1090                1095

Thr Asp  Asn Thr Phe Val Ser  Gly Asn Cys Asp Val  Val Ile Gly
    1100                1105                1110

Ile Ile  Asn Asn Thr Val Tyr  Asp Pro Leu Gln Pro  Glu Leu Asp
    1115                1120                1125

Ser Phe  Lys Glu Glu Leu Asp  Lys Tyr Phe Lys Asn  His Thr Ser
    1130                1135                1140

Pro Asp  Val Asp Phe Gly Asp  Ile Ser Gly Ile Asn  Ala Ser Val
    1145                1150                1155

Val Asn  Ile Gln Lys Glu Ile  Asp Arg Leu Asn Glu  Val Ala Lys
    1160                1165                1170

Asn Leu  Asn Glu Ser Leu Ile  Asp Leu Gln Glu Leu  Gly Lys Tyr
    1175                1180                1185

Glu Gln  Tyr Ile Lys Trp Pro  Trp Tyr Val Trp Leu  Gly Phe Ile
    1190                1195                1200

Ala Gly  Leu Ile Ala Ile Val  Met Val Thr Ile Leu  Leu Cys Cys
    1205                1210                1215

Met Thr  Ser Cys Cys Ser Cys  Leu Lys Gly Ala Cys  Ser Cys Gly
    1220                1225                1230
```

```
Ser Cys  Cys Lys Phe Asp Glu  Asp Asp Ser Glu Pro  Val Leu Lys
    1235                1240                1245

Gly Val  Lys Leu His Tyr Thr
    1250                1255


<210> SEQ ID NO 116
<211> LENGTH: 32
<212> TYPE: DNA
<213> ORGANISM: Artificial sequence
<220> FEATURE:
<223> OTHER INFORMATION: Primer EcoRIspikeFor318

<400> SEQUENCE: 116

cctggaattc tccatggcca acatcaccaa cc                                   32


<210> SEQ ID NO 117
<211> LENGTH: 27
<212> TYPE: DNA
<213> ORGANISM: Artificial sequence
<220> FEATURE:
<223> OTHER INFORMATION: Primer XbaIspikeRev510

<400> SEQUENCE: 117

gaagggccct ctagacacgg tggcagg                                         27


<210> SEQ ID NO 118
<211> LENGTH: 21
<212> TYPE: DNA
<213> ORGANISM: Artificial sequence
<220> FEATURE:
<223> OTHER INFORMATION: Region of S protein
<220> FEATURE:
<221> NAME/KEY: CDS
<222> LOCATION: (1)..(21)
<223> OTHER INFORMATION: Region of S protein

<400> SEQUENCE: 118

cct ttc tcc cct gat ggc aaa                                           21
Pro Phe Ser Pro Asp Gly Lys
1               5


<210> SEQ ID NO 119
<211> LENGTH: 7
<212> TYPE: PRT
<213> ORGANISM: Artificial sequence
<220> FEATURE:
<223> OTHER INFORMATION: Region of S protein

<400> SEQUENCE: 119

Pro Phe Ser Pro Asp Gly Lys
1               5


<210> SEQ ID NO 120
<211> LENGTH: 21
<212> TYPE: DNA
<213> ORGANISM: Artificial sequence
<220> FEATURE:
<223> OTHER INFORMATION: Region of S protein
<220> FEATURE:
<221> NAME/KEY: CDS
<222> LOCATION: (1)..(21)
<223> OTHER INFORMATION: Region of S protein

<400> SEQUENCE: 120

cct ttc tcc ctt gat ggc aaa                                           21
Pro Phe Ser Leu Asp Gly Lys
1               5
```

<210> SEQ ID NO 121
<211> LENGTH: 7
<212> TYPE: PRT
<213> ORGANISM: Artificial sequence
<220> FEATURE:
<223> OTHER INFORMATION: Region of S protein

<400> SEQUENCE: 121

Pro Phe Ser Leu Asp Gly Lys
1               5

<210> SEQ ID NO 122
<211> LENGTH: 23
<212> TYPE: DNA
<213> ORGANISM: Artificial sequence
<220> FEATURE:
<223> OTHER INFORMATION: forward primer Actin-LF

<400> SEQUENCE: 122
cccaaggcca accgcgagaa gat 23

<210> SEQ ID NO 123
<211> LENGTH: 21
<212> TYPE: DNA
<213> ORGANISM: Artificial sequence
<220> FEATURE:
<223> OTHER INFORMATION: reverse primer Actin-LR

<400> SEQUENCE: 123
gtcccggcca gccaggtcca g 21

<210> SEQ ID NO 124
<211> LENGTH: 17
<212> TYPE: DNA
<213> ORGANISM: Artificial sequence
<220> FEATURE:
<223> OTHER INFORMATION: forward primer coro3

<400> SEQUENCE: 124
tacacacctc agcgttg 17

<210> SEQ ID NO 125
<211> LENGTH: 16
<212> TYPE: DNA
<213> ORGANISM: Artificial sequence
<220> FEATURE:
<223> OTHER INFORMATION: reverse primer coro4

<400> SEQUENCE: 125
cacgaacgtg acgaat 16

<210> SEQ ID NO 126
<211> LENGTH: 20
<212> TYPE: PRT
<213> ORGANISM: Artificial sequence
<220> FEATURE:
<223> OTHER INFORMATION: Peptide

<400> SEQUENCE: 126

Ala Thr Ser Thr Gly Asn Tyr Asn Tyr Lys Tyr Arg Tyr Leu Arg His
1               5                   10                  15

Gly Lys Leu Arg
            20

<210> SEQ ID NO 127
<211> LENGTH: 20
<212> TYPE: PRT

-continued

<213> ORGANISM: Artificial sequence
<220> FEATURE:
<223> OTHER INFORMATION: Peptide

<400> SEQUENCE: 127

Tyr Thr Thr Thr Gly Ile Gly Tyr Gln Pro Tyr Arg Val Val Val Leu
1 5 10 15

Ser Phe Glu Leu
20

<210> SEQ ID NO 128
<211> LENGTH: 11
<212> TYPE: PRT
<213> ORGANISM: Artificial sequence
<220> FEATURE:
<223> OTHER INFORMATION: Peptide
<220> FEATURE:
<221> NAME/KEY: MISC_FEATURE
<222> LOCATION: (2)..(2)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be any amino acid
<220> FEATURE:
<221> NAME/KEY: MISC_FEATURE
<222> LOCATION: (6)..(6)
<223> OTHER INFORMATION: Xaa can be any amino acid
<220> FEATURE:
<221> NAME/KEY: MISC_FEATURE
<222> LOCATION: (7)..(7)
<223> OTHER INFORMATION: Xaa can be any amino acid
<220> FEATURE:
<221> NAME/KEY: MISC_FEATURE
<222> LOCATION: (8)..(8)
<223> OTHER INFORMATION: Xaa can be any amino acid
<220> FEATURE:
<221> NAME/KEY: MISC_FEATURE
<222> LOCATION: (9)..(9)
<223> OTHER INFORMATION: Xaa can be any amino acid

<400> SEQUENCE: 128

Thr Xaa Thr Gly Xaa Xaa Xaa Xaa Xaa Tyr Arg
1 5 10

<210> SEQ ID NO 129
<211> LENGTH: 9
<212> TYPE: PRT
<213> ORGANISM: Artificial sequence
<220> FEATURE:
<223> OTHER INFORMATION: LCDR3 of SC03-014

<400> SEQUENCE: 129

Gln Gln Ser Tyr Ser Thr Pro Pro Thr
1 5

<210> SEQ ID NO 130
<211> LENGTH: 5
<212> TYPE: PRT
<213> ORGANISM: Artificial sequence
<220> FEATURE:
<223> OTHER INFORMATION: HCDR1 of SC03-014

<400> SEQUENCE: 130

Asp His Tyr Met Asp
1 5

<210> SEQ ID NO 131
<211> LENGTH: 19
<212> TYPE: PRT
<213> ORGANISM: Artificial sequence
<220> FEATURE:
<223> OTHER INFORMATION: HCDR2 of SC03-014

<400> SEQUENCE: 131

Arg Thr Arg Asn Lys Ala Asn Ser Tyr Thr Thr Glu Tyr Ala Ala Ser
1 5 10 15

Val Lys Gly

<210> SEQ ID NO 132
<211> LENGTH: 11
<212> TYPE: PRT
<213> ORGANISM: Artificial sequence
<220> FEATURE:
<223> OTHER INFORMATION: LCDR1 of SC03-014

<400> SEQUENCE: 132

Arg Ala Ser Gln Ser Ile Ser Ser Tyr Leu Asn
1 5 10

<210> SEQ ID NO 133
<211> LENGTH: 7
<212> TYPE: PRT
<213> ORGANISM: Artificial sequence
<220> FEATURE:
<223> OTHER INFORMATION: LCDR2 of SC03-014

<400> SEQUENCE: 133

Ala Ala Ser Ser Leu Gln Ser
1 5

<210> SEQ ID NO 134
<211> LENGTH: 9
<212> TYPE: PRT
<213> ORGANISM: Artificial sequence
<220> FEATURE:
<223> OTHER INFORMATION: LCDR3 of SC03-022

<400> SEQUENCE: 134

Gln Gln Tyr Tyr Ser Thr Pro Tyr Thr
1 5

<210> SEQ ID NO 135
<211> LENGTH: 5
<212> TYPE: PRT
<213> ORGANISM: Artificial sequence
<220> FEATURE:
<223> OTHER INFORMATION: HCDR1 of SC03-022

<400> SEQUENCE: 135

Thr Tyr Trp Ile Gly
1 5

<210> SEQ ID NO 136
<211> LENGTH: 17
<212> TYPE: PRT
<213> ORGANISM: Artificial sequence
<220> FEATURE:
<223> OTHER INFORMATION: HCDR2 of SC03-022

<400> SEQUENCE: 136

Ile Ile Tyr Pro Gly Asp Ser Glu Thr Arg Tyr Ser Pro Ser Phe Gln
1 5 10 15

Gly

<210> SEQ ID NO 137
<211> LENGTH: 17

-continued

```
<212> TYPE: PRT
<213> ORGANISM: Artificial sequence
<220> FEATURE:
<223> OTHER INFORMATION: LCDR1 of SC03-022

<400> SEQUENCE: 137

Lys Ser Ser Gln Ser Val Leu Tyr Ser Ser Ile Asn Lys Asn Tyr Leu
1               5                   10                  15

Ala


<210> SEQ ID NO 138
<211> LENGTH: 7
<212> TYPE: PRT
<213> ORGANISM: Artificial sequence
<220> FEATURE:
<223> OTHER INFORMATION: LCDR2 of SC03-022

<400> SEQUENCE: 138

Trp Ala Ser Thr Arg Glu Ser
1               5
```

COMPOSITIONS AGAINST SARS-CORONAVIRUS AND USES THEREOF

CROSS-REFERENCE TO RELATED APPLICATIONS

This is a national phase entry under 35 U.S.C. §371 of International Patent Application PCT/EP2005/055876, filed Nov. 10, 2005, published in English as International Patent Publication WO 2006/051091 A1 on May 18, 2006, which claims the benefit under 35 U.S.C. §119 of European Patent Application Serial No. 05107288.2 filed on Aug. 8, 2005, which claims priority to European Patent Application Serial No. 05102117.8 filed on Mar. 17, 2005, which claims priority to European Patent Application Serial No. 04106192.0 filed on Nov. 30, 2004, which claims priority to U.S. Provisional Patent Application Ser. No. 60/627,773, filed Nov. 11, 2004, and to European Patent Application Serial No. 04105684.7, filed Nov. 11, 2004.

TECHNICAL FIELD

The invention relates to medicine. In particular, the invention relates to compositions comprising binding molecules capable of specifically binding to and neutralizing SARS-coronavirus (SARS-CoV). The compositions are useful in the diagnosis of SARS-CoV and the prophylaxis and/or treatment of a condition resulting from SARS-CoV.

BACKGROUND

Recently a new and, in several cases, deadly clinical syndrome was observed in the human population, now called severe acute respiratory syndrome (SARS) (Holmes, 2003). The syndrome is caused by a novel coronavirus (Ksiazek et al., 2003), referred to as the SARS-CoV. The genome sequence of SARS-CoV has been determined (Rota et al., 2003; Marra et al., 2003). However, much remains to be learned about this virus, and means and methods for diagnostics, prophylaxis and/or treatment of the virus and the syndrome are needed. The present invention provides means and methods for use in diagnostics, prevention and/or treatment of SARS-CoV.

SUMMARY OF THE INVENTION

The following definitions of terms are used in the invention.

DEFINITIONS

Binding Molecule

As used herein, the term “binding molecule” refers to an intact immunoglobulin including monoclonal antibodies, such as chimeric, humanized or human monoclonal antibodies, or to an antigen-binding and/or variable domain-comprising fragment of an immunoglobulin that competes with the intact immunoglobulin for specific binding to the binding partner of the immunoglobulin, e.g., the SARS-CoV. Regardless of structure, the antigen-binding fragment binds with the same antigen that is recognized by the intact immunoglobulin. An antigen-binding fragment can comprise a peptide or polypeptide comprising an amino acid sequence of at least two contiguous amino acid residues, at least five contiguous amino acid residues, at least ten contiguous amino acid residues, at least 15 contiguous amino acid residues, at least 20 contiguous amino acid residues, at least 25 contiguous amino acid residues, at least 30 contiguous amino acid residues, at least 35 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of the binding molecule.

The term “binding molecule,” as used herein, includes all immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

Antigen-binding fragments include, inter alia, Fab, F(ab'), $F(ab')_2$, Fv, dAb, Fd, complementarity-determining region (CDR) fragments, single-chain antibodies (scFv), bivalent single-chain antibodies, single-chain phage antibodies, diabodies, triabodies, tetrabodies, or (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in *Antibodies: A Laboratory Manual*, edited by E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule but can also be part of an immunoconjugate. A naked or unconjugated binding molecule is intended to refer to a binding molecule that is not conjugated, operatively linked or otherwise physically or functionally associated with an effector moiety or tag, such as inter alia, a toxic substance, a radioactive substance, a liposome, or an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some of such interactions are necessary in order to exert a biological effect.

Biological Sample

As used herein, the term “biological sample” encompasses a variety of sample types, including blood and other liquid samples of biological origin, solid tissue samples such as a biopsy specimen or tissue cultures, or cells derived therefrom and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

Complementarity-Determining Regions (CDR)

The term "complementarity-determining regions," as used herein, means sequences within the variable regions of binding molecules, such as immunoglobulins, that usually contribute to a large extent to the antigen binding site, which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post-translational modifications of proteins.

Expression-Regulating Nucleic Acid Sequence

The term "expression-regulating nucleic acid sequence," as used herein, refers to polynucleotide sequences necessary for and/or affecting the expression of an operably linked coding sequence in a particular host organism. The expression-regulating nucleic acid sequences (such as inter alia, appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and, when desired, sequences that enhance protein secretion) can be any nucleic acid sequence showing activity in the host organism of choice and can be derived from genes encoding proteins, which are either homologous or heterologous to the host organism. The identification and employment of expression-regulating sequences is routine to the person skilled in the art.

Functional Variant

The term "functional variant," as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner, e.g., SARS-CoV, with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis, and may comprise natural as well as non-natural nucleotides and amino acids.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cystine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). It will be clear to the skilled artisan that other classifications of amino acid residue families than the ones used above can also be employed. Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

Host

The term "host," as used herein, is intended to refer to an organism or a cell into which a vector, such as a cloning vector or an expression vector, has been introduced. The organism or cell can be prokaryotic or eukaryotic. It should be understood that this term is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

Human

The term "human," when applied to binding molecules as defined herein, refers to molecules that are either directly derived from a human or based upon a human sequence. When a binding molecule is derived from or based on a human sequence and subsequently modified, it is still to be considered human as used throughout the specification. In other words, the term "human," when applied to binding molecules, is intended to include binding molecules having variable and constant regions derived from human germline immunoglobulin sequences based on variable or constant regions either occurring or not occurring in a human or human lymphocyte or in modified form. Thus, the human binding molecules may include amino acid residues not encoded by human germline immunoglobulin sequences, comprise substitutions and/or deletions (e.g., mutations introduced by, for instance, random or site-specific mutagenesis in vitro or by somatic mutation in vivo).

"Based on," as used herein, refers to the situation that a nucleic acid sequence may be exactly copied from a template, or with minor mutations, such as by error-prone PCR methods, or synthetically made matching the template exactly or with minor modifications. Semisynthetic molecules based on human sequences are also considered to be human as used herein.

Isolated

The term "isolated," when applied to binding molecules as defined herein, refers to binding molecules that are substantially free of other proteins or polypeptides, particularly free of other binding molecules having different antigenic specificities, and are also substantially free of other cellular material and/or chemicals. For example, when the binding molecules are recombinantly produced, they are preferably substantially free of culture medium, and when the binding molecules are produced by chemical synthesis, they are preferably substantially free of chemical precursors or other chemicals, i.e., they are separated from chemical precursors or other chemicals that are involved in the synthesis of the protein. The term "isolated," when applied to nucleic acid molecules encoding binding molecules as defined herein, is intended to refer to nucleic acid molecules in which the nucleotide sequences encoding the binding molecules are free of other nucleotide sequences, particularly nucleotide sequences encoding binding molecules that bind binding partners other than SARS-CoV. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as cDNA molecules, can be substantially free of other cellular material or culture medium when produced by recombinant techniques, or substantially free of chemical precursors or other chemicals when chemically synthesized.

Monoclonal Antibody

The term "monoclonal antibody," as used herein, refers to a preparation of antibody molecules of single molecular composition. A monoclonal antibody displays a single binding specificity and affinity for a particular epitope. Accordingly, the term "human monoclonal antibody" refers to an antibody displaying a single binding specificity that has variable and constant regions derived from or based on human germline immunoglobulin sequences or derived from completely synthetic sequences. The method of preparing the monoclonal antibody is not relevant.

Nucleic Acid Molecule

The term "nucleic acid molecule," as used in the present invention, refers to a polymeric form of nucleotides and includes both sense and antisense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplexed, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers.

Operably Linked

The term "operably linked" refers to two or more nucleic acid sequence elements that are usually physically linked and are in a functional relationship with each other. For instance, a promoter is operably linked to a coding sequence if the promoter is able to initiate or regulate the transcription or expression of a coding sequence, in which case, the coding sequence should be understood as being "under the control of" the promoter.

Pharmaceutically Acceptable Excipient

By "pharmaceutically acceptable excipient" is meant any inert substance that is combined with an active molecule, such as a drug, agent, or binding molecule, for preparing an agreeable or convenient dosage form. The "pharmaceutically acceptable excipient" is an excipient that is non-toxic to recipients at the dosages and concentrations employed and is compatible with other ingredients of the formulation comprising the drug, agent or binding molecule.

Specifically Binding

The term "specifically binding," as used herein in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules or organisms. The binding may be mediated by covalent or non-covalent interactions or a combination of both. In yet other words, the term "specifically binding" means immunospecifically binding to an antigen or a fragment thereof and not immunospecifically binding to other antigens. A binding molecule that immunospecifically binds to an antigen may bind to other peptides or polypeptides with lower affinity as determined by, e.g., radioimmunoassays (RIA), enzyme-linked immunosorbent assays (ELISA), BIACORE, or other assays known in the art. Binding molecules or fragments thereof that immunospecifically bind to an antigen may be cross-reactive with related antigens. Preferably, binding molecules or fragments thereof that immunospecifically bind to an antigen do not cross-react with other antigens.

Therapeutically Effective Amount

The term "therapeutically effective amount" refers to an amount of the binding molecule, as defined herein, that is effective for preventing, ameliorating and/or treating a condition resulting from infection with SARS-CoV.

Treatment

The term "treatment" refers to therapeutic treatment as well as prophylactic or preventative measures to cure or halt or at least retard disease progress. Those in need of treatment include those already inflicted with a condition resulting from infection with SARS-CoV, as well as those in which infection with SARS-CoV is to be prevented. Subjects partially or totally recovered from infection with SARS-CoV might also be in need of treatment. Prevention encompasses inhibiting or reducing the spread of SARS-CoV or inhibiting or reducing the onset, development or progression of one or more of the symptoms associated with infection with SARS-CoV.

Vector

The term "vector" denotes a nucleic acid molecule into which a second nucleic acid molecule can be inserted for introduction into a host where it will be replicated and in some cases expressed. In other words, a vector is capable of transporting a nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome.

Provided are compositions of binding molecules capable of specifically binding to SARS-CoV and having SARS-CoV-neutralizing activity. In a preferred embodiment, the binding molecules are human binding molecules. The invention further provides for the use of the compositions of the invention in the prophylaxis and/or treatment of a subject having, or at risk of developing, a condition resulting from SARS-CoV. Besides that, the invention pertains to the use of the compositions of the invention in the diagnosis/detection of SARS-CoV.

In a first aspect, the present invention encompasses compositions comprising at least two binding molecules. In one embodiment, the binding molecules are immunoglobulins. Fragments of immunoglobulins still having the desired functionality and/or activity of the complete immunoglobulin are also considered immunoglobulins according to the invention. Preferably, the at least two binding molecules, e.g., immunoglobulins, are capable of specifically binding to a coronavirus. Coronaviruses include, but are not limited to, avian infectious bronchitis virus, avian infectious laryngotracheitis virus, enteric coronavirus, equine coronavirus, coronavirus Group 1 species such as human coronavirus 229E or human coronavirus NL63, coronavirus Group 2 species such as human coronavirus OC43 or chicken enteric coronavirus, coronavirus Group 3 species, human enteric coronavirus 4408, and SARS-CoV. The compositions can be administered to a mammal to treat, prevent or ameliorate one or more symptoms associated with a coronavirus infection.

In one embodiment, the invention relates to synergistic compositions, i.e., compositions exhibiting synergistic coronavirus-neutralizing activity. In other words, the compositions comprise at least two binding molecules, i.e., immunoglobulins, that are capable of specifically binding to a coronavirus and that have coronavirus-neutralizing activity, characterized in that the binding molecules act synergistically in neutralizing coronavirus. As used herein, the term "synergistic" means that the combined effect of the binding molecules when used in combination is greater than their additive effects when used individually. In other words, the neutralizing activity of the composition is greater than the sum of the neutralizing activity of each immunoglobulin alone. In one embodiment, none of the binding molecules, i.e., immunoglobulins, present in the synergistic coronavirus-neutralizing activity-exhibiting compositions may have coronavirus-neutralizing activity when used as an individual binding molecule. Alternatively, one binding molecule of the at least two binding molecules in the compositions exhibiting synergistic coronavirus-neutralizing activity may have coronavirus-neutralizing activity when used individually. In a preferred embodiment, both of the at least two binding molecules, i.e., immunoglobulins, have coronavirus-neutralizing activity when used individually. In one embodiment, one of the at least two binding molecules in the synergistic coronavirus-neutralizing activity-exhibiting compositions may bind to a coronavirus and the other binding molecule may bind to a cell-associated receptor of the coronavirus. Alternatively, both binding molecules may bind to either the coronavirus or cell-associated receptor.

In a preferred embodiment of the invention, the coronavirus is a SARS-CoV including animal or human SARS-CoV. Preferably, the SARS-CoV is a human SARS-CoV. In another aspect, the invention thus provides compositions comprising at least two binding molecules, e.g., immunoglobulins, capable of specifically binding to SARS-CoV and preferably having SARS-Co V-neutralizing activity. The compositions preferably exhibit synergistic SARS-CoV-neutralizing activity. In other words, the compositions comprise at least two binding molecules, e.g., immunoglobulins, having SARS-CoV-neutralizing activity, characterized in that the binding molecules act synergistically in neutralizing SARS-CoV. The SARS-CoV-neutralizing activity of the composition is greater than the sum of the neutralizing activity of each immunoglobulin alone. In a preferred embodiment of the invention, the binding molecules in the compositions act synergistically in neutralizing a plurality of SARS-CoV strains (see Table 1 for a list of several known SARS-CoV genome sequences and S protein genes). In another embodiment, each of the immunoglobulins in the composition is capable of neutralizing a plurality of (different) SARS-CoV strains, preferably human SARS-CoV strains. In another embodiment, at least one of the binding molecules, e.g., immunoglobulins, of the compositions of the invention is capable of neutralizing an animal SARS-CoV. The binding molecules in the compositions of the invention may neutralize coronavirus infectivity, such as SARS-CoV infectivity, by several modes of action including, but not limited to, preventing the attachment of the coronavirus to possible receptors on host cells, inhibition of the release of RNA into the cytoplasm of the cell, prevention of RNA transcription or translation, or inhibition or down-regulation of coronavirus replication. Furthermore, the binding molecules may act by fixing complement or be capable of assisting in the lysis of enveloped coronavirus. They might also act as opsonins and augment phagocytosis of coronavirus, either by promoting its uptake via Fc or C3b receptors or by agglutinating the coronavirus to make it more easily phagocytosed. The binding molecules in the compositions may have similar modes of action or may have different modes of action. In a specific embodiment, the compositions neutralize coronavirus, such as SARS-CoV, infectivity by at least 10%, at least 20%, at least 30%, at least 40%, at least 50%, at least 60%, at least 70%, at least 80%, at least 90%, at least 95%, or at least 99% relative to infection of host cells by the coronavirus in the absence of the compositions. Assays for measuring virus-neutralizing activity are known to the skilled person. Examples of such assays are described below.

The binding molecules, e.g., immunoglobulins, in the compositions of the invention may be capable of specifically binding to a coronavirus, such as SARS-CoV, in activated or inactivated/attenuated form. Methods for inactivating/attenuating viruses are well known in the art and include, but are not limited to, heat inactivation, inactivation by UV irradiation, or inactivation by gamma irradiation. The binding molecules may also be capable of specifically binding to one or more fragments of the coronavirus including inter alia a preparation of one or more proteins and/or (poly)peptides derived from the coronavirus. Preferably, the fragment at least comprises an antigenic determinant recognized by the binding molecules of the invention. An "antigenic determinant," as used herein, is a moiety, such as a coronavirus (such as SARS-CoV), (poly)peptide, protein, glycoprotein, analog or fragment thereof, that is capable of binding to a binding molecule of the invention with sufficiently high affinity to form a detectable antigen-binding molecule complex.

In one embodiment, the binding molecules, i.e., immunoglobulins, are capable of specifically binding to surface-accessible proteins of a coronavirus, which include, but are not limited to, inner and outer membrane proteins, proteins adhering to the cell wall, and potential secreted proteins. Relevant proteins of SARS-CoV in that respect are inter alia the spike (S) protein, the membrane (matrix) protein, the (small) envelope protein, Orf 3, Orf 4, Orf 7, Orf 8, Orf 9, Orf 10 and Orf 14. The amino acid sequence of proteins and potential proteins of various known strains of coronaviruses, such as SARS-CoV, can be found in the EMBL-database and/or other databases. For instance, the complete genome of the SARS coronavirus Urbani can be found in the EMBL-database under accession number AY278741, the complete genome of the SARS coronavirus HSR 1 can be found under accession number AY323977, the complete genome of the SARS coronavirus Frankfurt 1 can be found under accession number AY291315 and the complete genome of the SARS coronavirus TOR2 can be found under accession number AY274119.

In one embodiment, at least one of the binding molecules, e.g., immunoglobulins, in the compositions of the invention is capable of specifically binding to the S protein of SARS-CoV. The other binding molecule may bind to a receptor of SARS-CoV present on or associated with target cells. An example of such a receptor is the ACE-2 receptor (see Li et al., 2003). In another embodiment, all binding molecules in the compositions of the invention are capable of specifically binding to the S protein of SARS-CoV.

In yet another embodiment, at least one of the binding molecules in the compositions of the invention is capable of specifically binding to the extracellular domain of the S protein of SARS-CoV. This domain consists of amino acids 15-1195 of the S protein. In a specific embodiment, at least one binding molecule in the compositions of the invention is capable of specifically binding to amino acids 318-510 of the S protein of SARS-CoV. The neutralizing binding molecules, e.g., immunoglogulins, in the compositions of the invention may react with overlapping, competing epitopes, but preferably they react with different/distinct, non-competing epitopes of the coronavirus, such as SARS-CoV.

Another aspect of the invention are compositions comprising at least two binding molecules capable of specifically binding to a coronavirus, such as SARS-CoV, wherein the binding molecules are capable of reacting with different, non-competing epitopes of the coronavirus. Preferably, the coronavirus is a human coronavirus, more preferably the coronavirus is SARS-CoV. Compositions comprising at least two binding molecules wherein each binding molecule binds to a different epitope or site on a virus are more suitable for preventing the escape of resistant variants of the virus compared to compositions comprising at least two binding molecules wherein each binding molecule binds to an overlapping epitope or site on the virus.

In a specific embodiment, the different, non-competing epitopes recognized by the binding molecules, e.g., immunoglobulins, in the compositions of the invention are located on the S protein of SARS-CoV, particularly the extracellular domain of the S protein, more particularly within amino acids 318-510 of the S protein. In another aspect, at least one of the binding e.g., immunoglobulins, of the compositions of the invention is capable of reacting with amino acids 318-510 of the S protein of a human and an animal SARS-CoV. In another embodiment, at least one of the binding molecules, e.g., immunoglobulins, of the compositions of the invention reacts with an epitope comprising the amino acid sequence of SEQ ID NO:128. The epitope may consist of 11, 11 to 15, 11 to 20, 11 to 25, 11 to 30, 11 to 35, 11 to 40, 11 to 45 or even more amino acids. In another aspect, at least one of the binding molecules, e.g., immunoglobulins, in the compositions of the invention is capable of reacting with amino acids 318-510 of the S protein of a SARS-CoV, wherein the amino acid at position 479 is an amino acid other than asparagine, to a similar extent as with amino acids 318-510 of the S protein of a SARS-CoV, wherein the amino acid at position 479 is an asparagine. In other words, substitution of the amino acid at position 479 does not dramatically influence the binding of at least one of the immunoglobulins in the compositions of the invention to amino acids 318-510 of the S protein of SARS-CoV. "To a similar extent" as defined above means that the binding molecule binds to amino acids 318-510 of the S protein of a SARS-CoV, wherein the amino acid at position 479 is an amino acid other than asparagines, in an amount of at least 60%, at least 70%, at least 75%, at least 80%, at least 85%, at least 90%, at least 95%, preferably at least 100%, compared to the binding of the binding molecule to amino acids 318-510 of the S protein of a SARS-CoV, wherein the amino acid at position 479 is an asparagine. Binding can be measured by methods well known to a person skilled in the art, for instance, by ELISA.

The binding molecules in the compositions according to the invention are preferably human binding molecules, e.g., immunoglobulins. They can be intact immunoglobulin molecules, such as polyclonal or monoclonal antibodies, in particular, human monoclonal antibodies, or the binding molecules can be antigen-binding fragments including, but not limited to, Fab, F(ab'), $F(ab')_2$, Fv, dAb, Fd, complementarity-determining region (CDR) fragments, single-chain antibodies (scFv), bivalent single-chain antibodies, single-chain phage antibodies, diabodies, triabodies, tetrabodies, and (poly)peptides that contain at least a fragment of an immunoglobulin that is sufficient to confer specific antigen binding to the SARS-CoV or fragment thereof. The human binding molecules are preferably human monoclonal antibodies. The binding molecules in the compositions can be in non-isolated or isolated form. The compositions may further comprise at least one other therapeutic agent. Preferably, the therapeutic agent is useful in the prophylaxis and/or treatment of a condition resulting from a coronavirus such as SARS-CoV.

Typically, binding molecules can bind to their binding partners, i.e., a coronavirus or fragments thereof, with an affinity constant (IQ-value) that is lower than $0.2*10^{-4}$ M, $1.0*10^{-5}$ M, $1.0*10^{-6}$ M, $1.0*10^{-7}$ M, preferably lower than $1.0*10^{-8}$ M, more preferably lower than $1.0*10^{-9}$ M, more preferably lower than $1.0*10^{-10}$ M, even more preferably lower than $1.0*10^{-11}$ M, and, in particular, lower than $1.0*10^{-12}$ M. The affinity constants can vary for antibody isotypes. For example, affinity binding for an IgM isotype refers to a binding affinity of at least about $1.0*10^{-7}$ M. Affinity constants can, for instance, be measured using surface plasmon resonance, i.e., an optical phenomenon that allows for the analysis of real-time biospecific interactions by detection of alterations in protein concentrations within a biosensor matrix, for example, using the BIACORE system (Pharmacia Biosensor AB, Uppsala, Sweden).

The binding molecules may bind to a coronavirus in soluble form, for instance, in a sample, or may bind to a coronavirus bound or attached to a carrier or substrate, e.g., microtiter plates, membranes and beads, etc. Carriers or substrates may be made of glass, plastic (e.g., polystyrene), polysaccharides, nylon, nitrocellulose, or teflon, etc. The surface of such supports may be solid or porous and of any convenient shape. Furthermore, the binding molecules may bind to a coronavirus in purified/isolated or non-purified/non-isolated form.

In a preferred embodiment, the binding molecules, e.g., immunoglobulins, of the compositions according to the invention comprise at least a CDR3 region, preferably a heavy-chain CDR3 region, comprising the amino acid sequence of SEQ ID NO:1 or SEQ ID NO:2. In another embodiment, the binding molecules comprising the heavy-chain CDR3 region of SEQ ID NO:1 further comprise a light-chain CDR3 region comprising the amino acid sequence of SEQ ID NO:129. In another embodiment, the binding molecules comprising the heavy-chain CDR3 region of SEQ ID NO:1 further comprise a heavy-chain CDR1, heavy-chain CDR2, light-chain CDR1 and light-chain CDR2 region comprising the amino acid sequence of SEQ ID NO:130, SEQ ID NO:131, SEQ ID NO:132, and SEQ ID NO:133, respectively. In another embodiment, the binding molecules comprising the heavy-chain CDR3 region of SEQ ID NO:2 further comprise a light-chain CDR3 region comprising the amino acid sequence of SEQ ID NO:134. In another embodiment, the binding molecules comprising the heavy-chain CDR3 region of SEQ ID NO:2 further comprise a heavy-chain CDR1, heavy-chain CDR2, light-chain CDR1 and light-chain CDR2 region comprising the amino acid sequence of SEQ ID NO:135, SEQ ID NO:136, SEQ ID NO:137, and SEQ ID NO:138, respectively. In yet another embodiment, the binding molecules according to the invention comprise a heavy-chain variable region comprising the amino acid sequence of SEQ ID NO:4 or SEQ ID NO:6. In another embodiment, the binding molecules, i.e., immunoglobulins, in the compositions of the invention comprise at least one CDR region of a binding molecule comprising a heavy-chain variable region comprising the amino acid sequence of SEQ ID NO:4 or SEQ ID NO:6. In another embodiment, they comprise two, three, four, five or even all six CDR regions.

In a further embodiment, the binding molecules according to the invention comprise a heavy-chain variable region comprising the amino acid sequence of SEQ ID NO:4 and a light-chain variable region comprising the amino acid sequence of SEQ ID NO:8, or a heavy-chain variable region comprising the amino acid sequence of SEQ ID NO:6 and a light-chain variable region comprising the amino acid sequence of SEQ ID NO:10.

In a preferred embodiment, the binding molecules having coronavirus, such as SARS-CoV, neutralizing activity are administered in IgG1 or IgA format.

In another aspect, the compositions may comprise at least one functional variant of a binding molecule as defined herein. The compositions may also consist of only functional variants of binding molecules as herein described. Molecules are considered to be functional variants of a binding molecule if the variants are capable of competing for specifically binding to a coronavirus, such as SARS-CoV, or a fragment thereof with the parent binding molecules; in other words, when the functional variants are still capable of binding to the coronavirus, such as SARS-CoV, or a fragment thereof. Preferably, the functional variants are capable of neutralizing coronavirus, such as SARS-CoV, infectivity and should together, with the other binding molecule (or other functional variant) or other binding molecules (or other functional variants), form a composition exhibiting synergistic coronavirus, such as SARS-CoV, neutralizing activity. The neutralizing activity of a functional variant may be either higher or lower compared to the parent binding molecules.

Functional variants include, but are not limited to, derivatives that are substantially similar in primary structural sequence, but that contain, e.g., in vitro or in vivo modifications, chemical and/or biochemical, that are not found in the parent binding molecule. Such modifications are well known to the skilled artisan and include inter alia acetylation, acylation, covalent attachment of a nucleotide or nucleotide derivative, covalent attachment of a lipid or lipid derivative, glycosylation, methylation, pegylation, proteolytic processing, phosphorylation, and the like.

Alternatively, functional variants can be binding molecules as defined in the present invention comprising an amino acid sequence containing substitutions, insertions, deletions or combinations thereof of one or more amino acids compared to the amino acid sequences of the parent binding molecules. Furthermore, functional variants can comprise truncations of the amino acid sequence at either or both the amino or carboxy termini. Functional variants may have the same or different, either higher or lower, binding affinities compared to the parent binding molecule but are still capable of binding to a coronavirus, such as SARS-CoV, or a fragment thereof and preferably still capable of neutralizing coronavirus, such as SARS-CoV, infectivity. For instance, functional variants may have increased or decreased binding affinities for a coronavirus, such as SARS-CoV, or a fragment thereof compared to the parent binding molecules. Preferably, the amino acid sequences of the variable regions, including, but not limited to, framework regions, hypervariable regions, in particular the CDR3 regions, are modified. Generally, the light-chain and the heavy-chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the present invention have at least about 50% to about 99%, preferably at least about 60% to about 99%, more preferably at least about 70% to about 99%, even more preferably at least about 80% to about 99%, most preferably at least about 90% to about 99%, in particular, at least about 95% to about 99%, and in particular, at least about 97% to about 99% amino acid sequence homology with the parent binding molecules as defined herein. Computer algorithms such as inter alia Gap or Bestfit known to a person skilled in the art can be used to optimally align amino acid sequences to be compared and to define similar or identical amino acid residues. Functional variants can be obtained by altering the parent binding molecules or parts thereof by general molecular biology methods known in the art including, but not limited to, error-prone PCR, oligonucleotide-directed mutagenesis and site-directed mutagenesis.

In yet a further aspect, the invention includes compositions comprising at least one immunoconjugate, i.e., a molecule comprising at least one binding molecule or functional variant thereof as defined herein and further comprising at least one tag. Also contemplated in the present invention are compositions consisting of immunoconjugates. The compositions may further comprise another molecule, such as a therapeutic agent or immunoconjugate having a different specificity. In a further embodiment, the immunoconjugates of the invention may comprise more than one tag. These tags can be the same or distinct from each other and can be joined/conjugated non-covalently to the binding molecules. The tag(s) can also be joined/conjugated directly to the binding molecules through covalent bonding. Alternatively, the tag(s) can be joined/conjugated to the binding molecules by means of one or more linking compounds. Techniques for conjugating tags to binding molecules are well known to the skilled artisan.

The tags of the immunoconjugates of the present invention may be therapeutic agents, but preferably they are detectable moieties/agents. Compositions comprising immunoconjugates comprising a detectable agent can be used diagnostically to, for example, assess if a subject has been infected with a coronavirus, such as SARS-CoV, or monitor the development or progression of a coronavirus, such as SARS-CoV, infection as part of a clinical testing procedure to, e.g., determine the efficacy of a given treatment regimen. However, they may also be used for other detection and/or analytical and/or diagnostic purposes. Detectable moieties/agents include, but are not limited to, enzymes, prosthetic groups, fluorescent materials, luminescent materials, bioluminescent materials, radioactive materials, positron emitting metals, and nonradioactive paramagnetic metal ions. The tags used to label the binding molecules for detection and/or analytical and/or diagnostic purposes depend on the specific detection/analysis/diagnosis techniques and/or methods used, such as, inter alia immunohistochemical staining of (tissue) samples, flow cytometric detection, scanning laser cytometric detection, fluorescent immunoassays, enzyme-linked immunosorbent assays (ELISAs), radioimmunoassays (RIAs), bioassays (e.g., neutralization assays), Western blotting applications, etc. For immunohistochemical staining of tissue samples, preferred labels are enzymes that catalyze production and local deposition of a detectable product. Furthermore, the compositions of the invention can also be attached to solid supports, which are particularly useful for in vitro immunoassays or purification of a coronavirus or a fragment thereof. Such solid supports might be porous or nonporous, planar or nonplanar. The binding molecules of the present invention or functional fragments thereof can be fused to marker sequences, such as a peptide, to facilitate purification. Alternatively, an antibody can be conjugated to a second antibody to form an antibody heteroconjugate. In another aspect, the binding molecules of the invention may be conjugated/attached to one or more antigens. Preferably, these antigens are antigens that are recognized by the immune system of a subject to which the binding molecule-antigen conjugate is administered.

Next to producing immunoconjugates chemically by conjugating, directly or indirectly via, for instance, a linker, the immunoconjugates can be produced as fusion proteins comprising the binding molecules of the invention and a suitable tag. Fusion proteins can be produced by methods known in the art such as, e.g., recombinantly by constructing nucleic acid molecules comprising nucleotide sequences encoding the binding molecules in frame with nucleotide sequences encoding the suitable tag(s) and then expressing the nucleic acid molecules.

It is another aspect of the present invention to provide a nucleic acid molecule encoding at least a binding molecule or functional fragment thereof present in the compositions according to the invention. Such nucleic acid molecules can be used as intermediates for cloning purposes, e.g., in the process of affinity maturation described above. In a preferred embodiment, the nucleic acid molecules are isolated or purified.

The skilled man will appreciate that functional variants of these nucleic acid molecules are also intended to be a part of the present invention. Functional variants are nucleic acid sequences that can be directly translated, using the standard genetic code, to provide an amino acid sequence identical to that translated from the parent nucleic acid molecules.

Preferably, the nucleic acid molecules encode binding molecules comprising a CDR3 region, preferably a heavy-chain CDR3 region, comprising the amino acid sequence of SEQ ID NO:1 or SEQ ID NO:2. In another embodiment, the nucleic acid molecules of the invention encode binding molecules comprising a light-chain CDR3 region comprising the amino acid sequence of SEQ ID NO:129 or SEQ ID NO:134. In yet another embodiment, the nucleic acid molecules of the invention encode binding molecules comprising a heavy-chain CDR1 region comprising the amino acid sequence of SEQ ID NO:130 or SEQ ID NO:135; a heavy-chain CDR2 region comprising the amino acid sequence of SEQ ID NO:131 or SEQ ID NO:136; a light-chain CDR1 region comprising the amino acid sequence of SEQ ID NO:132 or SEQ ID NO:137; and/or a light-chain CDR2 region comprising the amino acid sequence of SEQ ID NO:133 or SEQ ID NO:138.

Even more preferably, the nucleic acid molecules encode binding molecules comprising a heavy-chain variable region comprising the amino acid sequence of SEQ ID NO:4 or SEQ ID NO:6.

In yet another embodiment, the nucleic acid molecules encode binding molecules comprising a heavy-chain variable region comprising the amino acid sequence of SEQ ID NO:4 and a light-chain variable region comprising the amino acid sequence of SEQ ID NO:8 or they encode a heavy-chain variable region comprising the amino acid sequence of SEQ ID NO:6 and a light-chain variable region comprising the amino acid sequence of SEQ ID NO:10.

In a specific embodiment of the invention the nucleic acid molecules encoding the heavy-chain variable region of the binding molecules of the invention comprise the nucleotide sequence of SEQ ID NO:3 or SEQ ID NO:5.

In yet another specific embodiment of the present invention, the nucleic acid molecules encoding the light-chain variable region of the binding molecules of the invention comprise the nucleotide sequence of SEQ ID NO:7 or SEQ ID NO:9. The nucleic acid molecules of the invention may even contain the nucleotide sequences or parts thereof of the at least two binding molecules present in the compositions of the invention.

It is another aspect of the invention to provide vectors, i.e., nucleic acid constructs, comprising one or more nucleic acid molecules according to the present invention. Vectors can be derived from plasmids such as inter alia F, R1, RP1, Col, pBR322, TOL, Ti, etc.; cosmids; phages such as lambda, lambdoid, M13, Mu, P1, P22, $Q_{\beta}$, T-even, T-odd, T2, T4, T7, etc.; plant viruses; or animal viruses. Vectors can be used for cloning and/or for expression of the binding molecules of the invention and might even be used for gene therapy purposes. Vectors comprising one or more nucleic acid molecules according to the invention operably linked to one or more expression-regulating nucleic acid molecules are also covered by the present invention. The binding molecules present in the compositions of the invention may be expressed on separate vectors but may also be expressed on the same vector. The choice of the vector(s) is dependent on the recombinant procedures followed and the host used. Introduction of vectors in host cells can be effected by inter alia calcium phosphate transfection, virus infection, DEAE-dextran-mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the binding molecules as described above operably linked to one or more nucleic acid molecules encoding proteins or peptides that can be used to isolate the binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject of the present invention. Preferably, the hosts are host cells. Host cells include, but are not limited to, cells of mammalian, plant, insect, fungal or bacterial origin. Bacterial cells include, but are not limited to, cells from gram-positive bacteria, such as several species of the genera *Bacillus, Streptomyces* and *Staphylococcus*, or cells of gram-negative bacteria, such as several species of the genera *Escherichia*, such as *E. coli*, and *Pseudomonas*. In the group of fungal cells, preferably, yeast cells are used. Expression in yeast can be achieved by using yeast strains, such as inter alia *Pichia pastoris, Saccharomyces cerevisiae* and *Hansenula polymorpha*. Furthermore, insect cells, such as cells from *Drosophila* and Sf9, can be used as host cells. Besides that, the host cells can be plant cells expression systems using mammalian cells, such as Chinese Hamster Ovary (CHO) cells, COS cells, BHK cells or Bowes melanoma cells, are preferred in the present invention. Mammalian cells provide expressed proteins with post-translational modifications that are most similar to natural molecules of mammalian origin. Since the present invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. Preferred mammalian cells are human retina cells, such as 911 cells, or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B.V.). For the purposes of this application, "PER.C6" refers to cells deposited under number 96022940 or ancestors, passages upstream or downstream, as well as descendants from ancestors of deposited cells, as well as derivatives of any of the foregoing. In preferred embodiments, the human producer cells comprise at least a functional part of a nucleic acid sequence encoding an adenovirus E1 region in expressible format. In even more preferred embodiments, the host cells are derived from a human retina and immortalized with nucleic acids comprising adenoviral E1 sequences, such as the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6®, and derivatives thereof. Production of recombinant proteins in host cells can be performed according to methods well known in the art. The use of the cells marketed under the trademark PER.C6® as a production platform for proteins of interest has been described in WO 00/63403, the disclosure of which is incorporated herein by reference in its entirety.

Methods of producing binding molecules or functional variants are well known to the skilled artisan. One method comprises the steps of a) culturing a host as defined above under conditions conducive to the expression of the binding molecules or functional variants, and b) optionally, recovering the expressed binding molecules or functional variants. The expressed binding molecules or functional variants thereof can be recovered from the cell-free extract, but preferably they are recovered from the culture medium. Methods to recover proteins, such as binding molecules, from cell-free extracts or culture medium are well known to the man skilled in the art. Binding molecules or functional variants thereof as obtainable by the above-described method are also a part of the present invention. Alternatively, next to the expression in hosts, such as host cells, the binding molecules or functional variants thereof can be produced synthetically by conventional peptide synthesizers or in cell-free translation systems using RNA nucleic acid derived from DNA molecules according to the invention. Binding molecule or functional variants thereof as obtainable by the above-described synthetic production methods or cell-free translation systems are also a part of the present invention. In yet another alternative embodiment, binding molecules according to the present invention, preferably human binding molecules specifically binding to a coronavirus, such as SARS-CoV, or a fragment thereof, may be generated by transgenic non-human mammals, such as transgenic mice or rabbits, that express human immunoglobulin genes. Preferably, the transgenic non-human mammals have a genome comprising a human heavy-chain transgene and a human light-chain transgene encoding all or a portion of the human binding molecules as described above. The transgenic non-human mammals can be immunized with a purified or enriched preparation of a coronavirus, such as SARS-CoV, or a fragment thereof. Protocols for immunizing non-human mammals are well established in the art. See, *Using Antibodies: A Laboratory Manual*, edited by E. Harlow, D. Lane (1998), Cold Spring Harbor Laboratory, Cold Spring Harbor, N.Y.; and *Current Protocols in Immunology*, edited by J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human binding molecules are produced by B cells or plasma cells derived from the transgenic animals or human subjects that have been exposed to SARS-CoV. In yet another embodiment, the human binding molecules are produced by hybridomas that are prepared by fusion of B cells obtained from the above-described transgenic non-human mammals or human subjects to immortalized cells. B cells, plasma cells and hybridomas as obtainable from the above-described transgenic non-human mammals or human subjects and human binding molecules as obtainable from the above-described transgenic non-human mammals or human subjects are also a part of the present invention.

Methods of identifying binding molecules, preferably human binding molecules such as human monoclonal antibodies or fragments thereof, or nucleic acid molecules encoding the binding molecules, may comprise the steps of a) contacting a phage library of binding molecules, preferably human binding molecules, with a coronavirus, such as SARS-CoV, or a fragment thereof, b) selecting at least one for a phage binding to the coronavirus or the fragment thereof, and c) separating and recovering the phage binding to the coronavirus or the fragment thereof. The selection step may be performed by contacting a phage library with a coronavirus that is inactivated. The coronavirus may be isolated or non-isolated, e.g., present in serum and/or blood of an infected individual. Alternatively, the selection step may be performed in the presence of a fragment of a coronavirus, such as an extracellular part of the coronavirus (such as SARS-CoV), one or more proteins or (poly)peptides derived from a coronavirus, fusion proteins comprising these proteins or (poly) peptides, and the like. Phage display methods for identifying and obtaining binding molecules, e.g., antibodies, are by now well-established methods known by the person skilled in the art. They are, e.g., described in U.S. Pat. No. 5,696,108; Burton and Barbas, 1994; de Kruif et al., 1995b; and *Phage Display: A Laboratory Manual*, edited by C. F. Barbas, D. R. Burton, J. K. Scott and G. J. Silverman (2001), Cold Spring Harbor Laboratory Press, Cold Spring Harbor, N.Y. All these references are herewith incorporated herein in their entirety. For the construction of phage display libraries, collections of human monoclonal antibody heavy- and light-chain variable region genes are expressed on the surface of bacteriophage particles, preferably filamentous bacteriophage particles, in, for example, single-chain Fv (scFv) or in Fab format (see de Kruif et al., 1995b). Large libraries of antibody fragment-expressing phages typically contain more than $1.0*10^9$ antibody specificities and may be assembled from the immunoglobulin V regions expressed in the B lymphocytes of non-immunized or immunized individuals. In a specific embodiment, the phage library of binding molecules, preferably scFv phage library, is prepared from RNA isolated from cells obtained from a subject that has been vaccinated or exposed to a coronavirus, such as SARS-CoV. RNA can be isolated from inter alia bone marrow or peripheral blood, preferably peripheral blood lymphocytes. The subject can be an animal vaccinated or exposed to a coronavirus, but is preferably a human subject that has been vaccinated or has been exposed to a coronavirus. Preferably, the human subject has recovered from the coronavirus.

Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity, e.g., CDR regions. Coronavirus-specific phage antibodies can be selected from libraries by immobilizing a coronavirus (in inactivated or active form) or target antigens, such as antigens from a coronavirus on a solid phase, and subsequently exposing the coronavirus (in inactivated or active form) or target antigens to a phage library to allow binding of phages expressing antibody fragments specific for the solid phase-bound antigen(s). Non-bound phages are removed by washing and bound phages are eluted from the solid phase for infection of *Escherichia coli* (*E. coli*) bacteria and subsequent propagation. Multiple rounds of selection and propagation are usually required to sufficiently enrich for phages binding specifically to the coronavirus (in inactivated or active form) or target antigen(s). If desired, before exposing the phage library to a coronavirus (in inactivated or active form) or target antigens, the phage library can first be subtracted by exposing the phage library to non-target antigens bound to a solid phase. Phages may also be selected for binding to complex antigens, such as complex mixtures of coronavirus proteins or (poly)peptides or host cells expressing one or more proteins or (poly)peptides of a coronavirus. Antigen-specific phage antibodies can be selected from the library by incubating a solid phase with bound thereon a preparation of an inactivated coronavirus with the phage antibody library to allow, for example, the scFv or Fab part of the phage bind to the proteins/polypeptides of the coronavirus preparation. After incubation and several washes to remove unbound and loosely attached phages, the phages that have bound with their scFv or Fab part to the preparation are eluted and used to infect *Escherichia coli* to allow amplification of the new specificity. Generally, one or more selection rounds are required to separate the phages of interest from the large excess of non-binding phages. Alternatively, known proteins or (poly)peptides of the coronavirus can be expressed in host cells and these cells can be used for selection of phage antibodies specific for the proteins or (poly)peptides. A phage display method using these host cells can be extended and improved by subtracting non-relevant binders during screening by addition of an excess of host cells comprising no target molecules or non-target molecules that are similar, but not identical, to the target, and thereby strongly enhance the chance of finding relevant binding molecules (this process is referred to as the Mabstract™ process and is a pending trademark application of Crucell Holland B.V., see also, U.S. Pat. No. 6,265,150, which is incorporated herein by reference). An example of a coronavirus against which binding molecules can be found using the above-described method of identification is SARS-CoV.

A method of obtaining a binding molecule, preferably a human binding molecule or a nucleic acid molecule encoding such a binding molecule, may comprise the steps of a) performing the above-described method of identifying binding molecules, preferably human binding molecules, such as human monoclonal antibodies or fragments thereof, or nucleic acid molecules encoding the binding molecules, and b) isolating from the recovered phage the human binding molecule and/or the nucleic acid encoding the human binding molecule. Once a new monoclonal phage antibody has been established or identified with the above-mentioned method of identifying binding molecules or nucleic acid molecules encoding the binding molecules, the DNA encoding the scFv or Fab can be isolated from the bacteria or phages and combined with standard molecular biological techniques to make constructs encoding bivalent scFvs or complete human immunoglobulins of a desired specificity (e.g., IgG, IgA or IgM). These constructs can be transfected into suitable cell lines and complete human monoclonal antibodies can be produced (see, Huls et al., 1999; Boel et al., 2000).

In addition to the at least two binding molecules, the compositions of the invention may comprise inter alia stabilizing molecules, such as albumin or polyethylene glycol, or salts. Preferably, the salts used are salts that retain the desired biological activity of the binding molecules and do not impart any undesired toxicological effects. Examples of such salts include, but are not limited to, acid addition salts and base addition salts. Acid addition salts include, but are not limited to, those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include, but are not limited to, those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like. If necessary, the binding molecules of the invention may be coated in or on a material to protect them from the action of acids or other natural or non-natural conditions that may inactivate the binding molecules.

In yet a further aspect, provided are compositions comprising at least two nucleic acid molecule encoding binding molecules as defined in the present invention. The compositions may comprise aqueous solutions, such as aqueous solutions containing salts (e.g., NaCl or salts as described above), detergents (e.g., SDS) and/or other suitable components.

Furthermore, the present invention pertains to pharmaceutical compositions comprising a composition according to the invention. The pharmaceutical composition of the invention further comprises at least one pharmaceutically acceptable excipient.

A pharmaceutical composition according to the invention can further comprise at least one other therapeutic, prophylactic and/or diagnostic agent. Preferably, the therapeutic and/or prophylactic agents are agents capable of preventing and/or treating an infection and/or a condition resulting from a coronavirus, such as SARS-CoV. Therapeutic and/or prophylactic agents include, but are not limited to, anti-viral agents. Such agents can be binding molecules, small molecules, organic or inorganic compounds, enzymes, polynucleotide sequences, etc.

Examples of anti-viral agents are well known to the skilled artisan. Agents that are currently used to treat patients infected with, for instance, SARS-CoV, are interferon-alpha, steroids and potential replicase inhibitors. Furthermore, patients infected with SARS-CoV are currently treated by transfusion of serum produced from blood donated by recovering/recovered SARS patients who have produced antibodies after being exposed to the virus. Agents capable of preventing and/or treating an infection with SARS-CoV or other coronavirus and/or a condition resulting from SARS-CoV or other coronavirus that are in the experimental phase might also be used as other therapeutic and/or prophylactic agents useful in the present invention.

The pharmaceutical compositions of the invention can be tested in suitable animal model systems prior to use in humans. Such animal model systems include, but are not limited to, ferrets, mice, rats, chicken, cows, monkeys, pigs, dogs, rabbits, etc.

Typically, pharmaceutical compositions must be sterile and stable under the conditions of manufacture and storage. The compositions of the present invention can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the compositions of the present invention can be in solution and the appropriate pharmaceutically acceptable excipient can be added and/or mixed before or at the time of delivery to provide a unit dosage injectable form. Preferably, the pharmaceutically acceptable excipient used in the present invention is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the compositions of the invention can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the compositions with, or co-administer the compositions with, a material or compound that prevents the inactivation of the binding molecules in the compositions. For example, the binding molecules of the compositions may be administered to a subject in an appropriate carrier, for example, liposomes, or a diluent.

The routes of administration can be divided into two main categories, oral and parenteral administration. These two categories include several routes of administration well known to the skilled person. The preferred administration route is intravenous, particularly preferred is intramuscular.

Oral dosage forms can be formulated in several formulations and may contain pharmaceutically acceptable excipients including, but not limited to, inert diluents, granulating and disintegrating agents, binding agents, lubricating agents, preservatives, coloring, flavoring or sweetening agents, vegetable oils, mineral oils, wetting agents, and thickening agents.

The pharmaceutical compositions of the present invention can also be formulated for parenteral administration. Formulations for parenteral administration can be inter alia in the form of aqueous or non-aqueous isotonic sterile non-toxic injection or infusion solutions or suspensions. The solutions or suspensions may comprise agents that are non-toxic to recipients at the dosages and concentrations employed. Such agents are well known to the skilled artisan and include 1,3-butanediol, Ringer's solution, Hank's solution, isotonic sodium chloride solution, oils or fatty acids, local anesthetic agents, preservatives, buffers, viscosity or solubility increasing agents, water-soluble antioxidants, oil-soluble antioxidants, and metal chelating agents.

In a further aspect, the pharmaceutical compositions of the invention can be used as a medicament. Thus, a method of treatment and/or prevention of a coronavirus infection using the pharmaceutical compositions of the invention is another part of the present invention. The (pharmaceutical) compositions of the invention can inter alia be used in the diagnosis, prophylaxis, treatment, or combination thereof, of one or more conditions resulting from a coronavirus. They are suitable for treatment of yet untreated patients suffering from a condition resulting from a coronavirus and patients who have been or are treated from a condition resulting from a coronavirus. They protect against further infection by a coronavirus and/or will retard the onset or progress of the symptoms associated with a coronavirus. They may even be used in the prophylaxis of conditions resulting from a coronavirus in, for instance, people exposed to the coronavirus such as hospital personnel taking care of suspected patients. Preferably, the (pharmaceutical) compositions can be used in a method to detect, prevent, and/or treat a human coronavirus, such as SARS-CoV, infection.

The above-mentioned compositions and pharmaceutical compositions may be employed in conjunction with other molecules useful in diagnosis, prophylaxis and/or treatment of a coronavirus infection. They can be used in vitro, ex vivo or in vivo. For instance, the pharmaceutical compositions of the invention can be co-administered with a vaccine against a coronavirus, such as SARS-CoV. Alternatively, the vaccine may also be administered before or after administration of the pharmaceutical compositions of the invention. Administration of the pharmaceutical compositions of the invention with a vaccine might be suitable for post-exposure prophylaxis and might also decrease possible side effects of a live-attenuated vaccine in immunocompromised recipients.

The binding molecules are typically formulated in the compositions and pharmaceutical compositions of the invention in a therapeutically or diagnostically effective amount. Dosage regimens can be adjusted to provide the optimum desired response (e.g., a therapeutic response). A suitable dosage range may, for instance, be 0.05-100 mg/kg body weight, preferably 0.1-15 mg/kg body weight.

Typically, the molar ratio of the two binding molecules in the compositions and pharmaceutical compositions of the invention may vary from 1:100 to 100:1, preferably from 1:50 to 50:1, more preferably from 1:25 to 25:1, particularly 1:10 to 10:1, and more particularly 1:5 to 5:1. Furthermore, for example, a single bolus may be administered, several divided doses may be administered over time or the dose may be proportionally reduced or increased as indicated by the exigencies of the therapeutic situation. The molecules and compositions according to the present invention are preferably sterile. Methods to render these molecules and compositions sterile are well known in the art. The other molecules useful in diagnosis, prophylaxis and/or treatment can be administered in a similar dosage regimen as proposed for the binding molecules of the invention. If the other molecules are administered separately, they may be administered to a patient prior to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before), concomitantly with, or subsequent to (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) the administration of one or more of the binding molecules or pharmaceutical compositions of the invention. The exact dosing regimen is usually sorted out during clinical trials in human patients.

Human binding molecules and pharmaceutical compositions comprising the human binding molecules are particularly useful, and often preferred, when they are to be administered to human beings as in vivo therapeutic agents, since recipient immune response to the administered antibody will often be substantially less than that occasioned by administration of a monoclonal murine, chimeric or humanized binding molecule.

In another aspect, the invention concerns the use of (pharmaceutical) compositions according to the invention in the preparation of a medicament for the diagnosis, prophylaxis, treatment, or combination thereof, of a condition resulting from a coronavirus. Preferably, the coronavirus is a human coronavirus, such as SARS-CoV.

Next to that, kits comprising at least one composition according to the invention or at least one pharmaceutical composition according to the invention are also a part of the present invention. Optionally, the above described components of the kits of the invention are packed in suitable containers and labeled for diagnosis, prophylaxis and/or treatment of the indicated conditions. The binding molecules in the (pharmaceutical) compositions may be packaged individually. The above-mentioned components may be stored in unit or multi-dose containers, for example, sealed ampules, vials, bottles, syringes, and test tubes, as an aqueous, preferably sterile, solution or as a lyophilized, preferably sterile, formulation for reconstitution. The containers may be formed from a variety of materials and may have a sterile access port (for example, the container may be an intravenous solution bag or a vial having a stopper pierceable by a hypodermic injection needle). The kit may further comprise more containers comprising a pharmaceutically acceptable buffer. It may further include other materials desirable from a commercial and user standpoint, including other buffers, diluents, filters, needles, syringes, culture medium for one or more of the suitable hosts. Associated with the kits can be instructions customarily included in commercial packages of therapeutic, prophylactic or diagnostic products, that contain information about, for example, the indications, usage, dosage, manufacture, administration, contraindications and/or warnings concerning the use of such therapeutic, prophylactic or diagnostic products.

The invention further pertains to a method of detecting a SARS-CoV in a sample, wherein the method comprises the steps of a) contacting a sample with a diagnostically effective amount of compositions or pharmaceutical compositions according to the invention, and b) determining whether the compositions or pharmaceutical compositions specifically bind to a molecule of the sample. The sample may be a biological sample including, but not limited to, blood, serum, urine, tissue or other biological material from (potentially) infected subjects, or a nonbiological sample, such as water, drink, etc. The (potentially) infected subjects may be human subjects. Animals that are suspected as carriers of a coronavirus, such as SARS-CoV, may also be tested for the presence of the coronavirus using the compositions or pharmaceutical compositions. The sample may first be manipulated to make it more suitable for the method of detection. "Manipulation" means inter alia treating the sample suspected to contain and/or containing the coronavirus in such a way that the coronavirus will disintegrate into antigenic components, such as proteins, (poly)peptides or other antigenic fragments. Preferably, the compositions or pharmaceutical compositions are contacted with the sample under conditions that allow the formation of an immunological complex between the binding molecules in the compositions or pharmaceutical compositions and the coronavirus or antigenic components thereof that may be present in the sample. The formation of an immunological complex, if any, indicating the presence of the coronavirus in the sample, is then detected and measured by suitable means. Such methods include, inter alia, homogeneous and heterogeneous binding immunoassays, such as radioimmunoassays (RIA), ELISA, immunofluorescence, immunohistochemistry, FACS, BIACORE and Western blot analyses.

Preferred assay techniques, especially for large-scale clinical screening of patient sera and blood and blood-derived products, are ELISA and Western blot techniques. ELISA tests are particularly preferred and well known to persons skilled in the art.

In a further aspect, the invention provides a method of screening a binding molecule or a functional variant of a binding molecule for specific binding to a different, non-overlapping epitope of a coronavirus, such as SARS-CoV, as the epitope bound by a binding molecule or functional variant of the invention, wherein the method comprises the steps of a) contacting a binding molecule or a functional variant to be screened, a binding molecule or functional variant of the invention and a coronavirus or fragment thereof, and b) measure if the binding molecule or functional variant to be screened is capable of competing for specifically binding to the coronavirus or fragment thereof with the binding molecule or functional variant of the invention. If the binding molecule or functional variant to be screened is not capable of competing for specifically binding to the coronavirus or fragment thereof with the binding molecule or functional variant of the invention, it most likely binds to a different, non-overlapping epitope. In a further step, it may be determined if the screened binding molecules that bind to a different, non-overlapping epitope compared to the binding molecules of the invention have coronavirus-neutralizing activity. In yet a further step, it can be determined if the screened binding molecules that bind to a different, non-overlapping epitope compared to the binding molecules of the invention and have coronavirus-neutralizing activity, form together with the binding molecules of the invention a composition exhibiting synergistic coronavirus-neutralizing activity. Assays to screen for non-competing binding molecules and measure (synergistic) neutralizing activity are well known to the skilled person.

DESCRIPTION OF THE FIGURES

FIG. 6 shows a competition ELISA for binding to the 5565 fragment.

FIG. 9 shows the comparison of the nucleotide and amino acid sequences of the SARS-CoV wild-type strain (SARS-CoV strain HKU 39849) and escape viruses of antibody CR03-014. Virus-infected cells were harvested two days post-infection and total RNA was isolated. cDNA was generated and used for DNA sequencing. Regions containing mutations are shown and the mutations are indicated in bold. Numbers above amino acids indicate amino acid numbers from S protein including signal peptide. The sequences in FIG. 9 are also represented by SEQ ID NOS:118-121.

DETAILED DESCRIPTION OF THE INVENTION

Examples

Figure 1:
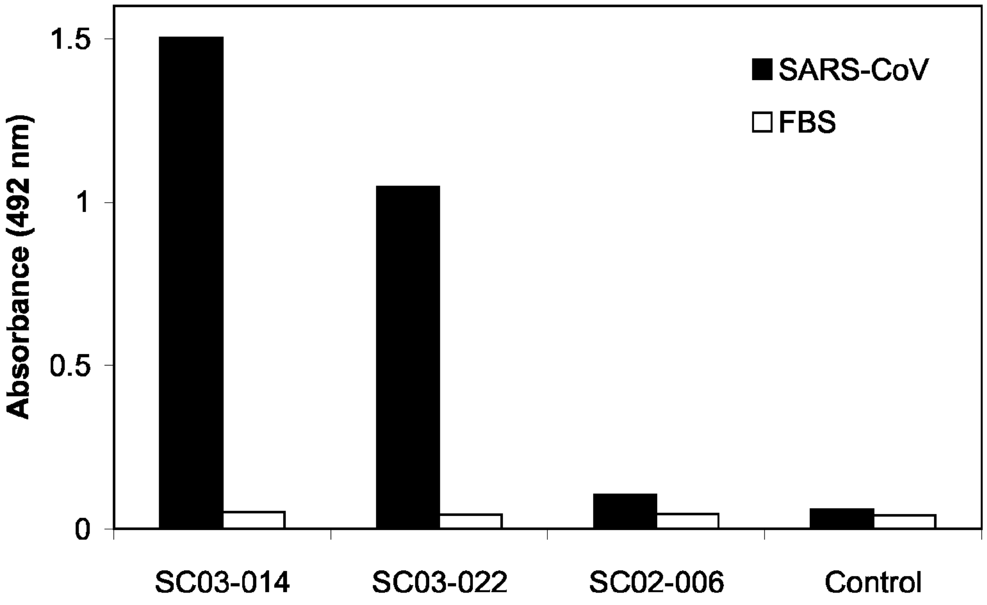
FIG. 1 shows results from an ELISA, wherein the binding of the single-chain phage antibodies called SC03-014 and SC03-022 to an immobilized UV-inactivated SARS-CoV preparation (left column) or immobilized FBS (right column) was measured. The binding of the control single-chain phage antibody called SC02-006 is also shown. On the y-axis, the absorbance at 492 nm is shown.

To illustrate the invention, the following examples are provided. The examples are not intended to limit the scope of the invention in any way.

Example 1

Construction of a scFv Phage Display Library Using Peripheral Blood Lymphocytes of a Patient Having been Exposed to SARS-CoV Lymphocytes were obtained from a patient recovered from SARS-CoV (see Rickerts et al. 2003) and frozen in liquid nitrogen. The lymphocytes were quickly thawed in a 37° C. water bath and transferred to wet ice. The lymphocytes were diluted with cold DMEM culture medium to a final volume of 50 ml in a 50 ml tube and centrifuged for five minutes at 350×g. The obtained cell pellet was suspended in 5 ml DMEM and cell density was determined microscopically using trypan-blue exclusion to visualize dead cells. All cells (~5×10$^6$) were spun again for five minutes at 350×g, decanted and suspended in residual fluid (DMEM). Total RNA was prepared from these cells using organic phase separation (TRIZOL™) and subsequent ethanol precipitation. The obtained RNA was dissolved in DEPC-treated ultrapure water and the concentration was determined by OD 260 nm measurement. Thereafter, the RNA was diluted to a concentration of 100 ng/μl. Next, 1 μg of RNA was converted into cDNA as follows: To 10 μl total RNA, 13 μl DEPC-treated ultrapure water and 1 μl random hexamers (500 ng/μl) were added and the obtained mixture was heated at 65° C. for five minutes and quickly cooled on wet ice. Then, 8 μl 5× First-Strand buffer, 2 μl dNTP (10 mM each), 2 μl DTT (0.1 M), 2 μl Rnase-inhibitor (40 U/μl) and 2 μl Superscript™ III MMLV reverse transcriptase (200 U/μl) were added to the mixture, incubated at room temperature for five minutes and incubated for one hour at 50° C. The reaction was terminated by heat inactivation, i.e., by incubating the mixture for 15 minutes at 75° C.

The obtained cDNA products were diluted to a final volume of 200 μl with DEPC-treated ultrapure water. The OD 260 nm of a 50 times diluted solution (in 10 mM Tris buffer) of the dilution of the obtained cDNA products gave a value of 0.1.

Five to 10 μl of the diluted cDNA products were used as template for PCR amplification of the immunoglobulin gamma heavy-chain family and kappa or lambda light-chain sequences using specific oligonucleotide primers (see Tables 2-9). PCR reaction mixtures contained, besides the diluted cDNA products, 25 pmol sense primer and 25 pmol anti-sense primer in a final volume of 50 μl of 20 mM Tris-HCl (pH 8.4), 50 mM KCl, 2.5 mM $MgCl_2$, 250 μM dNTPs and 1.25 units Taq polymerase. In a heated-lid thermal cycler having a temperature of 96° C., the mixtures obtained were quickly melted for two minutes, followed by 30 amplification cycles of: 30 seconds at 96° C., 30 seconds at 60° C. and 60 seconds at 72° C. In a first round amplification, each of nine sense-directed primers (see Table 2; covering all families of heavy-chain variable regions) was combined with an IgG-specific constant region anti-sense primer called HuCIgG 5'-GTC CAC CTT GGT GTT GCT GGG CTT-3' (SEQ ID NO:87) yielding nine products of about 650 basepairs. These products were purified on a 2% agarose gel and isolated from the gel using Qiagen gel-extraction columns. One-tenth of each of the isolated products was used in an identical PCR reaction as described above using the same nine sense primers (covering all families of heavy-chain variable regions), whereby each sense primer was combined with one of the four J-region-specific anti-sense primers (see Table 3). This resulted in 36 products of approximately 350 basepairs. The products obtained were purified on a 2% agarose gel and isolated from the gel using Qiagen gel-extraction columns. In a third round, 1/10 of each of the isolated products was subjected to re-amplification with the same set of primers as in the second round with the proviso that the primers used were extended with restriction sites (see Table 4) to enable directed cloning in the phage display vector pDV-C05 (see SEQ ID NO:88). This resulted again in 36 products. These products were pooled per used (VH) sense primer into nine fractions. In the next step, 2.5 μg of pooled fraction and 100 μg pDV-C05 vector were digested with NcoI and XhoI and purified by gel. Thereafter, a ligation was performed overnight at 16° C. as follows. To 500 ng pDV-C05 vector 70 ng pooled fraction was added in a total volume of 50 μl ligation mix containing 50 mM Tris-HCl (pH 7.5), 10 mM $MgCl_2$, 10 mM DTT, 1 mM ATP, 25 μg/ml BSA and 2.5 μl T4 DNA Ligase (400 u/μl). This procedure was followed for each pooled fraction. The ligation mixes were purified by phenol/chloroform, followed by a chloroform extraction and ethanol precipitation, methods well known to the skilled artisan. The DNA obtained was dissolved in 50 μl ultrapure water and per ligation mix two times 2.5 μl aliquots were electroporated into 40 μl of TG1-competent *E. coli* bacteria according to the manufacturer's protocol (Stratagene). Transformants were grown overnight at 37° C. in a total of 27 dishes (three dishes per pooled fraction; dimension of dish: 240 mm×240 mm) containing 2TY agar supplemented with 50 μg/ml ampicillin and 4.5% glucose. A (sub)library of variable heavy-chain regions was obtained by scraping the transformants from the agar plates. This (sub)library was directly used for plasmid DNA preparation using a Qiagen™ kit.

The light-chain immunoglobulin sequences were amplified from the same cDNA preparation in a similar three round PCR procedure and identical reaction parameters as described above for the heavy-chain regions with the proviso that the primers depicted in Tables 5-9 were used. The first amplification was performed using a set of seventeen light-chain variable region sense primers (eleven for the lambda light-chain (see Table 5) and six for the kappa light-chain (see Table 6)), each combined with an anti-sense primer recognizing the C-kappa called HuCκ 5'-ACACTCTCCCCTGTTGAAGCTCTT-3' (see SEQ ID NO:89) or C-lambda constant region HuCλ2 5'-TGAACATTCTGTAGGGGCCACTG-3' (see SEQ ID NO:90) or HuCλ7 5'-AGAGCATTCTGCAGGGGCCACTG-3' (see SEQ ID NO:91) (the HuCλ2 and HuCλ7 anti-sense primers were mixed to equimolarity before use), yielding 17 products of about 600 basepairs. These products were purified on a 2% agarose gel and isolated from the gel using Qiagen gel-extraction columns. One-tenth of each of the isolated products was used in an identical PCR reaction as described above using the same seventeen sense primers, whereby each lambda light-chain sense primer was combined with one of the three JX-region-specific anti-sense primers (see, Table 7) and each kappa light-change sense primer was combined with one of the five Jκ-region-specific anti-sense primers (see, Table 8). This resulted in 63 products of approximately 350 basepairs. The products obtained were purified on a 2% agarose gel and isolated from the gel using Qiagen gel-extraction columns. In a third round, 1/10 of each of the isolated products was subjected to re-amplification with the same set of primers as in the second round with the proviso that the primers used were extended with restriction sites (see Table 9) to enable directed cloning in the heavy-chain (sub)library vector. This resulted again in 63 products. These products were pooled to a total of ten fractions. This number of fractions was chosen to maintain the natural distribution of the different light-chain families within the library and to over- or under-represent certain families. The number of alleles within a family was used to determine the percentage of representation within a library (see Table 10). Next, the fractions were digested with SalI and NotI and ligated in the heavy-chain (sub)library vector, which was cut with the same restriction enzymes, using the same ligation procedure and volumes as described above for the heavy-chain (sub)library. Ligation purification and subsequent transformation of the resulting definitive library was also performed as described above for the heavy-chain (sub)library. The transformants were grown in 30 dishes (three dishes per pooled fraction; dimension of dish: 240 mm×240 mm) containing 2TY agar supplemented with 50 μg/ml ampicillin and 4.5% glucose. All bacteria were harvested in 2TY culture medium containing 50 μg/ml ampicillin and 4.5% glucose, mixed with glycerol to 15% (v/v) and frozen in 1.5 ml aliquots at −80° C.

Example 2

Selection of Phage Carrying Single-Chain Fv Fragments Specifically Recognizing SARS-CoV Antibody fragments were selected using antibody phage display libraries and technology, essentially as described in U.S. Pat. No. 6,265,150 and in WO 98/15833, both of which are incorporated herein in their entirety. All procedures were performed at room temperature unless stated otherwise. An inactivated SARS-CoV preparation (Frankfurt 1 strain) was prepared as follows. Medium from Vero cells that were infected with SARS-CoV strain Frankfurt 1 was harvested as soon as cyotopathic effect (CPE) was observed. Cell debris was removed by centrifugation of the harvested medium for 15 minutes at 3000 rpm. The obtained supernatant was collected, spun again for 15 minutes at 3000 rpm and transferred to a clean tube. Subsequently, ultracentrifuge tubes were filled with 10 ml sterile 25% glycerol in PBS. Twenty ml of the cleared supernatant was gently applied on the glycerol cushion and the tubes were spun for two hours at 20,000 rpm at 4° C. The supernatant was discarded and the virus pellets were resuspended in 1 ml TNE buffer (10 mM Tris-HCl pH 7.4, 1 mM EDTA, 200 mM NaCl) and stored at −80° C. Next, the resuspended virus pellets were gamma-irradiated at 45kGy on dry ice. Subsequently, they were tested for the absence of infectivity in cell culture. If absence of infectivity was established, the thus obtained inactivated SARS-CoV preparation was used for selection of single-chain phage antibodies specifically binding to SARS-CoV.

The inactivated virus preparation and heat-inactivated fetal bovine serum (FBS) were coated overnight at 4° C. onto the surface of separate Maxisorp™ plastic tubes (Nunc). The tubes were blocked for two hours in 3 ml PBS containing 2% FBS and 2% fat free milk powder (2% PBS-FM). After two hours, the FBS-coated tube was emptied and washed three times with PBS. To this tube, 500 μl (approximately $10^{13}$ cfu) of a phage display library expressing single-chain Fv fragments (scFvs) essentially prepared as described by De Kruif et al. (1995a) and references therein (which are incorporated herein in their entirety), 500 μl 4% PBS-FM and 2 ml 2% PBS-FM were added. The tube was sealed and rotated slowly at room temperature for two hours. Subsequently, the obtained blocked phage library (3 ml) was transferred to a SARS-CoV preparation-coated tube that had been washed three times with PBS. Tween-20 was added to a final concentration of 0.05% and binding was allowed to proceed for two hours on a slowly rotating wheel at room temperature or at 37° C. The tube was emptied and washed ten times with PBS containing 0.05% Tween-20, followed by washing ten times with PBS. One ml glycine-HCL (0.05 M, pH 2.2) was added to elute bound phages, and the tube was rotated slowly for ten minutes. For neutralization purposes, the eluted phages were added to 500 μl 1 M Tris-HCl pH 7.4. To this mixture, 5 ml of exponentially growing XL-1 blue bacterial culture was added. The obtained culture was incubated for thirty minutes at 37° C. without shaking. Then, the bacteria were plated on TYE agar plates containing ampicillin, tetracycline and glucose. After overnight incubation of the plates at 37° C., the colonies were scraped from the plates and used to prepare an enriched phage library, essentially as described by De Kruif et al. (1995a) and WO 02/103012 (both are incorporated by reference herein). Briefly, scraped bacteria were used to inoculate 2TY medium containing ampicillin, tetracycline and glucose and grown at a temperature of 37° C. to an OD 600 nm of ~0.3. CT or VCSM13 helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the obtained supernatant were precipitated using polyethylene glycol 6000/NaCl. Finally, the phages were dissolved in a small volume of PBS containing 1% BSA, filter-sterilized and used for a next round of selection. The selection/re-infection procedure was performed two or three times. After each round of selection, individual *E. coli* colonies were used to prepare monoclonal phage antibodies. Essentially, individual colonies were grown to log-phase and infected with VCSM13 helper phages, after which phage antibody production was allowed to proceed overnight. Phage antibody containing supernatants were tested in ELISA for binding activity to the SARS-CoV preparation, which was coated to 96-well plates. In the above-described selection, the phage antibody called SC03-014 was obtained. ScFvs of the phage antibody SC03-014 were produced as described before in De Kruif et al., (1995a and 1995b) and references therein (which are incorporated herein in their entirety). The buffer of the scFvs was adjusted to 1×PBS.

Additionally, antibody fragments were selected from the immune phage display library expressing single-chain Fv fragments (scFvs) (see Example 1 for the construction of this library) essentially as described supra. For the selection described below, a UV-inactivated SARS-CoV preparation was used. UV-inactivated SARS-CoV (Frankfurt 1 strain) was prepared as follows. Medium from Vero cells that were infected with O.I. moi (multiplicity of infection) SARS-CoV strain Frankfurt 1 was harvested as soon as cyotopathic effect (CPE) was observed. Cells were once frozen at −20° C. and thawed. Cell debris was removed by centrifugation of the harvested medium for 15 minutes at 3000 rpm. The obtained supernatant was collected, spun again for 15 minutes at 3000 rpm and transferred to a clean tube. Subsequently, ultracentrifuge tubes were filled with 10 ml sterile 25% v/v glycerol in PBS. 20 ml of the cleared supernatant was gently applied on the glycerol cushion and the tubes were spun for two hours at 20,000 rpm at 4° C. in a Beckman SW28 rotor. The supernatant was discarded and the virus pellets were resuspended in 1 ml TNE buffer (10 mM Tris-HCl pH 7.4, 1 mM EDTA, 200 mM NaCl) and stored at −80° C. Next, the resuspended virus pellets were UV-irradiated at 4° C. for 15 minutes (UV-B radiation 280-350 nm; λmax 306 nm). Subsequently, they were tested for the absence of infectivity in cell culture. If absence of infectivity was established, the thus obtained inactivated SARS-CoV preparations were used for further experiments.

In contrast to the selections described supra, no pre-subtraction using heat-inactivated fetal bovine serum-coated Maxisorp™ tubes (Nunc) was performed. To the SARS-CoV-coated tubes, 500 μl (approximately $10^{13}$ cfu) of the immune phage display library expressing single-chain Fv fragments (scFvs), one volume of 4% PBS-FM and Tween-20 to a final concentration of 0.05% was added.

For the immune phage display library selections that consisted of a single selection round only, binding was allowed to proceed at 37° C. or room temperature on a slowly rotating wheel at 37° C. followed by an incubation of 30 minutes without agitation. The following selections and washes were performed: incubation at 37° C., washing five times with PBS containing 0.05% Tween-20 (PBST) and five times with PBS; incubation at 37° C., washing ten times with PBST and ten times with PBS; incubation at room temperature, washing ten times with PBST and ten times with PBS. Bound phages were eluted and processed as described above. Phages derived from individual colonies were tested in ELISA for binding activity to SARS-CoV coated to 96-well plates. In the selections from the immune phage display library, the phage antibody called SC03-022 was obtained.

Example 3

Validation of the SARS-CoV-Specific Single-Chain Phage Antibodies

Selected single-chain phage antibodies that were obtained in the screens described above, were validated in ELISA for specificity, i.e., binding to the UV-inactivated SARS-CoV preparation prepared as described supra. Additionally, the single-chain phage antibodies were also tested for binding to 10% FBS. For this purpose, the UV-inactivated SARS-CoV preparation or 10% FBS preparation was coated to Maxisorp™ ELISA plates. After coating, the plates were blocked in 2% PBS-FM. The selected single-chain phage antibodies were incubated in an equal volume of 4% PBS-FM to obtain blocked phage antibodies. The plates were emptied, washed three times with PBS, after which the blocked phage antibodies were added. Incubation was allowed to proceed for one hour, the plates were washed in PBS containing 0.05% Tween-20 and bound phage antibodies were detected (using OD 492 nm measurement) using an anti-M13 antibody conjugated to peroxidase. As a control, the procedure was performed simultaneously using no single-chain phage antibody or control single-chain phage antibody directed against thyroglobulin (SC02-006) (see De Kruif et al. 1995a and 1995b). Both controls served as a negative control. As shown in FIG. 1, the selected phage antibodies called SC03-014 and SC03-022 displayed significant binding to the immobilized UV-inactivated SARS-CoV preparation, while no binding to FBS was observed.

Example 4

Characterization of the scFvs Specific for SARS-CoV

From the selected specific single-chain phage antibody (scFv) clones, plasmid DNA was obtained and nucleotide sequences were determined according to standard techniques. The nucleotide sequences of the scFvs (including restriction sites for cloning) called SC03-014 and SC03-022 are shown in SEQ ID NO:92 and SEQ ID NO:94, respectively. The amino acid sequences of the scFvs called SC03-014 and SC03-022 are shown in SEQ ID NO:93 and SEQ ID NO:95, respectively. The VH and VL gene identity (see I. M. Tomlinson, S. C. Williams, O. Ignatovitch, S. J. Corbett, G. Winter, V-BASE Sequence Directory, Cambridge United Kingdom: MRC Centre for Protein Engineering (1997)) and heavy-chain CDR3 compositions of the scFvs specifically binding the SARS-CoV preparation are depicted in Table 11.

Example 5

Construction of Fully Human Immunoglobulin Molecules (Human Monoclonal Anti-SARS-CoV Antibodies) from the Selected Anti-SARS-CoV Single-Chain Fvs Heavy- and light-chain variable regions of the scFvs called SC03-014 and SC03-022 were PCR-amplified using oligonucleotides to append restriction sites and/or sequences for expression in the IgG expression vectors pSyn-C03-HCγ1 (see SEQ ID NO:96) and pSyn-C05-Cκ (see SEQ ID NO:97), respectively. The $V_L$ gene of scFv SC03-014 was amplified using oligonucleotides 5K-I acctgtctcgagttttccatggctgacatccagatgacccagtctccatcctcc (SEQ ID NO:98) and sy3K-C gctgggggcggccacggtccgtttgatctccaccttggtccc (SEQ ID NO:99) and the PCR product cloned into vector pSyn-C05-Cκ. The $V_L$ gene of scFv SC03-022 was amplified using oligonucleotides 5K-J acctgtctcgagttttccatggctgacatcgtgatgacccagtctccag (SEQ ID NO:100) and sy3K-F gctgggggcggccacggtccgcttgatctccaccttggtccc (SEQ ID NO:101) and the PCR product cloned into vector pSyn-C05-Cκ. Nucleotide sequences for all constructs were verified according to standard techniques known to the skilled artisan. $V_H$ genes of scFv SC03-014 were amplified using oligonucleotides 5H-B acctgtcttgaattctccatggccgaggtgcagctggtggagtctg (SEQ ID NO:102) and sy3H-A gcccttggtgctagcgctggagacggtcaccagggtgccctggcccc (SEQ ID NO:103). $V_H$ genes of scFv SC03-022 were amplified using oligonucleotide set 5H-H acctgtcttgaattctccatggccgaggtgcagctggtgcagtctgg (SEQ ID NO:104) and sy3H-C gcccttggtgctagcgctggagacggtcacggtggtgccctggcccc (SEQ ID NO:105). Thereafter, the PCR products were cloned into vector pSyn-C03-HCγ1 and nucleotide sequences were verified according to standard techniques known to the skilled person in the art.

The resulting expression constructs pgG103-014C03 and pgG103-022C03 encoding the anti-SARS-CoV human IgG1 heavy chains were transiently expressed in combination with the pSyn-C05-VkI ($V_L$ SC03-014) and pgG103-022C05 ($V_L$ SC03-022), respectively, in HEK293T or PER.C6® cells and supernatants containing IgG1 antibodies were obtained. The nucleotide sequences of the heavy chains of the antibodies called CR03-014 and CR03-022 are shown in SEQ ID NO:106 and SEQ ID NO:108, respectively. The amino acid sequences of the heavy chains of the antibodies CR03-014 and CR03-022 are shown in SEQ ID NO:107 and SEQ ID NO:109, respectively.

The nucleotide sequences of the light chain of antibodies CR03-014 and CR03-022 is shown in SEQ ID NO:110 and SEQ ID NO:112, respectively. The amino acid sequences of the light chain of antibodies CR03-014 and CR03-022 is shown in SEQ ID NO:111 and SEQ ID NO:113. Subsequently, the recombinant human monoclonal antibodies were purified over protein-A columns and size-exclusion columns using standard purification methods used generally for immunoglobulins (see, for instance, WO 00/63403, which is incorporated by reference herein).

Example 6

Screening Assay for SARS-CoV-Neutralizing Activity of Recombinant Human Anti-SARS-CoV Antibodies The SARS-CoV neutralization assay was performed on Vero cells (ATCC CCL 81). The SARS-CoV strains used in the neutralization assay were the Frankfurt 1 strain (for the complete genome of this strain, see EMBL-database accession # AY291315) (Rickerts et al. 2003). Virus stocks of the strains were used in a titer of $4\times10^3$ $TCID_{50}$/ml (50% tissue culture infective dose per ml), with the titer calculated according to the method of Spearman and Kaerber, which is known to the average skilled person. Recombinant human anti-SARS-CoV antibodies produced as described above were screened by serially two-fold dilution of the undiluted material (2.5 mg/ml) in PBS starting from 1:4 (dilution range 1:4-1:512). A neutralization titer of ≧1:4 was regarded as specific evidence of reactivity of the antibodies against SARS-CoV in the screening assay. Convalescent serum from a SARS patient was used as a positive control for the neutralization assay.

In general, the neutralization assay worked as follows. Twenty-five μl of the respective antibody dilutions were mixed with 25 μl of virus suspension (=approx. 100 $TCID_{50}$/25 μl) and incubated for one hour at 37° C. The suspension was then pipetted in triplicate into 96-well plates. Next, 50 μl of a freshly trypsinized and homogenized suspension of Vero cells (1:3 split of the confluent cell monolayer of a T75-flask), resuspended in DMEM containing 10% w/v FCS and antibiotics, were added. The inoculated cells were cultured for three to four days at 37° C. and observed daily for the development of cytopathic effect (CPE). CPE was compared to the positive control (virus-inoculated cells) and negative controls (mock-inoculated cells). The complete absence of CPE in an individual cell culture was defined as protection (=100% titer reduction). The highest antibody/serum dilution giving protection in 66% percent of wells was defined as the neutralizing antibody titer. The experiment was performed three times in triplicate (see Tables 12A, 12B and 12C). The IgGs CR03-014, CR03-022, a negative control IgG1 and a positive control serum from a SARS patient were tested for SARS-CoV-neutralizing activity. It is clear from Tables 12A, 12B and 12C that the IgGs CR03-014 and CR03-022 displayed significant neutralizing activity. The CR03-014 IgG neutralized the Frankfurt 1 strain at titers of 128 (n=1) or 256 (n=2) in the above-described assay. The CR03-022 IgG neutralized the Frankfurt 1 strain at titers of 32 (n=1) or 64 (n=2). These titers correspond to final antibody neutralization concentrations in the tissue culture well of 2.4 μg/ml (n=2) and 4.9 μg/ml (n=1) for CR03-014 and 9.8 μg/ml (n=2) and 19.5 μg/ml (n=1) for CR03-022. In light of these concentrations, both neutralizing antibodies may be suitable in the prophylaxis and/or treatment of a condition resulting from a SARS-CoV infection.

Additionally, different SARS-CoV strains were used to evaluate the potency and breadth of protection of the anti-SARS-CoV antibodies. The SARS-CoV strains HKU-36, HKU-39849, HKU-66, HKU-61567, GZ43 and GZ50 were passaged on FRhK-4 cells two or three times before testing (see Table 13). Strain HKU-61644 was passaged on Vero cells and tested after passages 1 and 15. The SARS-CoV neutralization assay was performed on FRhK-4 cells as follows. A 500 μl stock solution (100 μg/ml) of antibody was prepared in maintenance medium (MM, MEM supplemented with 1% w/v FCS). From this stock solution, two-fold serial dilutions were prepared. Two hundred twenty μl stock solution (100 μg/ml) was added in duplo in a 96-well plate, from which 110 μl was taken and mixed with 110 μl MM in each of the nine subsequent wells. One hundred ten μl of the tenth well was discarded. This resulted in ten wells containing 110 μl 0.2-100 μg/ml antibody. One hundred ten μl of the antibody dilution was mixed with 110 μA of the different SARS-CoV isolates at a concentration of 2000 $TCID_{50}$/ml, with the titer calculated according to the method of Reed and Muench, which is known to the skilled artisan. At this stage, in a 220 μl volume, antibody concentrations varied from 0.1 to 50 μg/ml in the presence of 1000 $TCID_{50}$/ml SARS-CoV. The 96-well plate containing the antibody/virus mixtures was preincubated for one to two hours at 37° C. One hundred μl of the antibody/virus mixtures were added in quadruplicate to wells from a second 96-well tissue culture plate containing confluent FRhK-4 cells in 100 μl MM and incubated at 37° C. During this final incubation step, 100 $TCID_{50}$ of SARS-CoV was present in the presence of antibody concentrations varying from 0.05 to 25 μg/ml. The cells were cultured at 37° C. and observed for the development of CPE at 72 and 96 hours. CPE was compared to a positive control (SARS-CoV-inoculated cells) and a negative control (cells incubated with MM only). The antibody neutralization titer was determined as the concentration of antibody that gave 100% protection of the quadruplicate cell cultures. The monoclonal anti-SARS-CoV antibody CR03-014 completely neutralized 100 $TCID_{50}$ of all tested SARS-CoV isolates at a concentration of 12.5 μg/ml (see Table 13). This indicates that antibody CR03-014 is able to neutralize a variety of SARS-CoV isolates.

In an additional experiment, the SARS-CoV neutralization assay was performed as described for the Frankfurt 1 strain, supra, to determine synergy between SARS-CoV-neutralizing antibodies CR03-014 and CR03-022. Stock solutions of antibody CR03-014 and CR03-022 of approximately similar potency were mixed in different ratios. To compensate for an estimated four times higher potency of CR03-014 compared to CR03-022, the CR03-014 antibody stock solution of 2.5 mg/ml was diluted four-fold to 625 μg/ml. Subsequently, antibody CR03-014 and CR03-022 were mixed in the following ratios (mixture A: CR03-014 0%, CR03-022 100%; mixture B: CR03-014 10%, CR03-022 90%; mixture C: CR03-014 50%, CR03-022 50%; mixture D: CR03-014 90%, CR03-022 10%; and mixture E: CR03-014 100%, CR03-022 0%). When the antibodies in the mixtures have an additive effect, the mixtures should neutralize SARS-CoV at the same titer as the individual antibodies present in the mixtures. When the antibodies in the mixtures have a synergistic effect, the mixtures should neutralize SARS-CoV at a higher titer as the individual antibodies present in the mixtures. The neutralization assay was performed twice in triplicate wells as described above. The results of both assays were combined. Protection of at least 66% percent of the wells (four of the six wells tested) was defined as the neutralizing antibody titer. The neutralization titers of the separate mixtures are shown in Table 14. From Table 14 can be deducted that the mixtures had the following titers: mixture A, 64; mixture B, 256; mixture C, >1024; mixture D, 256; and mixture E, 16. From this can be concluded that, when both antibodies were tested in combination (mixtures B-D), the neutralizing titers were higher than those for antibody CR03-014 and CR03-022 individually. Together, these data indicate that antibodies CR03-014 and CR03-022 exhibit synergistic SARS-CoV-neutralizing activity.

In yet another embodiment, the SARS-CoV neutralization assay showing synergy between the anti-SARS-CoV antibodies was performed on FRhK-4 cells (ATCC CRL-1688) as follows. The SARS-CoV strain called HK-39849 (GenBank accession number AY278491) was used in a titer of $2\times10^3$ $TCID_{50}$/ml as calculated according to the method of Reed and Muench known to the average skilled person. The human anti-SARS-CoV antibodies were screened by serial 1.46-fold dilution in maintenance medium (MM) (1% w/v FCS in MEM with antibiotic) starting at a concentration of 200 μg/ml (dilution range 200-6.7 μg/ml) in duplo. Four different compositions were tested: antibody CR03-014 individually, antibody CR03-022 individually, control IgG1 antibody, and antibodies CR03-014 and CR03-022 in combination (start concentration 200 μg/ml of each antibody). One hundred ten μl of virus suspension was mixed with 110 μl of the respective recombinant human anti-SARS-CoV antibody dilution and incubated for one hour at 37° C. One hundred μl of this suspension was then pipetted two times in duplicate into 96-well plates containing an 80% confluent monolayer of FRhK-4 cells in 100 μl MM. The FRhK-4 cells were cultured at 37° C. and observed after three to four days for the development of CPE. CPE was compared to the positive control (virus-inoculated cells) and negative controls (mock-inoculated cells or cells incubated with recombinant antibody only). The complete absence of CPE in an individual cell culture was defined as protection (=100% titer reduction). The concept of the combination index (CI) was used to quantitate synergistic effects as described previously (Chou and Talalay, 1984). According to the concept, a combination of agents that produce an additive effect the sum of the ratios of their concentrations in the mixture (cmixt) to the concentrations of agents that individually have the same effect as the mixture (ceffect) is 1. This sum is the CI. When this sum is lower than 1, the agents act in synergy. For a two-component system, as in the present study, CI is calculated as follows:

$$\frac{C1mixt}{C1eff}+\frac{C2mixt}{C2eff}=1$$

C1mixt is the concentration of the first component in the mixture that leads to a certain level of inhibition (f), c1effect is that concentration of the first component that alone (in the absence of the second component) will result in the same inhibitory effect as the mixture of the two components, and c2mixt and c2effect are the corresponding concentrations for the second component.

To determine the CI for antibodies CR03-014 and CR03-022, the neutralization assay was performed as described above. Complete neutralization of 100 $TCID_{50}$ of strain HKU39849 was reached at 7.6 μg/ml for CR03-014, 50.0 μg/ml for CR03-022 and 2.4 μg/ml of each antibody when added in combination. This outcome results in a CI of 2.4/7.6+2.4/50.0=0.36. Fifty percent neutralization was achieved at 5.9 μg/ml for CR03-014, 30.2 μg/ml for CR03-022 and 1.7 μg/ml of each antibody when added in combination. This results in a CI of 1.7/5.9+1.7/30.2=0.34. Thus, at both 50% and 100% neutralization, CI values lower than 1 were obtained for a mixture of CR03-014 and CR03-022, which indicates that both antibodies act in synergy against SARS-CoV.

Example 7

Figure 2:
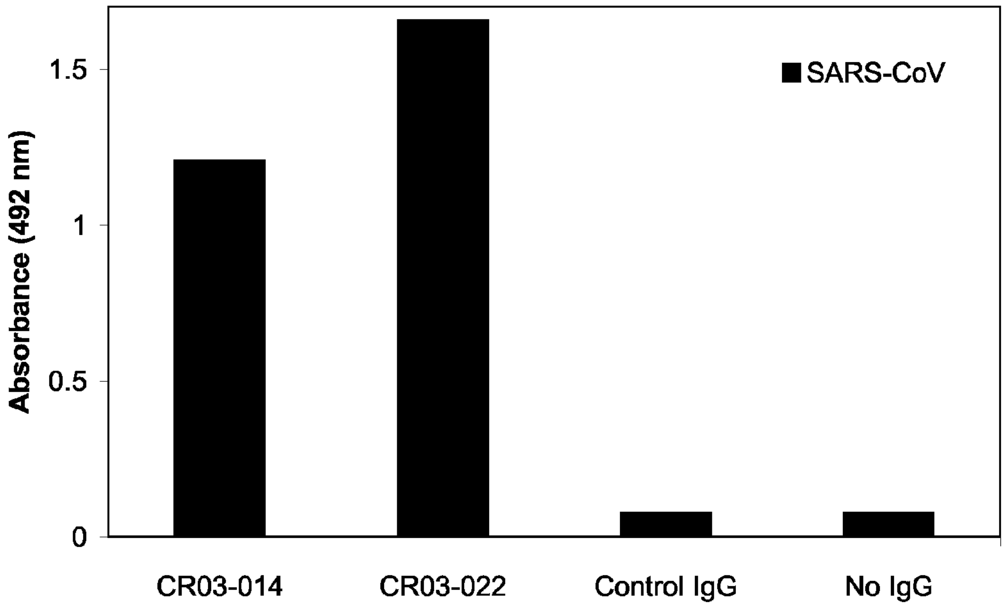
FIG. 2 shows an ELISA binding of IgGs CR03-014, CR03-022, control IgG and no IgG to an inactivated SARS-CoV preparation. On the Y-axis, the absorbance at 492 nm is shown.

Binding of Anti-SARS Antibodies to SARS-CoV, SARS-CoV Spike Protein and Fragments Thereof An ELISA to detect binding of anti-SARS antibodies to SARS-CoV was performed as follows. Wells of ELISA plates were coated overnight with UV-inactivated SARS-CoV preparation in 50 mM bicarbonate buffer pH 9.6. The wells of the plates were washed three times with PBS containing 0.05% Tween and blocked for two hours at 37° C. with PBS containing 1% BSA. Next, the antibodies diluted in PBS containing 1% BSA were incubated for one hour at room temperature. The wells were washed three times with PBS containing 0.05% Tween and incubated for one hour at room temperature using a murine anti-Hu-IgG HRP conjugate. Development was done with O-phenylenediamine substrate, the reaction was stopped by the addition of 1 M $H_2SO_4$ and the absorbance was measured at 492 nm. As shown in FIG. 2, antibodies CR03-014 and CR03-022 were both capable of binding an inactivated SARS-CoV preparation in ELISA in contrast to a negative control IgG that was directed against an irrelevant antigen.

Figure 3:
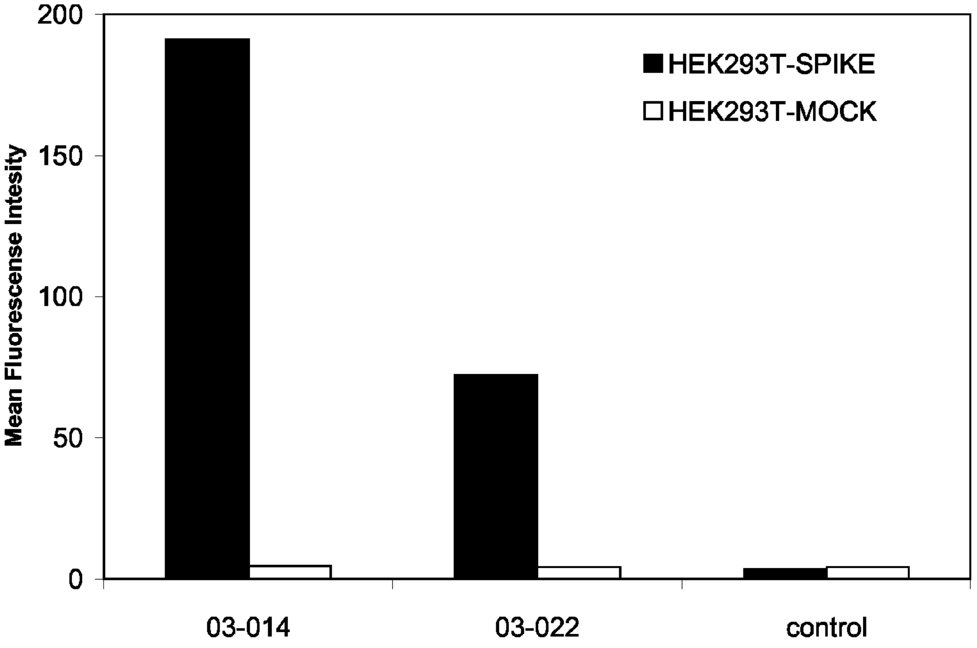
FIG. 3 shows a FACS binding of the scFv phage antibodies SC03-014, SC03-022 and a control scFv phage antibody to the full-length S protein expressed on HEK293T cells (left column) or mock-transfected HEK293T cells (right column). On the Y-axis, the mean fluorescence intensity is shown.

To detect the target of the antibodies CR03-014 and CR03-022, another binding assay was used. Single-chain phage antibodies SC03-014 and SC03-022 were analyzed for their ability to bind HEK293T cells that recombinantly express proteins of SARS-CoV. To this end, HEK293T cells were transfected with a plasmid carrying a cDNA sequence encoding the spike (S) protein from SARS-CoV strain Frankfurt 1 or with control vector. For flow cytometry analysis, single-chain phage antibodies were first blocked in an equal volume of 4% PBS-M for 15 minutes at 4° C. prior to the staining of the transfected HEK293T cells. The blocked phage antibodies were added to mock transfected HEK293T cells and HEK293T cells transfected with the SARS-CoV S protein. The binding of the single-chain phage antibodies to the cells was visualized using a biotinylated anti-M13 antibody (Santa Cruz Biotechnology) followed by streptavidin-phycoerythrin (Caltag). As shown in FIG. 3, the single-chain phage antibodies SC03-014 and SC03-022 were capable of binding spike-transfected HEK293T cells, whereas no binding to mock-transfected HEK293T cells was observed. A control single-chain phage antibody did neither recognize the spike-transfected HEK293T cells nor the mock-transfected HEK293T cells. These data suggest that both antibodies are directed against the S protein of SARS-CoV.

Figure 4:
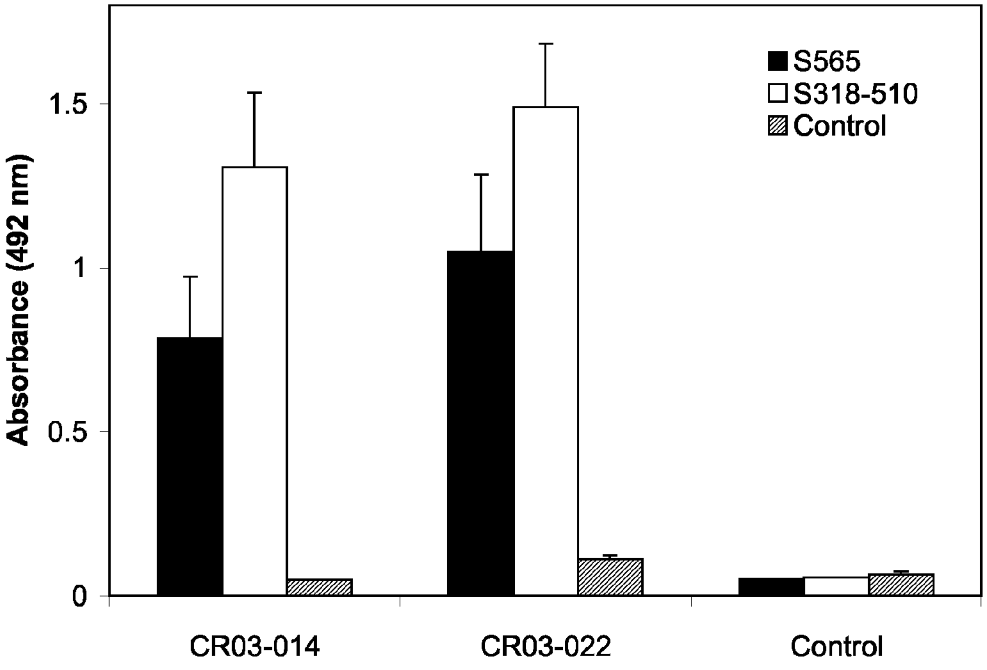
FIG. 4 shows an ELISA binding of the antibodies CR03-014, CR03-022 and a control antibody to the S565 fragment (amino acids 1-565 of the S protein of SARS-CoV; left column), S318-510 fragment (amino acids 318-510 of the S protein of SARS-CoV; middle column) and an irrelevant control myc-tagged antigen (right column). On the Y-axis, the absorbance at 492 nm is shown.

To further localize the binding sites of the antibodies within the S protein, an assay was performed wherein the antibodies were analyzed for their ability to bind to portions of the S protein of SARS-CoV. The nucleotide and amino acid sequence of the S protein is shown in SEQ ID NO:114 and SEQ ID NO:115, respectively. DNA coding for the N-terminal 565 amino acids (portion called S565) was cloned as a KpnI-BamHI fragment in pAdapt (Havenga et al., 2001) that was modified by insertion of the polylinker of the vector called pcDNA3.1/myc-His C (Invitrogen) (vector called pAdapt/myc-His C). A fragment corresponding to amino acid residues 318-510 of the S protein (portion called S318-510) was amplified on S gene cDNA using the oligonucleotide primers: EcoRIspikeFor318 5'-cctggaattctccatggccaacatcaccaacc-3' (SEQ ID NO:116) and XbaIspikeRev510 5'-gaagggccctctagacacggtggcagg-3' (SEQ ID NO:117). The resulting fragment was digested with EcoRI-XbaI and cloned into pHAVT20/myc His A to yield pHAVT20/myc-His A S318-510. In this vector, expression of fragment S318-510 fused to the HAVT20 leader sequence was under control of the human, full-length, immediate-early CMV promoter. DNA transfections were performed in HEK293T cells for transient expression using standard techniques. The S protein-derived fragments were used directly from culture supernatant or were purified from culture supernatant using Ni-NTA (Qiagen). An ELISA to evaluate binding of antibodies to the S protein-derived fragments was performed as follows. Wells of ELISA plates were coated overnight with 5 μg/ml anti-myc antibody in 50 mM bicarbonate buffer pH 9.6. The wells of the plates were washed three times with PBS containing 0.05% Tween and blocked for two hours at 37° C. with PBS containing 1% BSA. The wells coated with anti-myc antibody were incubated with the myc-tagged fragments S565 or S318-510 diluted in PBS containing 1% BSA for one hour at room temperature. The wells were washed three times with PBS containing 0.05% Tween. Next, the antibodies CR03-014, CR03-022 or control antibody diluted in PBS containing 1% BSA were incubated for one hour at room temperature. Detection of bound antibody was performed as described supra. As shown in FIG. 4, antibodies CR03-014 and CR03-022 were both capable of binding to the S565 and S318-510 fragment, but not to an irrelevant control myc-tagged antigen. A control antibody did not bind any of the fragments.

Figure 5:
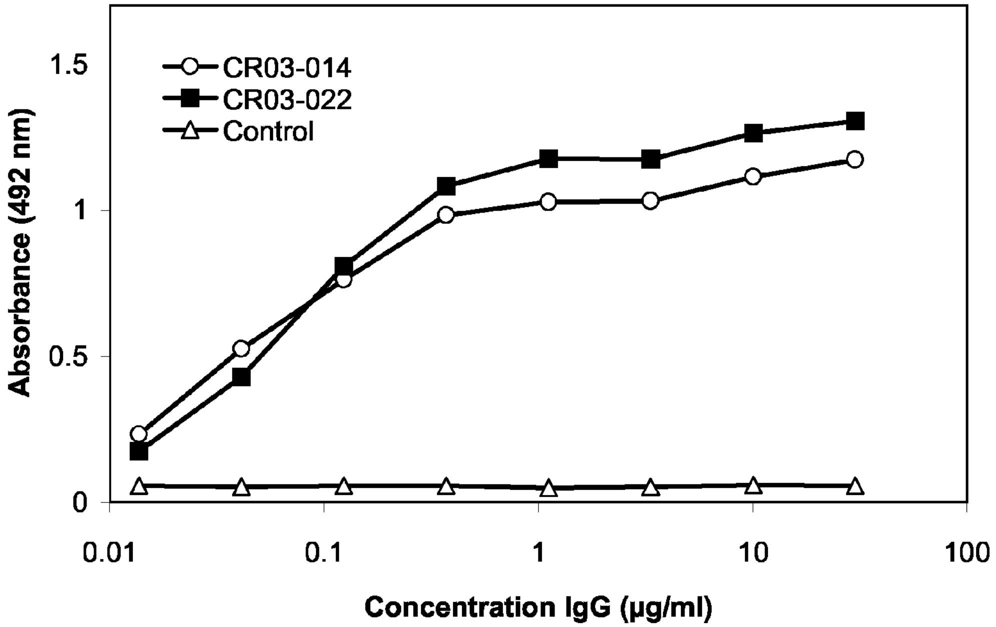
FIG. 5 shows an ELISA binding of dilutions of antibodies CR03-014, CR03-022 and a control antibody to the S565 fragment of the S protein of SARS-CoV. On the Y-axis, the absorbance at 492 nm is shown and on the X-axis, the amount of antibody in μg/ml is shown.

In order to rank the affinities of the antibodies for binding to the S565 fragment, a titration of IgG concentration was performed (by diluting the antibodies in PBS containing 1% ELK), followed by an ELISA as described above. Titration of the monoclonal antibodies showed that CR03-014 and CR03-022 bound S565 with approximately similar affinities (see FIG. 5). To investigate changes of affinities as a possible mechanism of synergy, the $K_D$ for CR03-014 and CR03-022 binding sequentially or simultaneously to recombinant receptor binding domain fragment S318-510 was investigated by means of BIAcore analysis. Surface plasmon resonance analyses were performed at 25° C. on a BIAcore3000™. CM5 sensorchips and running buffer HBS-EP were from Biacore AB (Uppsala Sweden). Recombinant S318-510 fragment was immobilized to CM5 chips using an amine coupling procedure resulting in a response level of approximately 1,000 resonance units (RU). Kinetic analysis was performed to determine the association rate ($k_a$), dissociation rate ($k_d$) constants and the affinity ($K_D$) of the monoclonal antibodies. Therefore, a concentration series of 0.4 to 250 nM IgG was prepared using two-fold dilutions in HBS-EP. Samples were injected in duplicate at a flow rate of 30 μl/minute (injection time=two minutes; dissociation time=five minutes). The sensor chip surface was regenerated with a pulse of 5 μl 5 nM NaOH. Biacore evaluation software (BIAevalution, July 2001) was used to fit the association and dissociation curves of all concentrations injected. The individual $K_D$ for CR03-014 and CR03-022 was determined as 16.3 nM and 0.125 nM, respectively, the $K_D$ for the antibodies binding simultaneously as 5.71 nM and for binding of CR03-014 to CR03-022 saturated S318-510 as 14.8 nM. Compared to the dose reduction indices of 3 and 20 for CR03-014 and CR03-022, respectively, neither simultaneous nor sequential binding of the monoclonal antibodies resulted in changes of which could explain their synergistic neutralizing action through cooperative binding.

Figure 6A:
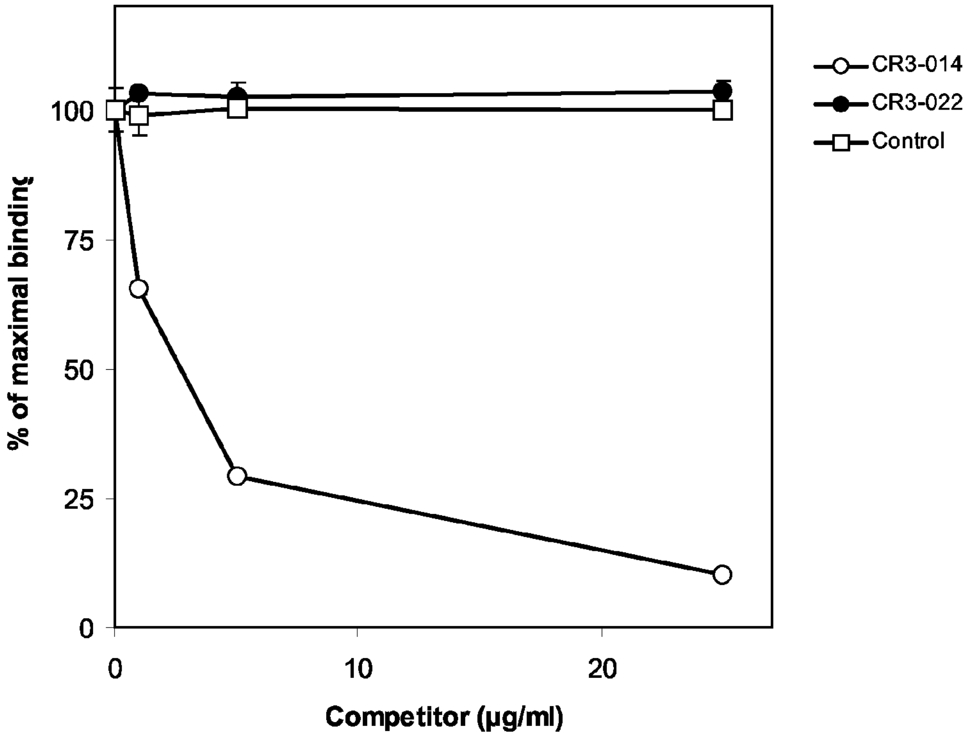
FIG. 6A shows competition between biotinylated antibody CR03-014 without competing antibody or with 1, 5 or 25 μg/ml competing antibody CR03-014, CR03-022 or control antibody.
Figure 6B:
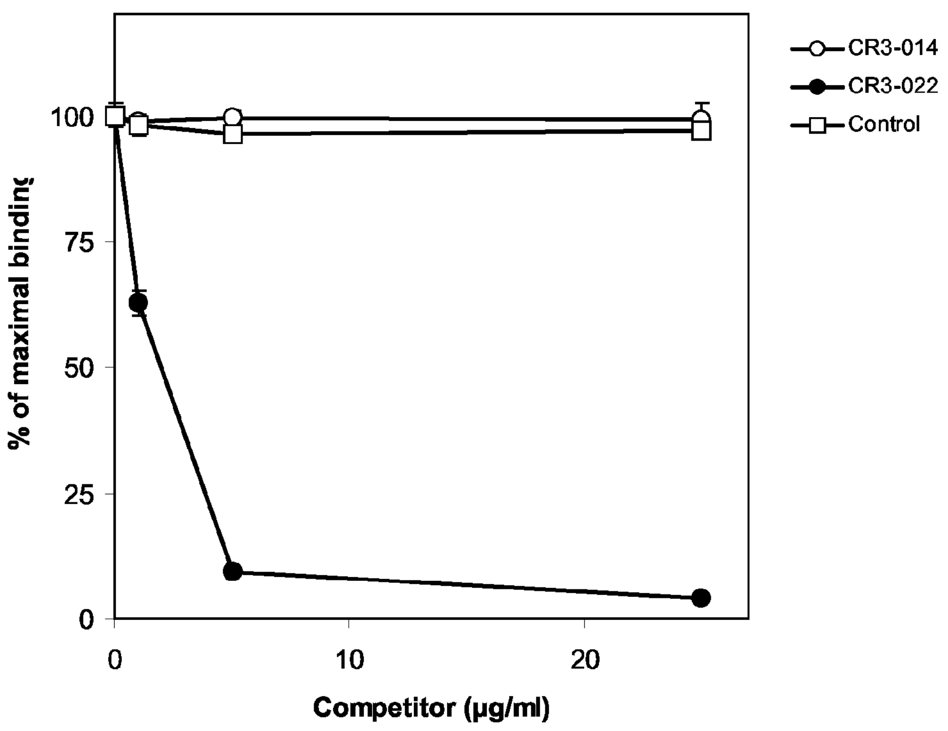
FIG. 6B shows competition between biotinylated antibody CR03-022 with or without the competing antibodies as described above. On the Y-axis, the percentage of maximal binding is shown and on the X-axis, the amount of the competing antibody in μg/ml is shown.

To further explore the antibody binding sites within the S protein, a competition ELISA on immobilized S318-510 fragment was performed. Captured S318-510 was incubated with non-saturating amounts of biotinylated antibody without competing antibody or in the presence of 1, 5, and 25 μg/ml of competing antibody (antibody CR03-014, CR03-022 or control antibody). Bound biotinylated antibody was detected with streptavidin-conjugated-HRP (BD Pharmingen) and developed as described above. FIG. 6A shows that binding of monoclonal antibody CR03-014 was unaffected in the presence of excess unlabeled monoclonal antibody control or antibody CR03-022. FIG. 6B shows that binding of antibody CR03-022 was unaffected in the presence of excess unlabeled monoclonal antibody control or antibody CR03-014. As expected, binding of both biotinylated CR03-014 and CR03-022 was effectively reduced by their unlabeled counterparts (see FIGS. 6A and 6B). These results demonstrate that the antibodies CR03-014 and CR03-022 do not compete with each other for binding to the S318-510 fragment and recognize different/distinct, non-competing epitopes.

Figure 7:
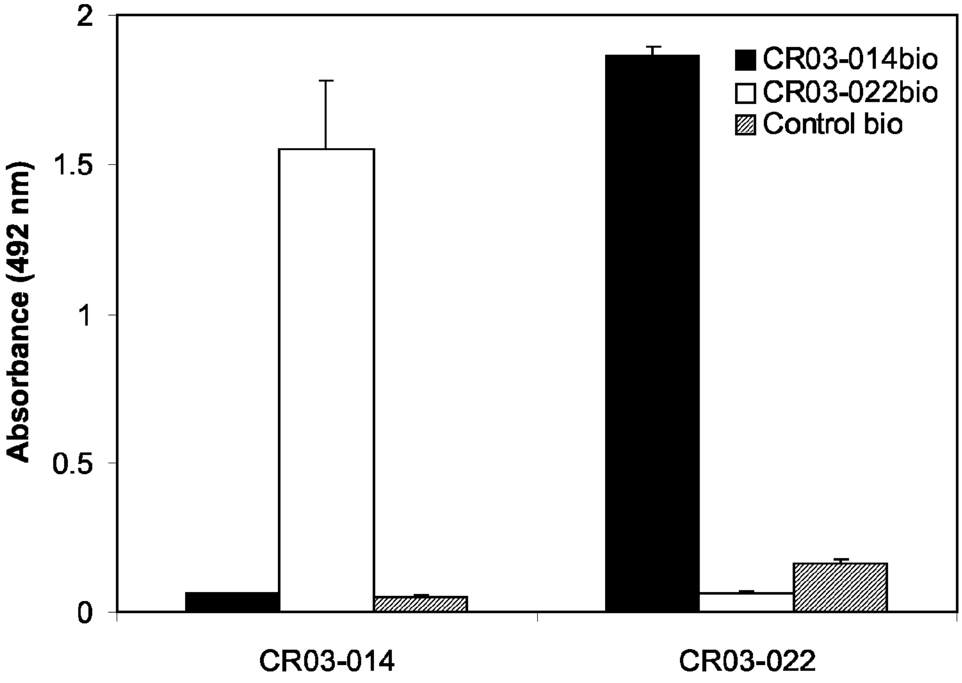
FIG. 7 shows a sandwich ELISA using anti-S protein antibodies. Immobilized antibodies CR03-014 and CR03-022 were used to capture S protein fragment S318-510. Bound fragment was detected using biotinylated antibody CR03-014, CR03-022 or control antibody. On the Y-axis, the absorbance at 492 nm is shown.

To confirm these findings, an antibody sandwich ELISA was performed. Antibodies CR03-014 and CR03-022 were coated overnight to microtiter wells at 5 μg/ml in 50 mM bicarbonate buffer pH 9.6. Capture of the S318-510 fragment, binding of biotinylated antibodies and subsequent development of the ELISA reaction was performed as described supra. FIG. 7 indicates that CR03-014-captured S318-510 could be bound by biotinylated CR03-022, but not by CR03-014. CR03-022-captured S318-510 could only be bound by biotinylated CR03-014 and not CR03-022. This indicates that CR03-014 and CR03-022 are able to bind simultaneously to different epitopes within the S-derived fragment S318-510 and furthermore indicates that both antibodies bind to different non-competing epitopes.

Example 8

Figure 8:
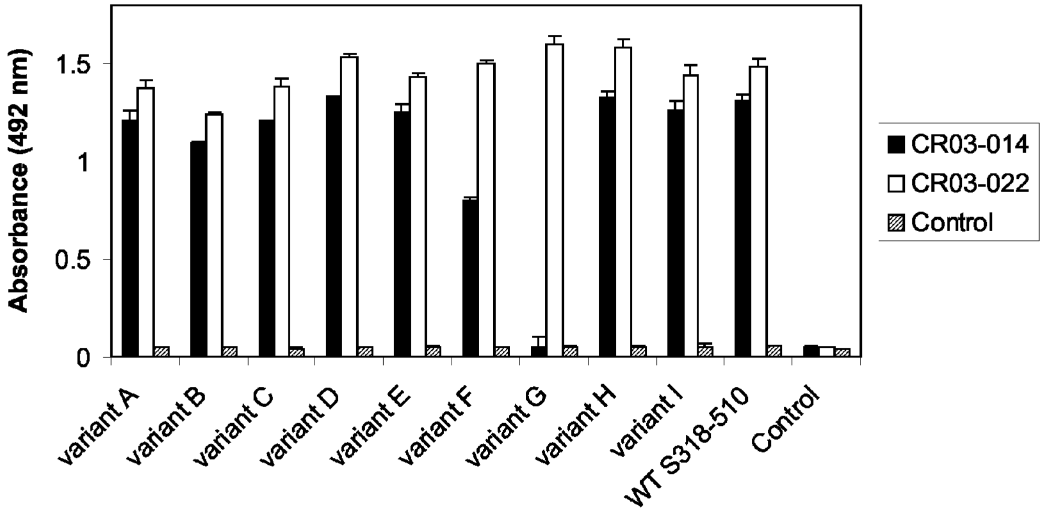
FIG. 8 shows binding of the monoclonal anti-SARS-antibodies CR03-014 and CR03-022 to the amino acid region of 318-510 of the S protein of the SARS-CoV strain Frankfurt 1 (called WT S318-510) and naturally occurring variants of the WT S318-510 fragment (variant A, mutation K344R; variant B, mutation S353F; variant C, mutations R426G and N437D; variant D, mutation Y436H; variant E, mutation Y442S; variant F, mutation N479S; variant G, mutations K344R, F360S, N479K and T487S; variant H, mutations K344R, F360S, L472P, D480G, and T487S; and variant I, mutations K344R and F501Y). The control is an irrelevant myc-His tagged protein. On the Y-axis, the absorbance at 492 nm is shown.

Construction and Evaluation of Binding of the Monoclonal Anti-SARS-CoV Antibodies to Variant S318-510 Fragments The diversity within the region 318-510 of the S protein was determined as follows. A list containing more than 146 genomes or genes encoding complete human SARS-CoV or fragments thereof was compiled. In 114 cases, an open reading frame encoding for full-length spike (S) protein was identified. Alignment of the spike amino acid residues 318-510 revealed 30 spike proteins, in which the region 318-510 was not identical to that of the spike protein of strain Frankfurt 1 (see Genbank accession number AY291315), which was used herein as wild-type. The mutations, strains and Genbank numbers are depicted in Table 15. To investigate if CR03-014 and CR03-022 bound the S protein of all currently known human SARS-CoV isolates, eight recombinant spike 318-510 fragments (variants A-F and variants H and I) harboring the different amino acid substitutions as shown in Table 15 were generated. In addition, a 318-510 fragment (variant G) corresponding to the sequence of four animal SARS-like CoVs (Genbank accession numbers AY304486-AY304489; see also Table 1, SARS-CoV SZ3, SZ13, SZ16 and SZ1, respectively) was generated. The four SARS-like CoVs, which were isolated from raccoon dogs and palm civet cats, contain the amino acid substitutions K344R, F360S, N479K and T487S (see Guan et al. 2003). To this end, the above substitutions were introduced in the pHAVT20/myc-His A S318-510 vector using the Stratagene's QuikChange II site-directed mutagenesis kit according to the manufacturer's instructions. In case a sequence contained multiple amino acid substitutions, the process of mutagenesis, sequence analysis and confirmation was repeated for every single substitution. To rule out the introduction of additional mutations in the plasmid outside the gene of interest, the mutated (592 by EcoRI-XbaI) fragment was recloned in EcoRI-XbaI cut pHAVT20/myc-His A. The resulting plasmids were transfected into HEK293T cells, and binding of CR03-014 and CR03-022 was evaluated by means of ELISA as described supra. As shown in FIG. 8, CR03-014 was capable of binding to variants A-E and variants H and I to a similar extent as to the wild-type fragment. Binding of CR03-014 to variant F (N479S substitution) was substantially lower than binding to the other fragments. No binding of CR03-014 to fragment G (K344R, F360S, N479K and T487S substitutions) was observed. Antibody CR03-022 was capable of binding all variant S318-510 fragments to a similar extent as the wild-type (non-mutated) S318-510 fragment. Together, this indicates that residue N479 is involved in binding of CR03-014, either directly by being part of the binding site of CR03-014 or indirectly by being important for the correct conformation of the binding site of CR03-014 within the S protein. Since, antibody CR03-022 is capable of binding to recombinant fragments composed of amino acid residues 318-510 of all human SARS-CoV isolates (as described in Table 15) and in addition is also capable of binding to animal SARS-like CoV, CR03-022 is suitable for treatment and/or protection against SARS-CoV isolates in general.

Particularly suitable for treatment and/or protection against human SARS-CoV isolates is a combination/cocktail comprising both antibodies, CR03-014 and CR03-022, as both antibodies are capable of specifically binding to human SARS-CoV and the antibodies act synergistically in neutralizing human SARS-CoV. In other words, the combination/cocktail of CR03-014 and CR03-022 comprises synergistic human SARS-CoV-neutralizing activity. An additional advantage of such a combination/cocktail is its capability of neutralizing human SARS-CoV as well as animal SARS-like CoV.

Example 9

Generation of CR03-014 and CR03-022 Escape Viruses of SARS-CoV

To further elucidate the epitopes recognized by the human monoclonal antibodies CR03-014 and CR03-022, escape viruses of CR03-014 and CR03-022 were generated. The process for generating escape viruses of CR03-014 is given infra. The process for generating escape viruses of CR03-022 was identical with the proviso that 60 μg/ml antibody instead of 20 μg/ml was used in all respective steps. Serial dilutions (0.5 ml) of SARS-CoV strain HKU 39849 (dilutions ranging from $10^{-1}$-$10^{-8}$) were incubated with a constant amount (20 μg/ml giving an approximate three log reduction of $TCID_{50}$/ml) of antibody CR03-014 (0.5 ml) for one hour at 37° C./5% $CO_2$ before addition to wells containing FRhK-4 cells. The virus was allowed to attach to the cells for one hour at 37° C./5% $CO_2$, then removed and cells were washed twice with medium. Finally, cells were incubated for two days in the presence of selecting antibody CR03-014 at 20 μg/ml in 0.5 ml medium. Then, medium of wells with highest virus dilution showing CPE (cytopathic effect) containing potential escape viruses was harvested and stored at 4° C. until further use. Subsequently, virus samples were freeze/thawed once and serial dilutions were prepared in medium. Virus dilutions were added to wells containing FRhK-4 cells and incubated for one to two hours at 37° C./5% $CO_2$ in the presence of CR03-014 at 20 μg/ml. Wells were then overlayed with agarose containing CR03-014 at 20 μg/ml and incubated for three to five days at 37° C./5% $CO_2$. Individual escape virus plaques were picked using a Pasteur pipette, freeze/thawed once, and the escape viruses were amplified on FRhK-4 cells. To analyze the escape viruses, the following experiments were performed.

Firstly, to identify possible mutations in the SARS-CoV spike protein of each of the escape viruses, the nucleotide sequence of the SARS-CoV spike open reading frame (ORF) was determined. Viral RNA of each of the escape viruses and wild-type SARS-CoV virus was isolated and converted into cDNA by standard RT-PCR. Subsequently, the cDNA was used for nucleotide sequencing of the SARS-CoV spike ORF in order to identify mutations. FIG. 9 shows the results of the sequencing data for the five E014 escape viruses obtained. All escape viruses contained a nucleotide mutation at position 1385 (C to T), which resulted in an amino acid mutation P to L at position 462 in the spike protein. Apparently, P462L resulted in loss of epitope recognition and, subsequently, loss of neutralization of SARS-CoV by CR03-014. This indicates that next to amino acid 479, also amino acid 462 is involved in the binding of CR03-014 to the S protein of SARS-CoV. The results of the sequencing data for the five E022 escape viruses obtained were as follows. Four out of five escape viruses contained a nucleotide mutation at position 2588 (C to T), which resulted in an amino acid mutation T to I at position 863 in the spike protein.

Secondly, the neutralization index (NI) was determined for each of the E014 and E022 escape viruses. A virus was defined as an escape variant if the neutralization index was <2.5 logs. The process of determining the NI is given below for E014 escape viruses. The process was identical for E022 escape viruses with the proviso that 60 μg/ml instead of 20 μg/ml monoclonal antibody was used in all respective steps. The neutralization index was determined by subtracting the number of infectious virus particles (in TCID50/ml) produced in FRhK-4 cell cultures infected with virus plus monoclonal antibody (20 μg/ml) from the number of infectious virus particles (in TCID50/ml) produced in FRhK-4 cell cultures infected with virus alone ([log TCID50/ml virus in absence of monoclonal antibody minus log TCID50/ml virus in presence of monoclonal antibody]). An index lower than 2.5 logs was considered as evidence of escape. Therefore, each escape virus and wild-type SARS-CoV (100 TCID50) was incubated for one hour at 37° C./5% $CO_2$ with 20 μg/ml of CR03-014 before addition to FRhK-4 cells. The virus was allowed to attach to the cells for one hour at 37° C./5% $CO_2$ after which the inoculum was removed and cells were washed twice with medium before being replenished with medium containing 20 μg/ml of CR03-014. After a two-day incubation at 37° C./5% $CO_2$, the medium was harvested and the $TCID_{50}$/ml of each virus was determined. As shown in Table 16, the concentration of antibody used to determine the NI resulted in an approximate three log reduction of virus titer when performed on the wild-type SARS-CoV virus. Thus, wild-type SARS-CoV was neutralized by CR03-014 as judged by the NI of 3.3. In contrast, the NI for each escape virus was <2.5 and thus, each of the escape viruses was no longer neutralized by CR03-014. As judged by the NI of 3.3, wild-type SARS-CoV virus was also neutralized by CR03-022 (see Table 17). The NI for each E022 escape virus was >2.5 and thus, it was concluded that each of the escape viruses was still neutralized by CR03-022. The amino acid substitution in four of the five E022 escape viruses apparently does not play a role in neutralization of SARS-CoV by CR03-022. It might have been induced non-specifically during the course of the experiment. This agrees with finding by Poon et al. (2005) who observed the mutation at position 863 (T to I) when SARS-CoV was passaged multiple times in FRhK-4 cells. The neutralizing epitope of CR03-022 could not be determined by means of generating escape viruses. This may be caused by the functional constraints of the binding region on the S protein. A mutation occurring in this region may be detrimental to the stability of the virus and could not, therefore, be isolated in the experiments described above.

Figure 10:
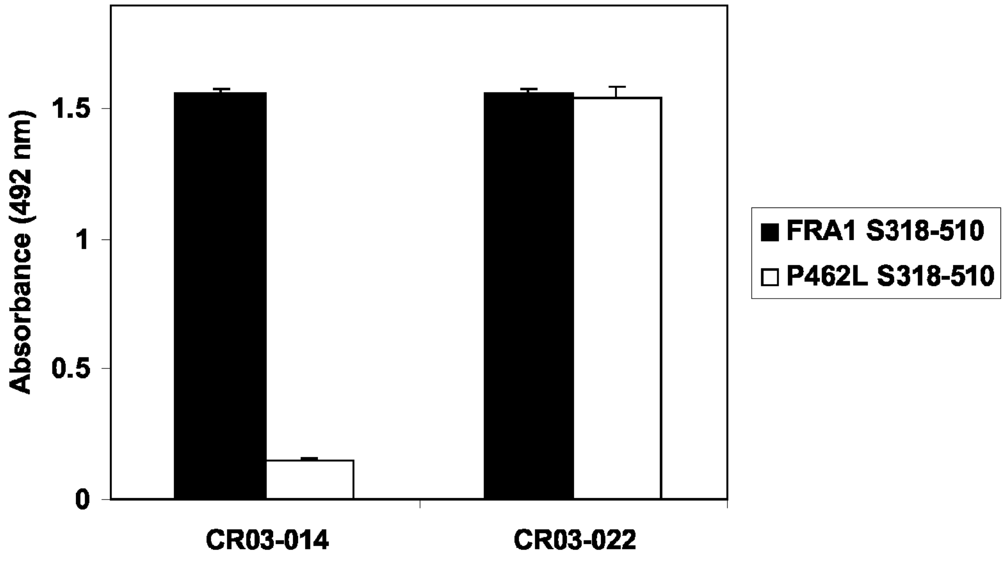
FIG. 10 shows binding of the monoclonal anti-SARS-antibodies CR03-014 and CR03-022 to the amino acid region of 318-510 of the S protein of the SARS-CoV strain Frankfurt 1 (called FRA1 S318-510) and an escape variant of antibody CR03-014 harboring a P462L substitution. On the Y-axis, the absorbance at 492 nm is shown.

In order to confirm lack of binding of antibody CR03-014 to the escape variant, a recombinant S318-510 fragment harboring the P to L substitution at position 462 was constructed essentially as described supra. DNA transfection of the resulting plasmid was performed in HEK293T cells for transient expression and the fragments were directly used from culture supernatant. The ELISA was performed as described supra. Briefly, the fragments were captured on anti-myc-coated microtiter wells. Subsequently, antibodies CR03-014 and CR03-022 were added and binding of the antibodies was detected using an anti-human IgG HRP-conjugate. As shown in FIG. 10, antibody CR03-014 was not able to bind the S318-510 fragment carrying a P to L substitution at position 462. Binding of CR03-022 was not affected by this amino acid substitution. This further indicates that antibody CR03-022 is capable of binding to a different/distinct, non-competing epitope on the S protein and suggests that CR03-022 might be used to compensate potential lack of neutralization of SARS-CoV variants by CR03-014.

Furthermore, cross-neutralization assays were performed on E14 escape viruses. Table 18 clearly shows that CR03-022 neutralized the E14 escape viruses to a similar level as wild-type virus, further illustrating that CR03-022 binds to a different epitope compared to CR03-014, which no longer neutralized the E14 escape viruses. This result is in agreement with the ELISA data shown in FIG. 10. The reverse experiment could not be performed as escape viruses of CR03-022 could not be generated. From the foregoing, it can be concluded that the combination of CR03-014 and CR03-022 in a cocktail prevents the escape of neutralization-resistant SARS-CoV variants and is, therefore, an ideal immunoglobulin preparation for SARS-CoV prophylaxis and therapy.

Example 10

Assessment of Potential Enhancement of SARS-CoV Infection in Human Macrophages by the Human Anti-SARS Monoclonal Antibody CR03-014

It is known that in certain diseases caused by coronaviruses, prior immunity or passive antibody increases the severity of the disease. In feline infectious peritonitis, the macrophage is the main target cell for virus replication and antiviral antibodies enhance replication of the virus in macrophage cultures in vitro. The macrophage is also a prominent cell seen in the cell infiltrates of lungs of patients dying of SARS-CoV (Nicholls et al. 2003). This has led to concern whether antibody-dependent enhancement (ADE) may be relevant in the pathogenesis of SARS-CoV. To investigate this, it was tested whether ADE occurred when macrophages were infected with SARS-CoV in the presence of the neutralizing anti-SARS-CoV monoclonal antibody CR03-014, the non-neutralizing anti-SARS-CoV monoclonal antibody CR-03-015, the monoclonal antibody called CR-JA a monoclonal antibody against rabies that is used herein as a control antibody), convalescent serum from an individual exposed to SARS-CoV, and serum from a healthy individual.

Human peripheral blood mononuclear cells (PBMCs) were obtained from leukocyte-rich buffy coats of healthy blood donors (The Hong Kong Red Cross Blood Transfusion Service, Hong Kong). The PBMCs were separated by Ficoll-Paque gradient centrifugation (Pharmacia Biotech, Uppsala, Sweden). To isolate monocytes, $2\times10^7$ PBMCs were allowed to adhere onto petri dishes (Greiner, Frickenhausen, Germany) for one hour in RPMI 1640 medium supplemented with 20 mM HEPES, 2 mM glutamine, 0.6 μg/ml penicillin, and 60 μg/ml streptomycin and 5% heat-inactivated autologous plasma. After washing with medium, the adherent monocytes were detached by pipetting and re-seeded into 24-well plates at a density of $2\times10^5$ cells per well in supplemented RPMI 1640 medium.

To check the purity of the monocyte preparations, monocytes were also seeded and allowed to adhere onto glass coverslips. The purity of the monocytes on the glass coverslips was confirmed by staining with a CD14 R-phycoerythrin (R-PE)-conjugated mouse anti-human monoclonal antibody (BD Biosciences, San Diego, U.S.A.).

Medium in the monocyte cultures was replaced every two to three days and the cells were allowed to differentiate for 14 days in vitro. Differentiation of monocytes into macrophages was confirmed by the typical morphology of macrophages. The obtained primary human monocyte-derived macrophages were used in further experiments. Two days prior to the ADE experiments, the supplemented RPMI 1640 medium was exchanged into Macrophage Serum Free medium (SFM) (Invitrogen, Carlsbad, Calif., U.S.A.).

To investigate the effect of sub-neutralizing doses of antibody on viral infection in macrophages, 300 μl of serial ten-fold dilutions in MM medium (MEM including 1% FCS and 0.6 μg/ml penicillin, and 60 μg/ml streptomycin) of the monoclonal antibodies CR03-014, CR03-015 and CR-JA, convalescent serum from a SARS-CoV-exposed individual and serum from a healthy individual was mixed with 300 μl of SARS-CoV. MM medium mixed with SARS-CoV served as the virus control. The virus/monoclonal antibody mixtures and virus/serum mixtures were incubated for one hour at 37° C. Then, 250 μl of the mixtures was added to duplicate wells containing macrophages. After one hour of virus adsorption at 37° C., the virus inoculum was removed, infected cells were washed with macrophage SFM culture medium and incubated in macrophage SFM medium supplemented with 0.6 μg/ml penicillin and 60 μg/ml streptomycin. Samples of the culture supernatants were collected at days 0, 1, 2, 3, 5, and 7 post-infection and stored at −70° C. for virus titration experiments. SARS-CoV was titrated and the TCID50 determined essentially as described supra.

To detect virus inside the macrophages (due to abortive infection) and to detect potential transcription of SARS-CoV RNA inside the macrophages, RNA was isolated from infected macrophages at 3, 6, and 24 hours post-infection using the RNeasy Mini kit (Qiagen) according to the manufacturer's instructions. Reverse transcription with oligo-dT primers was performed by using Superscript II reverse transcriptase (Invitrogen) according to the manufacturer's instructions. Complementary DNA was generated with 10 μl of RNA, and reverse-transcribed by 200 U of Superscript II reverse transcriptase (Invitrogen) in a 20 μl reaction containing 25 ng oligo-$dT_{12-18}$ primer, 10 mM dithiothreitol, and 0.5 mM deoxynucleotide triphosphates. Reactions were incubated at 42° C. for 50 minutes, followed by a heat inactivation step (72° C. for 15 minutes). The reaction mix was diluted ten times by the addition of 180 μl buffer AE (Qiagen) and stored at −20° C.

Real time quantitative PCR was performed using FastStart DNA Master SYBR Green I fluorescence reaction (Roche). Five μl of diluted complementary DNA was amplified in a 20 μl reaction containing 4 mM of $MgCl_2$, 0.5 mM of forward primer (Actin-LF: CCCAAGGCCAACCGCGAGAAGAT (SEQ ID NO:122)), and 0.5 mM of reverse primer (Actin-LR: GTCCCGGCCAGCCAGGTCCAG (SEQ ID NO:123)). Reactions were performed in a LightCycler (Roche) with the following conditions: 10 minutes at 95° C., followed by 40 cycles of 95° C. for 0 seconds, 66° C. for 5 seconds, and 72° C. for 9 seconds. Plasmids containing the target sequence were used as positive controls. Fluorescence signals from these reactions were captured at the end of the extension step in each cycle (87° C.). To determine the specificity of the assay, PCR products were subjected to melting curve analysis at the end of the assay (65° C. to 95° C.; 2° C./second). Reverse transcription with sense (negative strand detection) or anti-sense (positive strand detection) primers to the polymerase gene of SARS-CoV was achieved by using Superscript II reverse transcriptase (Invitrogen) according to the manufacturer's instructions. Complementary DNA was generated with 5 μL of RNA, and reverse-transcribed by 200 U of Superscript II reverse transcriptase (Invitrogen) in a 20 μl reaction containing 0.1 μM gene-specific primer, 10 mM dithiothreitol, and 0.5 mM deoxynucleotide triphosphates. Reactions were incubated at 42° C. for 50 minutes, followed by a heat inactivation step (72° C. for 15 minutes). The reaction was diluted ten times by the addition of 180 μL buffer AE (Qiagen) and stored at −20° C. Two μl of diluted complementary DNA was amplified in 20 μl containing 3.5 mM of $MgCl_2$, 0.25 μM of forward primer (coro3: 5'-TACACACCTCAGCGTTG-3' (SEQ ID NO:124)), and 0.25 μM of reverse primer (coro4: 5'-CACGAACGTGACGAAT-3' (SEQ ID NO:125)). Reactions were performed in a LightCycler (Roche) with the following conditions: 10 minutes at 95° C., followed by 50 cycles of 95° C. for 10 seconds, 60° C. for 5 seconds, and 72° C. for 9 seconds. Plasmids containing the target sequence were used as positive controls. Fluorescence signals from these reactions were captured at the end of the extension step in each cycle. To determine the specificity of the assay, PCR products were subjected to melting curve analysis at the end of the assay (65° C. to 95° C.; 0.1° C./seconds). Data for viral RNA were normalized for RNA levels of β-actin housekeeping gene.

After infection of macrophages with SARS-CoV, the cells were monitored daily under the microscope. Ten days after infection with SARS-CoV, no detectable cytopathic effect was detected, nor was the abortive infection of macrophages converted into a productive infection. Pre-incubating of SARS-CoV with different concentrations of the monoclonal antibodies CR03-014, CR03-015, CR-JA, convalescent serum or serum from a healthy individual, prior to infection of macrophages did not change this outcome.

Titration of aliquots of supernatant taken from infected macrophage culture at days 0, 1, 2, 3, 5, and 7 post-infection on FRhk-4 cells revealed no evidence of significant enhancement of SARS-CoV replication in macrophages by the monoclonal antibodies and sera tested (data not shown).

In addition, the effect of antibodies on the (abortive) infection of macrophages by SARS-CoV and the transcription of SARS-CoV genes within the macrophages was measured on the molecular level. To this end, total RNA was extracted from the infected macrophages at various time points post-infection as described supra. Subsequently, total RNA was analyzed for SARS-CoV viral positive strand RNA and viral negative strand RNA transcripts using real-time RT-PCR. The SARS-CoV RNA levels were normalized for the levels of β-actin mRNA. The results show that positive strand SARS-CoV RNA was detected in all macrophage cultures that were incubated with SARS-CoV, which confirms the abortive infection of macrophages by SARS-CoV. The levels of positive strand RNA observed in macrophage cultures infected with SARS-CoV in the presence of anti-SARS-CoV monoclonal antibodies CR03-014 or CR03-015 or convalescent serum were not significantly higher than in macrophage cultures infected with SARS-CoV in the presence of control monoclonal antibody CR-JA or serum from a healthy individual or in the absence of monoclonal antibody or serum (data not shown).

Furthermore, the presence of negative strand RNA that is indicative for SARS-CoV gene transcriptional activity after infection of macrophages by SARS-CoV was measured. Again, no correlation between the levels of negative strand RNA and the presence or absence of anti-SARS-CoV antibodies was observed (data not shown).

Together, the experiments assaying infectious virus yield and virus-related RNA levels inside macrophages showed that there was no antibody-dependent enhancement of SARS-CoV replication in human macrophages by anti-SARS-CoV monoclonal antibodies CR03-014 and CR03-015 and anti-SARS-CoV antibodies present in convalescent serum from a SARS patient.

Example 11

Identification of Epitopes Recognized by Recombinant Human Anti-SARS-CoV Antibodies by PEPSCAN-ELISA Fifteen-mer linear and looped/cyclic peptides were synthesized from proteins of SARS-CoV and screened using credit-card format mini-PEPSCAN cards (455 peptide formats/card) as described previously (see inter alia WO 84/03564, WO 93/09872, Slootstra et al. 1996). All peptides were acetylated at the amino terminus. In short, series of overlapping peptides, which were either in linear form or in looped/cyclic form, of the spike protein of SARS-CoV Urbani (the protein-id of the surface spike glycoprotein in the EMBL-database is AAP 13441), was produced and tested for binding to the recombinant human anti-SARS-CoV antibodies of the invention by means of PEPSCAN analysis.

Because the Urbani spike protein indicated above was also found in identical or highly homologous form in other SARS-CoV strains, the antigenic peptides found in the analysis method may not only be used for detection of the SARS-CoV strain Urbani and the prevention and/or treatment of a condition resulting from the SARS-CoV strain Urbani, but may also be useful in detecting SARS-CoV in general and preventing and/or treating a condition resulting from SARS-CoV in general. The protein-id of the surface spike glycoprotein of, for instance, the SARS-CoV strains TOR2, Frankfurt 1 and HSR 1 in the EMBL-database is AAP41037, AAP33697 and AAP72986. The accession number in the EMBL-database of the complete genome of the strains TOR2, Frankfurt 1 and HSR 1 is AY274119, AY291315 and AY323977, respectively. Under these accession numbers, the amino acid sequence of the other (potential) proteins of these strains can be found.

In all looped peptides, position-2 and position-14 were replaced by a cysteine (acetyl-XCXXXXXXXXXXXCX-minicard). If other cysteines besides the cysteines at position-2 and position-14 were present in a prepared peptide, the other cysteines were replaced by an alanine. The looped peptides were synthesized using standard Fmoc-chemistry and deprotected using trifluoric acid with scavengers. Subsequently, the deprotected peptides were reacted on the cards with an 0.5 mM solution of 1,3-bis(bromomethyl)benzene in ammonium bicarbonate (20 mM, pH 7.9/acetonitril (1:1 (v/v)). The cards were gently shaken in the solution for 30 to 60 minutes, while completely covered in the solution. Finally, the cards were washed extensively with excess of $H_2O$ and sonicated in disrupt-buffer containing 1% SDS/0.1% beta-mercaptoethanol in PBS (pH 7.2) at 70° C. for 30 minutes, followed by sonication in $H_2O$ for another 45 minutes.

Recombinant human anti-SARS-CoV antibodies CR03-014 and CR03-022 were tested for binding to each linear and looped peptide in a PEPSCAN-based enzyme-linked immuno assay (ELISA). The 455-well credit-card format polypropylene cards containing the covalently linked peptides were incubated with the antibodies (1-10 μg/ml; diluted in blocking solution which contains 5% horse-serum (v/v) and 5% ovalbumin (w/v)) (4° C., overnight). After washing, the peptides were incubated with anti-human antibody peroxidase (dilution 1/1000) (one hour, 25° C.), and subsequently, after washing the peroxidase substrate, 2,2'-azino-di-3-ethylbenzthiazoline sulfonate (ABTS) and 2 μl/ml 3% $H_2O_2$ were added. Controls (for linear and looped) were incubated with anti-human antibody peroxidase only. After one hour, the color development was measured. The color development of the ELISA was quantified with a CCD-camera and an image processing system. The set-up consisted of a CCD-camera and a 55 mm lens (Sony CCD Video Camera XC-77RR, Nikon micro-nikkor 55 mm f/2.8 lens), a camera adaptor (Sony Camera adaptor DC-77RR) and the Image Processing Software package Optimas, version 6.5 (Media Cybernetics, Silver Spring, Md. 20910, U.S.A.). Optimas runs on a pentium II computer system.

The recombinant human anti-SARS-CoV-antibodies CR03-014 and CR03-022 were tested for binding to the 15-mer linear and looped/cyclic peptides synthesized as described supra. Relevant binding of a peptide to a recombinant human anti-SARS-CoV antibody was calculated as follows. The average OD-value for each antibody was calculated for the respective proteins (sum of OD-values of all peptides/total number of peptides). Next, the standard deviation of this average was calculated. The standard deviation was multiplied by two and the obtained value was added to the average value to obtain the correction factor. The OD-value of each peptide was then divided by this correction factor. If a value of 0.9 or higher was found, then relevant binding was considered to be present between the specific peptide and the respective antibody. Particularly interesting appear to be domains comprising several reactive peptides, i.e., domains comprising consecutive peptides, wherein at least most of the peptides in the domains are reactive with the antibody.

Monoclonal antibody CR03-014 did not appear to react specifically with a peptide or domains comprising several peptides within the SARS-CoV spike protein, indicating that CR03-014 may recognize a discontinuous non-linear epitope. Monoclonal antibody CR03-022 reacted with a series of looped peptides in two domains (data not shown). The domains are comprised of amino acid residues 430-449 and 484-503 of the SARS-CoV spike protein and have the amino acid sequences ATSTGNYNYKYRYLRHGKLR (SEQ ID NO:126) and YTTTGIGYQPYRVVVLSFEL (SEQ ID NO:127), respectively. Strikingly, both domains have the motif TXTGXXXXXYR (SEQ ID NO:128) in common, indicating that this motif may be crucial for the binding of antibody CR03-022 to the SARS-CoV spike protein.

TABLE 1

List of currently known SARS-CoV genome sequence and spike genes.

| SARS isolate | Gene/genome | Genbank | FASTA |
|---|---|---|---|
| SARS coronavirus AS | SARS coronavirus AS, complete genome. | AY427439 | 37576845 |
| SARS coronavirus BJ01 | SARS coronavirus BJ01, complete genome. | AY278488 | 30275666 |
| SARS coronavirus BJ02 | SARS coronavirus BJ02, complete genome. | AY278487 | 31416292 |
| SARS coronavirus BJ03 | SARS coronavirus BJ03, complete genome. | AY278490 | 31416305 |
| SARS coronavirus BJ04 | SARS coronavirus BJ04, complete genome. | AY279354 | 31416306 |
| SARS coronavirus BJ2232 | | | |
| SARS coronavirus BJ302 | | | |
| SARS coronavirus CUHK-AG01 | SARS coronavirus CUHK-AG01, complete genome. | AY345986 | 33114190 |
| SARS coronavirus CUHK-AG02 | SARS coronavirus CUHK-AG02, complete genome. | AY345987 | 33114202 |
| SARS coronavirus CUHK-AG03 | SARS coronavirus CUHK-AG03, complete genome. | AY345988 | 33114214 |
| SARS coronavirus CUHK-L2 | | | |
| SARS coronavirus CUHK-Su10 | SARS coronavirus CUHK-Su10, complete genome. | AY282752 | 38304867 |
| SARS coronavirus CUHK-W1 | SARS coronavirus CUHK-W1, complete genome. | AY278554 | 30027610 |
| SARS coronavirus cw037 | | | |
| SARS coronavirus cw049 | | | |
| SARS coronavirus FRA | SARS coronavirus FRA, complete genome. | AY310120 | 33578015 |
| SARS coronavirus Frankfurt 1 | SARS coronavirus Frankfurt 1, complete genome. | AY291315 | 31581502 |
| SARS coronavirus GD01 | SARS coronavirus GD01, complete genome. | AY278489 | 31416290 |
| SARS coronavirus GD03T0013 | SARS coronavirus GD03T0013 spike glycoprotein gene, complete cds. | AY525636 | 41764105 |
| SARS coronavirus GD69 | SARS coronavirus GD69, complete genome. | AY313906 | 37960831 |
| SARS coronavirus GZ-A | SARS coronavirus GZ-A, partial genome. | AY394977 | 37624320 |
| SARS coronavirus GZ-B | SARS coronavirus GZ-B, complete genome. | AY394978 | 37624321 |
| SARS coronavirus GZ-C | SARS coronavirus GZ-C, complete genome. | AY394979 | 37624322 |
| SARS coronavirus GZ-D | SARS coronavirus GZ-D, partial genome. | AY394980 | 37624323 |
| SARS coronavirus GZ02 | SARS coronavirus GZ02, complete genome. | AY390556 | 41323719 |
| SARS coronavirus GZ43 | SARS coronavirus GZ43, partial genome. | AY304490 | 34482141 |
| SARS coronavirus GZ50 | SARS coronavirus GZ50, complete genome. | AY304495 | 34482146 |
| SARS coronavirus GZ60 | SARS coronavirus GZ60, partial genome. | AY304491 | 34482142 |
| SARS coronavirus HB | | | |
| SARS coronavirus HGZ8L1-A | SARS coronavirus HGZ8L1-A, partial genome. | AY394981 | 37624324 |
| SARS coronavirus HGZ8L1-B | SARS coronavirus HGZ8L1-B, partial genome. | AY394982 | 37624325 |
| SARS coronavirus HGZ8L2 | SARS coronavirus HGZ8L2, complete genome. | AY394993 | 37624336 |
| SARS coronavirus HKU-36871 | SARS coronavirus HKU-36871, partial genome. | AY304492 | 34482143 |
| SARS coronavirus HKU-39849 | SARS coronavirus HKU-39849, complete genome. | AY278491 | 30023963 |
| SARS coronavirus HKU-65806 | SARS coronavirus HKU-65806, partial genome. | AY304493 | 34482144 |
| SARS coronavirus HKU-66078 | SARS coronavirus HKU-66078, partial genome. | AY304494 | 34482145 |
| SARS coronavirus Hong Kong/03/2003 | | | |
| SARS coronavirus HPZ-2003 | | | |
| SARS coronavirus HSR 1 | SARS coronavirus HSR 1, complete genome. | AY323977 | 33115118 |
| SARS coronavirus HSZ-A | SARS coronavirus HSZ-A, partial genome. | AY394984 | 37624327 |
| SARS coronavirus HSZ-Bb | SARS coronavirus HSZ-Bb, complete genome. | AY394985 | 37624328 |
| SARS coronavirus HSZ-Bc | SARS coronavirus HSZ-Bc, complete genome. | AY394994 | 37624337 |
| SARS coronavirus HSZ-Cb | SARS coronavirus HSZ-Cb, complete genome. | AY394986 | 37624329 |
| SARS coronavirus HSZ-Cc | SARS coronavirus HSZ-Cc, complete genome. | AY394995 | 37624338 |
| SARS coronavirus HSZ2-A | SARS coronavirus HSZ2-A, complete genome. | AY394983 | 37624326 |
| SARS coronavirus HZS2-Bb | SARS coronavirus HZS2-Bb, partial genome. | AY395004 | 37624347 |
| SARS coronavirus HZS2-C | SARS coronavirus HZS2-C, complete genome. | AY394992 | 37624335 |
| SARS coronavirus HZS2-D | SARS coronavirus HZS2-D, complete genome. | AY394989 | 37624332 |
| SARS coronavirus HZS2-E | SARS coronavirus HZS2-E, complete genome. | AY394990 | 37624333 |
| SARS coronavirus HZS2-Fb | SARS coronavirus HZS2-Fb, complete genome. | AY394987 | 37624330 |
| SARS coronavirus HZS2-Fc | SARS coronavirus HZS2-Fc, complete genome. | AY394991 | 37624334 |
| SARS coronavirus JMD | SARS coronavirus JMD, partial genome. | AY394988 | 37624331 |
| SARS coronavirus LC1 | SARS coronavirus LC1, complete genome. | AY394998 | 37624341 |
| SARS coronavirus LC2 | SARS coronavirus LC2, complete genome. | AY394999 | 37624342 |
| SARS coronavirus LC3 | SARS coronavirus LC3, complete genome. | AY395000 | 37624343 |
| SARS coronavirus LC4 | SARS coronavirus LC4, complete genome. | AY395001 | 37624344 |
| SARS coronavirus LC5 | SARS coronavirus LC5, complete genome. | AY395002 | 37624345 |
| SARS coronavirus NS-1 | SARS coronavirus NS-1, complete genome. | AY508724 | 40795744 |
| SARS coronavirus PUMC01 | SARS coronavirus PUMC01, complete genome. | AY350750 | 38231927 |
| SARS coronavirus PUMC02 | SARS coronavirus PUMC02, complete genome. | AY357075 | 38231932 |
| SARS coronavirus PUMC03 | SARS coronavirus PUMC03, complete genome. | AY357076 | 38231937 |
| SARS coronavirus sf098 | | | |
| SARS coronavirus sf099 | | | |
| SARS coronavirus ShanghaiQXC1 | SARS coronavirus ShanghaiQXC1, complete genome. | AY463059 | 40457433 |

TABLE 1-continued

List of currently known SARS-CoV genome sequence and spike genes.

| SARS isolate | Gene/genome | Genbank | FASTA |
|---|---|---|---|
| SARS coronavirus ShanghaiQXC2 | SARS coronavirus ShanghaiQXC2, complete genome. | AY463060 | 40457448 |
| SARS coronavirus Shanhgai LY | SARS coronavirus Shanhgai LY spike glycoprotein gene, complete cds. | AY322205S3 | 32454341 |
| SARS coronavirus Sin0409 | | | |
| SARS coronavirus Sin2500 | SARS coronavirus Sin2500, complete genome. | AY283794 | 30468042 |
| SARS coronavirus Sin2677 | SARS coronavirus Sin2677, complete genome. | AY283795 | 30468043 |
| SARS coronavirus Sin2679 | SARS coronavirus Sin2679, complete genome. | AY283796 | 30468044 |
| SARS coronavirus Sin2748 | SARS coronavirus Sin2748, complete genome. | AY283797 | 30468045 |
| SARS coronavirus Sin2774 | SARS coronavirus Sin2774, complete genome. | AY283798 | 37361915 |
| SARS coronavirus Sin3408 | SARS coronavirus Sin3408, complete genome | AY559083 | 45644998 |
| SARS coronavirus Sin3408L | SARS coronavirus Sin3408L, complete genome | AY559097 | 45645024 |
| SARS coronavirus Sin3725V | SARS coronavirus Sin3725V, complete genome | AY559087 | 45645004 |
| SARS coronavirus Sin3765V | SARS coronavirus Sin3765V, complete genome | AY559084 | 45645000 |
| SARS coronavirus Sin842 | SARS coronavirus Sin842, complete genome | AY559081 | 45644994 |
| SARS coronavirus Sin845 | SARS coronavirus Sin845, complete genome | AY559093 | 45645019 |
| SARS coronavirus Sin846 | SARS coronavirus Sin846, complete genome | AY559094 | 45645021 |
| SARS coronavirus Sin847 | SARS coronavirus Sin847, complete genome | AY559095 | 45645022 |
| SARS coronavirus Sin848 | SARS coronavirus Sin848, complete genome | AY559085 | 45645001 |
| SARS coronavirus Sin849 | SARS coronavirus Sin849, complete genome | AY559086 | 45645003 |
| SARS coronavirus Sin850 | SARS coronavirus Sin850, complete genome | AY559096 | 45645023 |
| SARS coronavirus Sin852 | SARS coronavirus Sin852, complete genome | AY559082 | 45644996 |
| SARS coronavirus Sin_WNV | | | |
| SARS coronavirus Sino1-11 | SARS coronavirus Sino1-11, complete genome. | AY485277 | 38505482 |
| SARS coronavirus Sino3-11 | SARS coronavirus Sino3-11, complete genome. | AY485278 | 38505491 |
| SARS coronavirus SinP1 | SARS coronavirus SinP1, complete genome | AY559088 | 45645007 |
| SARS coronavirus SinP2 | SARS coronavirus SinP2, complete genome | AY559089 | 45645010 |
| SARS coronavirus SinP3 | SARS coronavirus SinP3, complete genome | AY559090 | 45645013 |
| SARS coronavirus SinP4 | SARS coronavirus SinP4, complete genome | AY559091 | 45645016 |
| SARS coronavirus SinP5 | SARS coronavirus SinP5, complete genome | AY559092 | 45645017 |
| SARS coronavirus SoD | SARS coronavirus SoD, complete genome. | AY461660 | 38385714 |
| SARS coronavirus SZ1 | SARS coronavirus SZ1, partial genome. | AY304489 | 34482140 |
| SARS coronavirus SZ13 | SARS coronavirus SZ13, partial genome. | AY304487 | 34482138 |
| SARS coronavirus SZ16 | SARS coronavirus SZ16, complete genome. | AY304488 | 34482139 |
| SARS coronavirus SZ3 | SARS coronavirus SZ3, complete genome. | AY304486 | 34482137 |
| SARS coronavirus Taiwan | | | |
| SARS coronavirus Taiwan JC-2003 | | | |
| SARS coronavirus Taiwan TC1 | SARS coronavirus Taiwan TC1, complete genome. | AY338174 | 32493129 |
| SARS coronavirus Taiwan TC2 | SARS coronavirus Taiwan TC2, complete genome. | AY338175 | 32493130 |
| SARS coronavirus Taiwan TC3 | SARS coronavirus Taiwan TC3, complete genome. | AY348314 | 33188324 |
| SARS coronavirus Tor2 | SARS coronavirus TOR2, complete genome. | AY274119 | 30248028 |
| SARS coronavirus TW | | | |
| SARS coronavirus TW-GD1 | | | |
| SARS coronavirus TW-GD2 | | | |
| SARS coronavirus TW-GD3 | | | |
| SARS coronavirus TW-GD4 | | | |
| SARS coronavirus TW-GD5 | | | |
| SARS coronavirus TW-HP1 | | | |
| SARS coronavirus TW-HP2 | | | |
| SARS coronavirus TW-HP3 | | | |
| SARS coronavirus TW-HP4 | | | |
| SARS coronavirus TW-JC2 | | | |
| SARS coronavirus TW-KC1 | | | |
| SARS coronavirus TW-KC3 | | | |
| SARS coronavirus TW-PH1 | | | |
| SARS coronavirus TW-PH2 | | | |
| SARS coronavirus TW-YM1 | | | |
| SARS coronavirus TW-YM2 | | | |
| SARS coronavirus TW-YM3 | | | |
| SARS coronavirus TW-YM4 | | | |
| SARS coronavirus TW1 | SARS coronavirus TW1, complete genome. | AY291451 | 30698326 |
| SARS coronavirus TW10 | SARS coronavirus TW10, complete genome. | AY502923 | 40548873 |
| SARS coronavirus TW11 | SARS coronavirus TW11, complete genome. | AY502924 | 40548885 |
| SARS coronavirus TW2 | SARS coronavirus TW2, complete genome. | AY502925 | 40548897 |
| SARS coronavirus TW3 | SARS coronavirus TW3, complete genome. | AY502926 | 40548909 |
| SARS coronavirus TW4 | SARS coronavirus TW4, complete genome. | AY502927 | 40548921 |
| SARS coronavirus TW5 | SARS coronavirus TW5, complete genome. | AY502928 | 40548933 |
| SARS coronavirus TW6 | SARS coronavirus TW6, complete genome. | AY502929 | 40548945 |
| SARS coronavirus TW7 | SARS coronavirus TW7, complete genome. | AY502930 | 40548957 |
| SARS coronavirus TW8 | SARS coronavirus TW8, complete genome. | AY502931 | 40548969 |
| SARS coronavirus TW9 | SARS coronavirus TW9, complete genome. | AY502932 | 40548981 |
| SARS coronavirus TWC | SARS coronavirus TWC, complete genome. | AY321118 | 31873092 |
| SARS coronavirus TWC2 | SARS coronavirus TWC2, complete genome. | AY362698 | 33518724 |
| SARS coronavirus TWC3 | SARS coronavirus TWC3, complete genome. | AY362699 | 33518725 |
| SARS coronavirus TWH | SARS coronavirus TWH genomic RNA, complete genome. | AP006557 | 33411399 |
| SARS coronavirus TWJ | SARS coronavirus TWJ genomic RNA, complete genome. | AP006558 | 33411414 |
| SARS coronavirus TWK | SARS coronavirus TWK genomic RNA, complete genome. | AP006559 | 33411429 |

TABLE 1-continued

List of currently known SARS-CoV genome sequence and spike genes.

| SARS isolate | Gene/genome | Genbank | FASTA |
|---|---|---|---|
| SARS coronavirus TWS | SARS coronavirus TWS genomic RNA, complete genome. | AP006560 | 33411444 |
| SARS coronavirus TWY | SARS coronavirus TWY genomic RNA, complete genome. | AP006561 | 33411459 |
| SARS coronavirus Urbani | SARS coronavirus Urbani, complete genome. | AY278741 | 30027617 |
| SARS coronavirus Vietnam | | | |
| SARS coronavirus WHU | SARS coronavirus WHU, complete genome. | AY394850 | 40795428 |
| SARS coronavirus xw002 | | | |
| SARS coronavirus ZJ01 | SARS coronavirus ZJ01, complete genome. | AY297028 | 30910859 |
| SARS coronavirus ZMY 1 | SARS coronavirus ZMY 1, complete genome. | AY351680 | 33304219 |
| SARS coronavirus ZS-A | SARS coronavirus ZS-A, complete genome. | AY394997 | 37624340 |
| SARS coronavirus ZS-B | SARS coronavirus ZS-B, complete genome. | AY394996 | 37624339 |
| SARS coronavirus ZS-C | SARS coronavirus ZS-C, complete genome. | AY395003 | 37624346 |
| | SARS coronavirus, TOR2 complete genome, curated | NC_004718 | 30271926 |
| | SARS coronavirus ZJ01, partial genome. | AY286320 | 39980888 |
| | SARS coronavirus BJ302 clone 1 spike glycoprotein gene, complete | AY429072 | 38016580 |
| | SARS coronavirus BJ302 clone 2 spike glycoprotein gene, complete | AY429073 | 38016582 |
| | SARS coronavirus BJ302 clone 3 spike glycoprotein gene, complete | AY429074 | 38016584 |
| | SARS coronavirus BJ302 clone 4 spike glycoprotein gene, complete | AY429075 | 38016586 |
| | SARS coronavirus BJ302 clone 5 spike glycoprotein gene, complete | AY429076 | 38016588 |
| | SARS coronavirus BJ302 clone 6 spike glycoprotein gene, complete | AY429077 | 38016590 |
| | SARS coronavirus BJ302 clone 7 spike glycoprotein gene, complete | AY429078 | 38016592 |
| | SARS coronavirus BJ302 clone 8 spike glycoprotein gene, complete | AY429079 | 38016594 |

TABLE 2

Human IgG heavy chain variable region primers (sense).

| Primer name | Primer nucleotide sequence | SEQ ID NO |
|---|---|---|
| HuVH1B/7A | 5'-CAGRTGCAGCTGGTG CARTCTGG-3' | SEQ ID NO: 11 |
| HuVH1C | 5'-SAGGTCCAGCTGGTR CAGTCTGG-3' | SEQ ID NO: 12 |
| HuVH2B | 5'-SAGGTGCAGCTGGTG GAGTCTGG-3' | SEQ ID NO: 13 |
| HuVH3B | 5'-SAGGTGCAGCTGGTG GAGTCTGG-3' | SEQ ID NO: 14 |
| HuVH3C | 5'-GAGGTGCAGCTGGTG GAGWCYGG-3' | SEQ ID NO: 15 |
| HuVH4B | 5'-CAGGTGCAGCTACAG CAGTGGGG-3' | SEQ ID NO: 16 |
| HuVH4C | 5'-CAGSTGCAGCTGCAG GAGTCSGG-3' | SEQ ID NO: 17 |
| HuVH5B | 5'-GARGTGCAGCTGGTG CAGTCTGG-3' | SEQ ID NO: 18 |
| HuVH6A | 5'-CAGGTACAGCTGCAG CAGTCAGG-3' | SEQ ID NO: 19 |

TABLE 3

Human IgG heavy chain J-region primers (anti-sense).

| Primer name | Primer nucleotide sequence | SEQ ID NO |
|---|---|---|
| HuJH1/2 | 5'-TGAGGAGACGGTGAC CAGGGTGCC-3' | SEQ ID NO: 20 |
| HuJH3 | 5'-TGAAGAGACGGTGAC CATTGTCCC-3' | SEQ ID NO: 21 |
| HuJH4/5 | 5'-TGAGGAGACGGTGAC CAGGGTTCC-3' | SEQ ID NO: 22 |
| HuJH6 | 5'-TGAGGAGACGGTGAC CGTGGTCCC-3' | SEQ ID NO: 23 |

TABLE 4

Human IgG heavy chain variable region primers extended with SfiI/NcoI restriction sites (sense) and human IgG heavy chain J-region primers extended with XhoI/BstEII restrictio sites (anti-sense).

| Primer name | Primer nucleotide sequence | SEQ ID NO |
|---|---|---|
| HuVH1B/7A-NcoI | 5'-GTCCTCGCAACTGCG GCCCAGCCGGCCATGGCC CAGRTGCAGCTGGTGCAR TCTGG-3' | SEQ ID NO: 24 |
| HuVH1C-NcoI | 5'-GTCCTCGCAACTGCG GCCCAGCCGGCCATGGCC SAGGTCCAGCTGGTRCAG TCTGG-3' | SEQ ID NO: 25 |

TABLE 4-continued

Human IgG heavy chain variable region primers extended with SfiI/NcoI restriction sites (sense) and human IgG heavy chain J-region primers extended with XhoI/BstEII restrictio sites (anti-sense).

| Primer name | Primer nucleotide sequence | SEQ ID NO |
|---|---|---|
| HuVH2B-NcoI | 5'-GTCCTCGCAACTGCG GCCCAGCCGGCCATGGCC CAGRTCACCTTGAAGGAG TCTGG-3' | SEQ ID NO: 26 |
| HuVH3B-NcoI | 5'-GTCCTCGCAACTGCGGCC CAGCCGGCCATGGCCSAGGTG CAGCTGGTGGAGTCTGG-3' | SEQ ID NO: 27 |
| HuVH3C-NcoI | 5'-GTCCTCGCAACTGCG GCCCAGCCGGCCATGGCC GAGGTGCAGCTGGTGGAG WCYGG-3' | SEQ ID NO: 28 |
| HuVH4B-NcoI | 5'-GTCCTCGCAACTGCG GCCCAGCCGGCCATGGCC CAGGTGCAGCTACAGCAG TGGGG-3' | SEQ ID NO: 29 |
| HuVH4C-NcoI | 5'-GTCCTCGCAACTGCGGCC CAGCCGGCCATGGCCCAGSTG CAGCTGCAGGAGTCSGG-3' | SEQ ID NO: 30 |
| HuVH5B-NcoI | 5'-GTCCTCGCAACTGCG GCCCAGCCGGCCATGGCC GARGTGCAGCTGGTGCAG TCTGG-3' | SEQ ID NO: 31 |
| HuVH6A-NcoI | 5'-GTCCTCGCAACTGCG GCCCAGCCGGCCATGGCC CAGGTACAGCTGCAGCAG TCAGG-3' | SEQ ID NO: 32 |
| HuJH1/2-XhoI | 5'-GAGTCATTCTCGACTCGA GACGGTGACCAGGGTGCC-3' | SEQ ID NO: 33 |
| HuJH3-XhoI | 5'-GAGTCATTCTCGACT CGAGACGGTGACCATTGT CCC-3' | SEQ ID NO: 34 |
| HuJH4/5-XhoI | 5'-GAGTCATTCTCGACT CGAGACGGTGACCAGGGT TCC-3' | SEQ ID NO: 35 |
| HuJH6-XhoI | 5'-GAGTCATTCTCGACTCGA GACGGTGACCGTGGTCCC-3' | SEQ ID NO: 36 |

TABLE 5

Human lambda chain variable region primers (sense).

| Primer name | Primer nucleotide sequence | SEQ ID NO |
|---|---|---|
| HuVλ1A | 5'-CAGTCTGTGCTGACT CAGCCACC-3' | SEQ ID NO: 37 |
| HuVλ1B | 5'-CAGTCTGTGYTGACG CAGCCGCC-3' | SEQ ID NO: 38 |
| HuVλ1C | 5'-CAGTCTGTCGTGACG CAGCCGCC-3' | SEQ ID NO: 39 |
| HuVλ2 | 5'-CARTCTGCCCTGACT CAGCCT-3' | SEQ ID NO: 40 |

TABLE 5-continued

Human lambda chain variable region primers (sense).

| Primer name | Primer nucleotide sequence | SEQ ID NO |
|---|---|---|
| HuVλ3A | 5'-TCCTATGWGCTGACT CAGCCACC-3' | SEQ ID NO: 41 |
| HuVλ3B | 5'-TCTTCTGAGCTGACT CAGGACCC-3' | SEQ ID NO: 42 |
| HuVλ4 | 5'-CACGTTATACTGACT CAACCGCC-3' | SEQ ID NO: 43 |
| HuVλ5 | 5'-CAGGCTGTGCTGACT CAGCCGTC-3' | SEQ ID NO: 44 |
| HuVλ6 | 5'-AATTTTATGCTGACT CAGCCCCA-3' | SEQ ID NO: 45 |
| HuVλ7/8 | 5'-CAGRCTGTGGTGACY CAGGAGCC-3' | SEQ ID NO: 46 |
| HuVλ9 | 5'-CWGCCTGTGCTGACT CAGCCMCC-3' | SEQ ID NO: 47 |

TABLE 6

Human kappa chain variable region primers (sense).

| Primer name | Primer nucleotide sequence | SEQ ID NO |
|---|---|---|
| HuVκ1B | 5'-GACATCCAGWTGACCC AGTCTCC-3' | SEQ ID NO: 48 |
| HuVκ2 | 5'-GATGTTGTGATGACT CAGTCTCC-3' | SEQ ID NO: 49 |
| HuVκ3 | 5'-GAAATTGTGWTGACR CAGTCTCC-3' | SEQ ID NO: 50 |
| HuVκ4 | 5'-GATATTGTGATGACC CACACTCC-3' | SEQ ID NO: 51 |
| HuVκ5 | 5'-GAAACGACACTCACG CAGTCTCC-3' | SEQ ID NO: 52 |
| HuVκ6 | 5'-GAAATTGTGCTGACTC AGTCTCC-3' | SEQ ID NO: 53 |

TABLE 7

Human lambda chain J-region primers (anti-sense).

| Primer name | Primer nucleotide sequence | SEQ ID NO |
|---|---|---|
| HuJλ1 | 5'-ACCTAGGACGGTGACC TTGGTCCC-3' | SEQ ID NO: 54 |
| HuJλ2/3 | 5'-ACCTAGGACGGTCAG CTTGGTCCC-3' | SEQ ID NO: 55 |
| HuJλ4/5 | 5'-ACYTAAAACGGTGAG CTGGGTCCC-3' | SEQ ID NO: 56 |

TABLE 8

Human lambda chain J-region primers (anti-sense).

| Primer name | Primer nucleotide sequence | SEQ ID NO |
|---|---|---|
| HuJκ1 | 5'-ACGTTTGATTTCCAC CTTGGTCCC-3' | SEQ ID NO: 57 |
| HuJκ2 | 5'-ACGTTTGATCTCCAG CTTGGTCCC-3' | SEQ ID NO: 58 |
| HuJκ3 | 5'-ACGTTTGATATCCAC TTTGGTCCC-3' | SEQ ID NO: 59 |
| HuJκ4 | 5'-ACGTTTGATCTCCAC CTTGGTCCC-3' | SEQ ID NO: 60 |
| HuJκ5 | 5'-ACGTTTAATCTCCAG TCGTGTCCC-3' | SEQ ID NO: 61 |

TABLE 9

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO |
|---|---|---|
| HuVκ1B-SalI | 5'-TGAGCACACAGGTCG ACGGACATCCAGWTGACC CAGTCTCC-3' | SEQ ID NO: 62 |
| HuVκ2-SalI | 5'-TGAGCACACAGGTCG ACGGATGTTGTGATGACT CAGTCTCC-3' | SEQ ID NO: 63 |
| HuVκ3B-SalI | 5'-TGAGCACACAGGTCG ACGGAAATTGTGWTGACR CAGTCTCC-3' | SEQ ID NO: 64 |
| HuVκ4B-SalI | 5'-TGAGCACACAGGTCG ACGGATATTGTGATGACC CACACTCC-3' | SEQ ID NO: 65 |
| HuVκ5-SalI | 5'-TGAGCACACAGGTCGACG GAAACGACACTCACGCAGTCT CC-3' | SEQ ID NO: 66 |
| HuVκ6-SalI | 5'-TGAGCACACAGGTCG ACGGAAATTGTGCTGACT CAGTCTCC-3' | SEQ ID NO: 67 |
| HuJκ1-NotI | 5'-GAGTCATTCTCGACTTGC GGCCGCACGTTTGATTTCCAC CTTGGTCCC-3' | SEQ ID NO: 68 |
| HuJκ2-NotI | 5'-GAGTCATTCTCGACT TGCGGCCGCACGTTTGAT CTCCAGCTTGGTCCC-3' | SEQ ID NO: 69 |
| HuJκ3-NotI | 5'-GAGTCATTCTCGACTTGC GGCCGCACGTTTGATATCCAC TTTGGTCCC-3' | SEQ ID NO: 70 |
| HuJκ4-NotI | 5'-GAGTCATTCTCGACT TGCGGCCGCACGTTTGAT CTCCACCTTGGTCCC-3' | SEQ ID NO: 71 |

TABLE 9-continued

Human kappa chain variable region primers extended with SalI restriction sites (sense), human kappa chain J-region primers extended with NotI restriction sites (anti-sense), human lambda chain variable region primers extended with SalI restriction sites (sense) and human lambda chain J-region primers extended with NotI restriction sites (anti-sense).

| Primer name | Primer nucleotide sequence | SEQ ID NO |
|---|---|---|
| HuJκ5-NotI | 5'-GAGTCATTCTCGACTTGC GGCCGCACGTTTAATCTCCAG TCGTGTCCC-3' | SEQ ID NO: 72 |
| HuVλ1A-SalI | 5'-TGAGCACACAGGTCGACG CAGTCTGTGCTGACTCAGCCA CC-3' | SEQ ID NO: 73 |
| HuVλ1B-SalI | 5'-TGAGCACACAGGTCGACG CAGTCTGTGYTGACGCAGCCG CC-3' | SEQ ID NO: 74 |
| HuVλ1C-SalI | 5'-TGAGCACACAGGTCGACG CAGTCTGTCGTGACGCAGCCG CC-3' | SEQ ID NO: 75 |
| HuVλ2-SalI | 5'-TGAGCACACAGGTCGACG CARTCTGCCCTGACTCAGCCT-3' | SEQ ID NO: 76 |
| HuVλ3A-SalI | 5'-TGAGCACACAGGTCGACG TCCTATGWGCTGACTCAGCCA CC-3' | SEQ ID NO: 77 |
| HuVλ3B-SalI | 5'-TGAGCACACAGGTCGACG TCTTCTGAGCTGACTCAGGAC CC-3' | SEQ ID NO: 78 |
| HuVλ4-SalI | 5'-TGAGCACACAGGTCGACG CACGTTATACTGACTCAACCG CC-3' | SEQ ID NO: 79 |
| HuVλ5-SalI | 5'-TGAGCACACAGGTCGACG CAGGCTGTGCTGACTCAGCCG TC-3' | SEQ ID NO: 80 |
| HuVλG-SalI | 5'-TGAGCACACAGGTCGACG AATTTTATGCTGACTCAGCCC CA-3' | SEQ ID NO: 81 |
| HuVλ7/8-SalI | 5'-TGAGCACACAGGTCGACG CAGRCTGTGGTGACYCAGGAG CC-3' | SEQ ID NO: 82 |
| HuVλ9-SalI | 5'-TGAGCACACAGGTCGACG CWGCCTGTGCTGACTCAGCCM CC-3' | SEQ ID NO: 83 |
| HuJλ1-NotI | 5'-GAGTCATTCTCGACTTGC GGCCGCACCTAGGACGGTGAC CTTGGTCCC-3' | SEQ ID NO: 84 |
| HuJλ2/3-NotI | 5'-GAGTCATTCTCGACTTGC GGCCGCACCTAGGACGGTCAG CTTGGTCCC-3' | SEQ ID NO: 85 |
| HuJλ4/5-NotI | 5'-GAGTCATTCTCGACTTGC GGCCGCACYTAAAACGGTGAG CTGGGTCCC-3' | SEQ ID NO: 86 |

TABLE 10

Distribution of the different light chain products over the 10 fractions.

| Light chain products | Number of alleles | Fraction number | alleles/fraction |
|---|---|---|---|
| Vk1B/Jk1-5 | 19 | 1 and 2 | 9.5 |
| Vk2/Jk1-5 | 9 | 3 | 9 |
| Vk3B/Jk1-5 | 7 | 4 | 7 |
| Vk4B/Jk1-5 | 1 | 5 | 5 |
| Vk5/Jk1-5 | 1 | | |
| Vk6/Jk1-5 | 3 | | |
| Vλ1A/Jl1-3 | 5 | 6 | 5 |
| Vλ1B/Jl1-3 | | | |
| Vλ1C/Jl1-3 | | | |

TABLE 10-continued

Distribution of the different light chain products over the 10 fractions.

| Light chain products | Number of alleles | Fraction number | alleles/fraction |
|---|---|---|---|
| Vλ2/Jl1-3 | 5 | 7 | 5 |
| Vλ3A/Jl1-3 | 9 | 8 | 9 |
| Vλ3B/Jl1-3 | | | |
| Vλ4/Jl1-3 | 3 | 9 | 5 |
| Vλ5/Jl1-3 | 1 | | |
| Vλ6/Jl1-3 | 1 | | |
| Vλ7/8/Jl1-3 | 3 | 10 | 6 |
| Vλ9/Jl1-3 | 3 | | |

TABLE 11

Data of the single-chain Fvs capable of binding SARS-CoV.

| Name scFv | SEQ ID NO of nucleotide sequence | SEQ ID NO of amino acid sequence | HCDR3 | VH-germline | VL-germline |
|---|---|---|---|---|---|
| SC03-014 | 92 | 93 | GISPFYFDY (SEQ ID NO: 1) | $V_H$3 DP29 ($V_H$3-72) | $V_k$I DPK9 (02/012) |
| SC03-022 | 94 | 95 | GSGISTPMDV (SEQ ID NO: 2) | $V_H$5-51 (DP-73) | $V_K$IV(B3-DPK24) |

TABLE 12A

SARS-CoV neutralization experiment I.

| | | CR03-014 | | | CR03-022 | | | cIgG1 | | | Convalescent serum | | |
|---|---|---|---|---|---|---|---|---|---|---|---|---|---|
| dilution | Antibody | 1 | 2 | 3 | 4 | 5 | 6 | 7 | 8 | 9 | 10 | 11 | 12 |
| 4× | A | − | − | − | − | − | − | + | + | + | − | − | − |
| 8× | B | − | − | − | + | + | + | + | + | + | − | − | − |
| 16× | C | − | − | − | − | − | − | + | + | + | − | − | − |
| 32× | D | − | − | − | − | − | + | + | + | + | − | − | − |
| 64× | E | − | − | − | − | − | − | + | + | + | − | − | − |
| 128× | F | − | − | − | + | + | + | + | + | + | − | − | − |
| 256× | G | − | − | − | + | + | + | + | + | + | + | + | + |
| 512× | H | + | + | + | + | + | + | + | + | + | + | + | + |

TABLE 12B

SARS-CoV neutralization experiment II.

| | | CR03-014 | | | CR03-022 | | | cIgG1 | | | Convalescent serum | | |
|---|---|---|---|---|---|---|---|---|---|---|---|---|---|
| dilution | Antibody | 1 | 2 | 3 | 4 | 5 | 6 | 7 | 8 | 9 | 10 | 11 | 12 |
| 4× | A | − | − | − | − | − | + | + | + | + | − | − | − |
| 8× | B | − | − | − | + | + | − | + | + | + | − | − | − |
| 16× | C | − | − | − | + | − | − | + | + | + | − | − | − |
| 32× | D | − | − | − | + | + | − | + | + | + | − | − | − |
| 64× | E | − | + | − | − | − | − | + | + | + | − | − | − |
| 128× | F | − | − | + | + | + | + | + | + | + | + | − | − |
| 256× | G | − | − | − | + | + | + | + | + | + | + | + | + |
| 512× | H | + | + | + | + | + | + | + | + | + | + | + | + |

TABLE 12C

SARS-CoV neutralization experiment III.

| | | CR03-014 | | | CR03-022 | | | cIgG1 | | | Convalescent serum | | |
|---|---|---|---|---|---|---|---|---|---|---|---|---|---|
| dilution | Antibody | 1 | 2 | 3 | 4 | 5 | 6 | 7 | 8 | 9 | 10 | 11 | 12 |
| 4× | A | − | − | − | − | − | − | + | + | + | − | − | − |
| 8× | B | − | − | − | − | − | − | + | + | + | − | − | − |
| 16× | C | − | − | − | − | − | − | + | + | + | − | − | − |
| 32× | D | − | − | − | − | − | − | + | + | + | − | − | − |
| 64× | E | − | − | − | − | + | + | + | + | + | − | − | − |
| 128× | F | − | − | − | + | + | + | + | + | + | − | + | − |
| 256× | G | + | + | + | + | + | + | + | + | + | + | + | + |
| 512× | H | + | + | + | + | + | + | + | + | + | + | + | + |

−: No CPE
+: CPE

TABLE 13

Concentrations of the monoclonal anti-SARS-CoV antibody CR03-014 giving complete protection against 100 $TCID_{50}$ of the different SARS-CoV isolates indicated in an in vitro neutralization assay.

| SARS-CoV Strain* | Concentration of CR03-014 (μg/ml) resulting in 100% protection against 100 $TCID_{50}$ |
|---|---|
| 36 (3) | 12.5 |
| 39849 (3) | 12.5 |
| 66 (2) | 12.5 |
| 61567 (2) | 12.5 |
| 61644 (1) | 12.5 |
| 61644 (15) | 12.5 |
| GZ43[1] | 12.5 |
| GZ50[1] | 12.5 |

*Between brackets the passage numbers of the respective strains is indicated.
[1]For strains GZ43 and GZ50 the passage history is unknown.

TABLE 14

SARS-CoV neutralization experiment of several mixtures of CR03-014 and CR03-022.

| | CR03-014 (625 | CR03-022 (2.5 | Wells protected at indicated dilution | | | | | | | |
|---|---|---|---|---|---|---|---|---|---|---|
| Mix | μg/ml) % | mg/ml) % | 16× | 32× | 64× | 128× | 256× | 512× | 1024× | Titer |
| A | 0 | 100 | 6/6 | 6/6 | 5/6 | 3/6 | 3/6 | 0/6 | 0/6 | 64 |
| B | 10 | 90 | 6/6 | 6/6 | 6/6 | 6/6 | 6/6 | 2/6 | 0/6 | 256 |
| C | 50 | 50 | 6/6 | 6/6 | 6/6 | 6/6 | 6/6 | 6/6 | 4/6 | >1024 |
| D | 90 | 10 | ND | 6/6 | 6/6 | 6/6 | 4/6 | 1/6 | 0/6 | 256 |
| E | 100 | 0 | 5/6 | 2/6 | 0/6 | 0/6 | 0/6 | 0/6 | 0/6 | 16 |

TABLE 15

List of SARS-CoV strains having a region 318-510 of the S protein not identical to the region 318-510 of the S protein of SARS-CoV Frankfurt 1 strain.

| Mutation | Strain | Genbank |
|---|---|---|
| K344R | GZ02 | AY390556 |
| | GZ60 | AY304491 |
| | JMD | AY394988 |
| | ZS-B | AY394996 |
| | GZ43 | AY304490 |
| | HGZ8L1-A | AY394981 |
| | ZS-A | AY394997 |
| | ZS-C | AY395003 |

TABLE 15-continued

List of SARS-CoV strains having a region 318-510 of the S protein not identical to the region 318-510 of the S protein of SARS-CoV Frankfurt 1 strain.

| Mutation | Strain | Genbank |
|---|---|---|
| K344R | GD01 | AY278489 |
| F501Y | | |
| K344R | GD03T0013 | AY525636 |
| F360S | | |
| L472P | | |
| D480G | | |
| T487S | | |
| S353F | Sin3408 | AY559083 |
| | Sin3765V | AY559084 |
| | Sin845 | AY559093 |
| | Sin847 | AY559095 |
| | Sin849 | AY559086 |
| | Sin852 | AY559082 |
| | Sin3725V | AY559087 |
| | Sin842 | AY559081 |

TABLE 15-continued

List of SARS-CoV strains having a region 318-510 of the S protein not identical to the region 318-510 of the S protein of SARS-CoV Frankfurt 1 strain.

| Mutation | Strain | Genbank |
|---|---|---|
| | Sin846 | AY559094 |
| | Sin848 | AY559085 |
| | Sin850 | AY559096 |
| R426G | Shanghai LY | AY322205S3 |
| N437D | | |
| Y436H | GZ-C | AY394979 |
| Y442S | Sino1-11 | AY485277 |
| N479S | BJ302 cl. 2 | AY429073 |

TABLE 15-continued

List of SARS-CoV strains having a region 318-510 of the S protein not identical to the region 318-510 of the S protein of SARS-CoV Frankfurt 1 strain.

| Mutation | Strain | Genbank |
|---|---|---|
| | BJ302 cl. 4 | AY429075 |
| | BJ302 cl. 6 | AY429077 |
| | BJ302 cl. 3 | AY429074 |
| | BJ302 cl. 5 | AY429076 |
| | BJ302 cl. 8 | AY429079 |

The amino acid substitutions compared to the Frankfurt 1 S protein are indicated in the left column. Strain and GenBank accession number are indicated in second and third column.

TABLE 16

Neutralization Index of E014 escape viruses

| Escape virus | Log ($TCID_{50}$/ml) without mAb | Log ($TCID_{50}$/ml) with mAb | NI |
|---|---|---|---|
| E014-C06 | 7.45 | 7.53 | 0 |
| E014-C07 | 7.07 | 6.85 | 0.22 |
| E014-C08 | 7.83 | 7.1 | 0.73 |
| E014-C09 | 7.53 | 6.85 | 0.68 |
| E014-C10 | 6.77 | 7.1 | 0 |
| Wt SARS-CoV | 7.23 | 3.93 | 3.3 |

TABLE 17

Neutralization index of putative E022 escape viruses

| Virus | Log ($TCID_{50}$/ml) without mAb | Log ($TCID_{50}$/ml) with mAb | NI | Escape |
|---|---|---|---|---|
| Wt SARS-CoV | 7.3 | 4 | 3.3 | No |
| E22-2 | 7.3 | 2.5 | 4.8 | No |
| E22-3 | 7.45 | 2.5 | 4.95 | No |
| E22-5 | 7.3 | 2.7 | 4.6 | No |
| E22-6 | 7.3 | 2.95 | 4.35 | No |
| E22-9 | 8.1 | 3.7 | 4.4 | No |

TABLE 18

CR03-022 neutralizing titers for two representative escape viruses of CR03-014

| Virus | Titer (μg/ml)[a] | Titer (μg/ml)[b] |
|---|---|---|
| Wild-type | 35.46 | 50.00 |
| E14-6 | 25.00 | 50.00 |
| E14-7 | 31.50 | 50.00 |

[a]50% neutralizing titer of CR03-022 for each virus is indicated in μg/ml
[b]100% neutralizing titer of CR03-022 for each virus is indicated in μg/ml

REFERENCES

Boel E., S. Verlaan, M. J. Poppelier, N. A. Westerdaal, J. A. Van Strijp and T. Logtenberg (2000), Functional human monoclonal antibodies of all isotypes constructed from phage display library-derived single-chain Fv antibody fragments. *J. Immunol. Methods* 239:153-166.

Burton D. R. and C. F. Barbas (1994), Human antibodies from combinatorial libraries. *Adv. Immunol.* 57:191-280.

Chou, T. C. and P. Talalay (1984), Quantitative analysis of dose-effect relationships: the combined effects of multiple drugs or enzyme inhibitors. *Adv. Enzyme Regul.* 22:27-55.

De Kruif J., L. Terstappen, E. Boel and T. Logtenberg (1995a), Rapid selection of cell subpopulation-specific human monoclonal antibodies from a synthetic phage antibody library. *Proc. Natl. Acad. Sci. U.S.A.* 92:3938.

De Kruif J., E. Boel and T. Logtenberg (1995b), Selection and application of human single-chain Fv antibody fragments from a semi-synthetic phage antibody display library with designed CDR3 regions. *J. Mol. Biol.* 248:97-105.

Emini E. A., P. L. Nara, W. A. Schleif, J. A. Lewis, J. P. Davide, D. R. Lee, J. Kessler, S. Conley, S. Matsushita, S. D. J. Putney, R. J. Gerety and J. W. Eichberg (1990), Antibody-mediated in vitro neutralization of human immunodeficiency virus type 1 abolishes infectivity for chimpanzees. *J. Virol.* 64:3674-3678.

Fouchier R. A., T. Kuiken, M. Schutten, G. van Amerongen, G. J. van Doornum, B. G. van den Hoogen, M. Peiris, W. Lim, K. Stohr, A. D. Osterhaus (2003), Koch's postulates fulfilled for SARS virus. *Nature* 243:240.

Guan Y., B. J. Zheng, Y. Q. He, X. L. Liu, Z. X. Zhuang, C. L. Cheung, S. W. Luo, P. H. Li, L. J. Zhang, Y. J. Guan, K. M. Butt, K. L. Wong, K. W. Chan, W. Lim, K. F. Shortridge, K. Y. Yuen, J. S. Peiris, and L. L. Poon (2003), Isolation and characterization of viruses related to the SARS coronavirus from animals in southern China. *Science* 302:276-278.

Havenga M. J., A. A. Lemckert, J. M. Grimbergen, R. Vogels, L. G. Huisman, D. Valerio, A. Bout and P. H. Quax (2001), Improved adenovirus vectors for infection of cardiovascular tissues. *J. Virol.* 75:3335-3342.

Holmes K. V. (2003), SARS coronavirus: a new challenge for prevention and therapy. *J. Clin. Invest.* 111:1605-1609.

Huls G., I. J. Heijnen, E. Cuomo, J. van der Linden, E. Boel, J. van de Winkel and T. Logtenberg (1999), Antitumor immune effector mechanisms recruited by phage display-derived fully human IgG1 and IgA1 monoclonal antibodies. *Cancer Res.* 59:5778-5784.

Ksiazek T. G., D. Erdman, C. S. Goldsmith, S. R. Zaki, T. Peret, S. Emery, S. Tong, C. Urbani, J. A. Corner, W. Lim, P. E. Rollin, S. F. Dowell, A. E. Ling, C. D. Humphrey, W. J. Shieh, J. Guarner, C. D. Paddock, P. Rota, B. Fields, J. DeRisi, J. Y. Yang, N. Cox, J. M. Hughes, J. W. LeDuc, W. J. Bellini, L. J. Anderson (2003), A novel coronavirus associated with severe acute respiratory syndrome. *N. Eng. J. Med.* 348:1953-1966.

Kuiken T., R. A. Fouchier, M. Schutten, G. F. Rimmelzwaan, G. van Amerongen, D. van Riel, J. D. Laman, T. de Jong, G. van Doornum, W. Lim, A. E. Ling, P. K. Chan, J. S. Tam, M. C. Zambon, R. Gopal, C. Drosten, S. van der Werf, N. Escriou, J. C. Manuguerra, K. Stohr, J. S. Peiris and A. D. Osterhaus (2003), Newly discovered coronavirus as the primary cause of severe acute respiratory syndrome. *Lancet* 362:263-270.

Li W., M. J. Moore, N. Vasilieva, J. Sui, S. K. Wong, M. A. Berne, M. Somasundaran, J. L. Sullivan, K. Luzuriaga, T. C. Greenough, H. Choe and M. Farzan (2003), Angiotensin-converting enzyme 2 is a functional receptor for the SARS coronavirus. *Nature* 2003 426:450-454.

Marra M. A., S. J. Jones, C. R. Astell, R. A. Holt, A. Brooks-Wilson, Y. S. Butterfield, J. Khattra, J. K. Asano, S. A. Barber, S. Y. Chan, A. Cloutier, S. M. Coughlin, D. Freeman, N. Girn, O. L. Griffith, S. R. Leach, M. Mayo, H. McDonald, S. B. Montgomery, P. K. Pandoh, A. S. Petrescu, A. G. Robertson, J. E. Schein, A. Siddiqui, D. E. Smailus, J. M. Stott, G. S. Yang, F. Plummer, A. Andonov, H. Artsob, N. Bastien, K. Bernard, T. F. Booth, D. Bowness, M. Czub, M. Drebot, L. Fernando, R. Flick, M. Garbutt, M. Gray, A. Grolla, S. Jones, H. Feldmann, A. Meyers, A. Kabani, Y. Li, S, Normand, U. Stroher, G. A. Tipples, S.

Tyler, R. Vogrig, D. Ward, B. Watson, R. C. Brunham, M. Krajden, M. Petric, D. M. Skowronski, C. Upton, and R. L. Roper (2003), The genome sequence of the SARS-associated coronavirus. *Science* 300, 1399-1404.

Nicholls J. M., L. L. Poon, K. C. Lee, W. F. Ng, S. T. Lai, C. Y. Leung, C. M. Chu, P. K. Hui, K. L. Mak, W. Lim, K. W. Yan, K. H. Chan, N. C. Tsang, Y. Guan, K. Y. Yuen, and J. S. Peiris (2003), Lung pathology of fatal severe acute respiratory syndrome. *Lancet* 361:1773-1778.

Poon L. L. M., C. S. W. Leung, K. H. Yuen, Y. Guan, and J. S. M. Peiris (2005), Recurrent mutations associated with isolation and passage of SARS Coronavirus in cells from non-human primates. *J. Med. Virol.* 76:435-440.

Rickerts V., T. Wolf, C. Rottmann, W. Preiser, C. Drosten, V. Jakobi, H. N. Leong, H. R. Brodt (2003), Klinik and Behandlung des schweren akuten respiratorischen Syndroms. *Dtsch. Med. Wochenschrift* 128:1109-1114.

Rota P. A., M. S. Oberste, S. S. Monroe, W. A. Nix, R. Campagnoli, J. P. Icenogle, S. Penaranda, B. Bankamp, K. Maher, M. H. Chen, S. Tong, A. Tamin, L. Lowe, M. Frace, J. L. DeRisi, Q. Chen, D. Wang, D. D. Erdman, T. C. Peret, C. Burns, T. G. Ksiazek, P. E. Rollin, A. Sanchez, S. Liffick, B. Holloway, J. Limor, K. McCaustland, M. Olsen-Rasmussen, R. Fouchier, S. Gunther, A. D. Osterhaus, C. Drosten, M. A. Pallansch, L. J. Anderson, and W. J. Bellini (2003), Characterization of a novel coronavirus associated with severe acute respiratory syndrome. *Science* 300:1394-1399.

Slootstra J. W., W. C. Puijk, G. J. Ligtvoet, J. P. Langeveld, R. H. Meloen (1996), Structural aspects of antibody-antigen interaction revealed through small random peptide libraries. *Mol. Divers.* 1:87-96.

Ter Meulen J., A. B. H. Bakker, E. N. van den Brink, G. J. Weverling, B. E. E. Martina, B. L. Haagmans, T. Kuiken, J. de Kruif, W. Preiser, W. Spaan, H. R. Gelderblom, J. Goudsmit, A. D. M. E. Osterhaus (2004), Human monoclonal antibody as prophylaxis for SARS coronavirus infection in ferrets. *The Lancet* 363:2139-2141.

---

The invention claimed is:

1. A composition comprising at least two immunoglobulins that are capable of specifically binding to Spike (S) protein of Severe Acute Respiratory Syndrome Coronavirus (SARS-Co-V) and neutralizing SARS-CoV, wherein the first immunoglobulin comprises a heavy chain variable region comprising the amino acid sequence of SEQ ID NO: 4 and a light chain variable region comprising the amino acid sequence of SEQ ID NO: 8, and wherein the second immunoglobulin comprises a heavy chain variable region comprising the amino acid sequence of SEQ ID NO: 6 and a light chain variable region comprising the amino acid sequence of SEQ ID NO: 10, and wherein the relative amounts of the at least two immunoglobulins are such that they exhibit a synergistic neutralizing activity.

2. The composition of claim 1, wherein the immunoglobulins are capable of reacting with different, non-competing epitopes of the S protein of SARS-CoV.

3. The composition of claim 2, wherein the immunoglobulins are capable of reacting with different, non-competing epitopes of amino acids 318-510 of the S protein (SEQ ID NO:115) of SARS-CoV.

4. The composition of claim 1, wherein at least one of the immunoglobulins is capable of reacting with an animal SARS-like CoV at a region corresponding to amino acids 318-510 of the S protein (SEQ ID NO: 115) of SARS-CoV.

5. The composition of claim 4, wherein at least one of the immunoglobulins is capable of reacting with amino acids 318-510 of the S protein (SEQ ID NO: 115) to a similar extent as with amino acids 318-510 of the S protein-having a N479K substitution.

6. The composition of claim 1, wherein each of the immunoglobulins is capable of neutralizing a plurality of SARS-CoV strains.

7. The composition of claim 1, wherein the two immunoglobulins have a molar ratio of from 1:100 to 100:1.

8. The composition of claim 1, further comprising a pharmaceutically acceptable excipient.

9. A powder composition for reconstitution, the composition comprising two immunoglobulin molecules that are capable of specifically binding to S protein of SARS-CoV, wherein the immunoglobulin molecule comprising a heavy chain variable region comprising the amino acid sequence of SEQ ID NO: 6 and a light chain variable region comprising the amino acid sequence of SEQ ID NO: 10; and the second immunoglobulin molecule comprising a heavy chain variable region comprising the amino acid sequence of SEQ ID NO: 4, and a light chain variable region comprising the amino acid sequence of SEQ ID NO: 8.

10. A method of detecting a Severe Acute Respiratory Syndrome Coronavirus (SARS-Co-V) in a sample, said method comprising the steps of: contacting a sample with a diagnostically effective amount of the immunoglobulins of claim 1, and determining whether the immunoglobulins specifically binds to a molecule of the sample.

11. The method of claim 10, wherein the sample is a sample taken from a human subject potentially infected with a SARS-CoV.

* * * * *